(12) United States Patent
Goodall et al.

(10) Patent No.: US 10,327,984 B2
(45) Date of Patent: Jun. 25, 2019

(54) CONTROLLING EAR STIMULATION IN RESPONSE TO IMAGE ANALYSIS

(71) Applicant: Elwha LLC, Bellevue, WA (US)

(72) Inventors: Eleanor V. Goodall, Seattle, WA (US); Roderick A. Hyde, Redmond, WA (US); Muriel Y. Ishikawa, Livermore, CA (US); Jordin T. Kare, San Jose, CA (US); Melanie K. Kitzan, North Bend, WA (US); Eric C. Leuthardt, St. Louis, MO (US); Mark A. Malamud, Seattle, WA (US); Stephen L. Malaska, Snoqualmie, WA (US); Nathan P. Myhrvold, Medina, WA (US); Brittany Scheid, St. Louis, MO (US); Katherine E. Sharadin, Redmond, WA (US); Elizabeth A. Sweeney, Seattle, WA (US); Clarence T. Tegreene, Mercer Island, WA (US); Charles Whitmer, North Bend, WA (US); Lowell L. Wood, Jr., Bellevue, WA (US); Victoria Y. H. Wood, Livermore, CA (US)

(73) Assignee: eQuility LLC, Bellevue, WA (US)

( * ) Notice: Subject to any disclaimer, the term of this patent is extended or adjusted under 35 U.S.C. 154(b) by 191 days.

(21) Appl. No.: 15/340,058

(22) Filed: Nov. 1, 2016

(65) Prior Publication Data

US 2017/0113042 A1    Apr. 27, 2017

Related U.S. Application Data

(63) Continuation-in-part of application No. 14/670,504, filed on Mar. 27, 2015, now Pat. No. 10,039,928, and
(Continued)

(51) Int. Cl.
 *A61N 1/36* (2006.01)
 *A61N 2/00* (2006.01)
 (Continued)

(52) U.S. Cl.
 CPC ........... *A61H 23/02* (2013.01); *A61N 1/0456* (2013.01); *A61N 1/0472* (2013.01);
 (Continued)

(58) Field of Classification Search
 CPC ...... A61N 2/006; A61N 2/02; A61N 1/36014; A61N 7/00; A61N 2/002; A61N 1/0484;
 (Continued)

(56) References Cited

U.S. PATENT DOCUMENTS

| 4,641,349 A | 2/1987 | Flom et al. |
| 4,966,164 A | 10/1990 | Colsen et al. |

(Continued)

FOREIGN PATENT DOCUMENTS

| DE | 10 2006 023 824 A1 | 11/2007 |
| WO | WO 2008/143371 A1 | 11/2008 |

OTHER PUBLICATIONS

Kong et al.; "Treating Depression with Transcutaneous Auricular Vagus Nerve Stimulation: State of the Art and Future Perspectives"; Frontiers in Psychiatry; Feb. 5, 2018; vol. 9, Article 20; pp. 1-8.
(Continued)

Primary Examiner — Christine H Matthews
Assistant Examiner — Joshua Daryl D Lannu

(57) ABSTRACT

Systems and related methods for controlling an ear stimulation device with a personal computing device, based on analysis of an image of a user of the personal computing device captured with a camera associated with the personal computing device, are described. One or more parameter is determined from the processed image, including, but not limited to, user identity, emotion, physiological condition, or
(Continued)

placement of a stimulator earpiece, and control of the ear stimulation device is based thereon. If the earpiece is located incorrectly, in an aspect, delivery of a stimulus is prevented. In another aspect, the user is notified of the need to reposition an incorrectly located earpiece.

44 Claims, 47 Drawing Sheets

Related U.S. Application Data a continuation-in-part of application No. 14/670,537, filed on Mar. 27, 2015, and a continuation-in-part of application No. 14/670,560, filed on Mar. 27, 2015, and a continuation-in-part of application No. 14/670,582, filed on Mar. 27, 2015, and a continuation-in-part of application No. 14/670,620, filed on Mar. 27, 2015, and a continuation-in-part of application No. 14/670,656, filed on Mar. 27, 2015, and a continuation-in-part of application No. 15/291,358, filed on Oct. 12, 2016.

(51) Int. Cl.
| | |
|---|---|
| *A61H 23/00* | (2006.01) |
| *A61N 1/04* | (2006.01) |
| *A61H 23/02* | (2006.01) |
| *A61N 1/372* | (2006.01) |
| *A61N 2/02* | (2006.01) |
| *A61N 7/00* | (2006.01) |
| *A61N 5/06* | (2006.01) |
| *A63F 13/212* | (2014.01) |
| *A63F 13/424* | (2014.01) |

(52) U.S. Cl.
CPC ..... *A61N 1/36014* (2013.01); *A61N 1/36036* (2017.08); *A61N 1/37247* (2013.01); *A61N 1/37258* (2013.01); *A61N 2/002* (2013.01); *A61N 2/006* (2013.01); *A61N 5/0622* (2013.01); *A61N 7/00* (2013.01); *A61N 1/0484* (2013.01); *A61N 1/36021* (2013.01); *A61N 1/36025* (2013.01); *A61N 2/02* (2013.01); *A61N 2005/0647* (2013.01); *A61N 2007/0026* (2013.01); *A63F 13/212* (2014.09); *A63F 13/424* (2014.09)

(58) Field of Classification Search
CPC ............ A61N 1/36021; A61N 1/36025; A61N 1/37247; A61N 1/0456; A61N 1/0472; A61N 1/36036; A63F 13/212; A63F 13/424; A61B 5/00; G06T 7/00
See application file for complete search history.

(56) References Cited

U.S. PATENT DOCUMENTS

| | | |
|---|---|---|
| 5,184,617 A | 2/1993 | Harris et al. |
| 5,285,781 A | 2/1994 | Brodard |
| 5,304,112 A | 4/1994 | Mrklas et al. |
| 5,501,230 A | 3/1996 | Laribiere |
| 5,572,596 A | 11/1996 | Wildes et al. |
| 5,788,656 A | 8/1998 | Mino |
| 5,913,310 A | 6/1999 | Brown |
| 6,016,449 A | 1/2000 | Fischell et al. |
| 6,162,186 A | 12/2000 | Scinto et al. |
| 6,186,145 B1 | 2/2001 | Brown |
| 6,231,344 B1 | 5/2001 | Merzenich et al. |
| 6,234,435 B1 | 5/2001 | Yeh |
| 6,314,324 B1 | 11/2001 | Lattner et al. |
| 6,430,443 B1 | 8/2002 | Karell |
| 6,442,422 B1 | 8/2002 | Duckert |
| 7,226,026 B2 | 6/2007 | Lin |
| 7,229,059 B1 | 6/2007 | Hood |
| 7,516,926 B2 | 4/2009 | Liu |
| 7,628,362 B2 | 12/2009 | Song |
| 7,658,354 B2 | 2/2010 | Wang |
| 7,706,875 B2 | 4/2010 | Buras et al. |
| 7,774,052 B2 | 8/2010 | Burton et al. |
| 7,797,042 B2 | 9/2010 | Dietrich et al. |
| 7,801,686 B2 | 9/2010 | Hyde et al. |
| D628,990 S | 12/2010 | Pedersen |
| D630,621 S | 1/2011 | Pedersen |
| 7,878,467 B2 | 2/2011 | Chen et al. |
| D634,306 S | 3/2011 | Pedersen |
| 7,913,963 B2 | 3/2011 | Cheng et al. |
| 7,974,787 B2 | 7/2011 | Hyde et al. |
| 8,001,472 B2 | 8/2011 | Gilley et al. |
| 8,155,750 B2 | 4/2012 | Jaax et al. |
| 8,157,730 B2 | 4/2012 | LeBoeuf et al. |
| 8,170,658 B2 | 5/2012 | Dacey, Jr. et al. |
| 8,204,786 B2 | 6/2012 | LeBoeuf et al. |
| 8,229,178 B2 | 7/2012 | Zhang et al. |
| D666,169 S | 8/2012 | Tucker et al. |
| 8,235,724 B2 | 8/2012 | Gilley et al. |
| 8,251,903 B2 | 8/2012 | LeBoeuf et al. |
| 8,267,983 B2 | 9/2012 | Rogers |
| 8,267,984 B2 | 9/2012 | Rogers |
| 8,429,223 B2 | 4/2013 | Gilley et al. |
| 8,488,023 B2 | 7/2013 | Bacivarov et al. |
| 8,506,469 B2 | 8/2013 | Dietrich et al. |
| 8,512,242 B2 | 8/2013 | LeBoeuf et al. |
| 8,612,008 B2 | 12/2013 | Kirsch et al. |
| 8,615,290 B2 | 12/2013 | Lin et al. |
| 8,630,436 B2 | 1/2014 | Berg |
| 8,647,270 B2 | 2/2014 | LeBoeuf et al. |
| 8,652,040 B2 | 2/2014 | LeBoeuf et al. |
| 8,700,111 B2 | 4/2014 | LeBoeuf et al. |
| 8,702,607 B2 | 4/2014 | LeBoeuf et al. |
| 8,745,496 B2 | 6/2014 | Gilley et al. |
| 8,755,892 B2 | 6/2014 | Amurthur et al. |
| 8,788,002 B2 | 7/2014 | LeBoeuf et al. |
| 8,808,195 B2 | 8/2014 | Tseng et al. |
| 8,876,688 B2 | 11/2014 | Hyde et al. |
| 8,976,995 B2 | 3/2015 | Berg |
| 9,025,800 B2 | 5/2015 | Kidmose et al. |
| 9,036,018 B2 | 5/2015 | Wang et al. |
| D744,456 S | 12/2015 | Pedersen |
| 9,415,220 B1 | 8/2016 | Spinelli et al. |
| 9,554,632 B2 | 1/2017 | Tarnow et al. |
| 9,609,105 B1 | 3/2017 | Krug et al. |
| 9,625,251 B2 | 4/2017 | Heaton et al. |
| 9,643,695 B1 | 5/2017 | Breaux et al. |
| 9,685,986 B2 | 6/2017 | Lee et al. |
| 10,130,809 B2 | 11/2018 | Cartledge et al. |
| 2002/0072781 A1 | 6/2002 | Lattner et al. |
| 2002/0077560 A1 | 6/2002 | Kramer et al. |
| 2002/0143242 A1 | 10/2002 | Nemirovski |
| 2003/0195588 A1 | 10/2003 | Fischell et al. |
| 2004/0207720 A1 | 10/2004 | Miyahara et al. |
| 2005/0084832 A1 | 4/2005 | Janssen et al. |
| 2005/0165460 A1 | 7/2005 | Erfan |
| 2006/0020161 A1 | 1/2006 | Mageras et al. |
| 2006/0064037 A1 | 3/2006 | Shalon et al. |
| 2006/0094974 A1 | 5/2006 | Cain |
| 2007/0150027 A1 | 6/2007 | Rogers |
| 2007/0167999 A1 | 7/2007 | Breden et al. |
| 2007/0250145 A1 | 10/2007 | Kraus et al. |
| 2008/0021517 A1 | 1/2008 | Dietrich |
| 2008/0051852 A1 | 2/2008 | Dietrich et al. |
| 2008/0076972 A1 | 3/2008 | Dorogusker et al. |
| 2008/0249439 A1 | 10/2008 | Tracey et al. |
| 2008/0285813 A1 | 11/2008 | Holm |
| 2008/0288016 A1 | 11/2008 | Amurthur et al. |
| 2009/0076561 A1 | 3/2009 | Libbus et al. |
| 2009/0082831 A1 | 3/2009 | Paul et al. |
| 2009/0187124 A1 | 7/2009 | Ludlow et al. |
| 2009/0269329 A1 | 10/2009 | Hyde et al. |
| 2009/0271009 A1 | 10/2009 | Hyde et al. |
| 2009/0271375 A1 | 10/2009 | Hyde et al. |

(56) References Cited

U.S. PATENT DOCUMENTS

| | | | |
|---|---|---|---|
| 2009/0287067 A1 | 11/2009 | Dorogusker et al. | |
| 2010/0004709 A1 | 1/2010 | Mische | |
| 2010/0057154 A1 | 3/2010 | Dietrich et al. | |
| 2010/0098915 A1 | 4/2010 | Hanlon | |
| 2010/0198282 A1 | 8/2010 | Rogers | |
| 2010/0198318 A1 | 8/2010 | Rogers | |
| 2010/0222845 A1 | 9/2010 | Goetz | |
| 2010/0278364 A1 | 11/2010 | Berg | |
| 2011/0073608 A1 | 3/2011 | Richardson et al. | |
| 2011/0112427 A1 | 5/2011 | Phillips et al. | |
| 2011/0166619 A1 | 7/2011 | de Vos | |
| 2011/0166624 A1 | 7/2011 | Dietrich et al. | |
| 2011/0184247 A1 | 7/2011 | Contant et al. | |
| 2011/0224750 A1 | 9/2011 | Scheiner | |
| 2011/0295335 A1 | 12/2011 | Sharma et al. | |
| 2011/0295336 A1 | 12/2011 | Sharma et al. | |
| 2011/0307025 A1 | 12/2011 | Libbus et al. | |
| 2011/0307027 A1 | 12/2011 | Sharma et al. | |
| 2011/0307028 A1 | 12/2011 | Sharma et al. | |
| 2012/0086551 A1 | 4/2012 | Lowe et al. | |
| 2012/0177233 A1 | 7/2012 | Kidmose et al. | |
| 2012/0253236 A1 | 10/2012 | Snow et al. | |
| 2012/0310077 A1 | 12/2012 | Rogers | |
| 2012/0310295 A1 | 12/2012 | Libbus et al. | |
| 2013/0019237 A1 | 1/2013 | Pardehpoosh et al. | |
| 2013/0072996 A1 | 3/2013 | Kilgard et al. | |
| 2013/0137918 A1 | 5/2013 | Phillips et al. | |
| 2013/0190556 A1* | 7/2013 | Wetmore | A61M 21/02 600/28 |
| 2013/0190840 A1 | 7/2013 | Libbus et al. | |
| 2013/0245486 A1 | 9/2013 | Simon et al. | |
| 2013/0253365 A1 | 9/2013 | Crosson et al. | |
| 2014/0028243 A1 | 1/2014 | Rayner | |
| 2014/0038147 A1 | 2/2014 | Morrow | |
| 2014/0051939 A1 | 2/2014 | Messerschmidt | |
| 2014/0105431 A1 | 4/2014 | Berg | |
| 2014/0135596 A1 | 5/2014 | LeBoeuf et al. | |
| 2014/0140567 A1 | 5/2014 | LeBoeuf et al. | |
| 2014/0217862 A1 | 8/2014 | Rayner | |
| 2014/0222100 A1 | 8/2014 | Libbus et al. | |
| 2014/0265765 A1 | 9/2014 | Khodapanah et al. | |
| 2014/0276270 A1 | 9/2014 | Ludlow et al. | |
| 2014/0312090 A1 | 10/2014 | Garza, Jr. | |
| 2014/0330334 A1 | 11/2014 | Errico et al. | |
| 2014/0375186 A1 | 12/2014 | Tarnow et al. | |
| 2015/0115877 A1 | 4/2015 | Arai et al. | |
| 2015/0119770 A1 | 4/2015 | Driscoll et al. | |
| 2015/0141879 A1 | 5/2015 | Harper et al. | |
| 2015/0150498 A1 | 6/2015 | George et al. | |
| 2015/0150499 A1 | 6/2015 | George et al. | |
| 2015/0150501 A1 | 6/2015 | George et al. | |
| 2015/0215693 A1 | 7/2015 | Sandanger | |
| 2015/0238762 A1 | 8/2015 | Pal et al. | |
| 2015/0281822 A1 | 10/2015 | Berg | |
| 2015/0290076 A1 | 10/2015 | Hobbs et al. | |
| 2015/0312665 A1 | 10/2015 | Berg | |
| 2015/0360030 A1 | 12/2015 | Cartledge et al. | |
| 2016/0001096 A1 | 1/2016 | Mishelevich | |
| 2016/0026781 A1 | 1/2016 | Boczek | |
| 2016/0045730 A1 | 2/2016 | Kim et al. | |
| 2016/0067497 A1 | 3/2016 | Levine et al. | |
| 2016/0100676 A1 | 4/2016 | Sandanger | |
| 2016/0205456 A1 | 7/2016 | Berg | |
| 2017/0027812 A1 | 2/2017 | Hyde et al. | |
| 2017/0080231 A1 | 3/2017 | Libbus et al. | |
| 2017/0085283 A1 | 3/2017 | Rayner | |
| 2017/0087364 A1 | 3/2017 | Cartledge et al. | |
| 2017/0134063 A1 | 5/2017 | Lee et al. | |
| 2017/0194083 A1 | 7/2017 | Bohannon | |
| 2017/0203103 A1 | 7/2017 | Levine et al. | |
| 2017/0231490 A1 | 8/2017 | Toth et al. | |
| 2017/0246481 A1 | 8/2017 | Mishelevich | |
| 2017/0278370 A1 | 9/2017 | Kaib et al. | |
| 2017/0368329 A1 | 12/2017 | Tyler et al. | |
| 2017/0368344 A1 | 12/2017 | Ironi et al. | |

OTHER PUBLICATIONS

PCT International Search Report; International App. No. PCT/US2017/056279; dated Feb. 23, 2018; pp. 1-6.
U.S. Appl. No. 14/670,656, Hyde et al.
U.S. Appl. No. 14/670,620, Hyde et al.
U.S. Appl. No. 14/670,582, Hyde et al.
U.S. Appl. No. 14/670,560, Hyde et al.
U.S. Appl. No. 14/670,537, Hyde et al.
U.S. Appl. No. 14/670,504, Hyde et al.
Aleksic et al.; "Audio-Visual Biometrics"; Proceedings of the IEEE; Nov. 2006; pp. 2025-2044; vol. 94, No. 11; IEEE.
Alvord et al.; "Anatomy and Orientation of the Human External Ear"; Journal of the American Academy of Audiology; Dec. 1997; pp. 383-390; vol. 8, No. 6.
Aymanns et al.; "Homotopic long-term depression of trigeminal pain and blink reflex within one side of the human face"; Clinical Neurophysiology; 2009; pp. 2093-2099; vol. 120; Elsevier Ireland Ltd.
Bayometric; "Crossmatch Retinal Scan 2 Iris Scanner"; Oct. 26, 2016; pp. 1-2; located at http://www.bayometric.com/crossmatch-retinal-scan-2-iris-scanner/.
Berlim et al.; "Current trends in the assessment and somatic treatment of resistant/refractory major depression: an overview"; Ann. Med.; 2008; pp. 149-159; vol. 40, No. 2 (Abstract only).
Biosciencetechnology; "New Non-invasive Form of Vagus Nerve Stimulation Treats Depression"; bearing a date of Feb. 9, 2016; pp. 1-2; located at http://www.biosciencetechnology.com/news/2016/02/new-non-invsive-form-vagus-nerve-stimulation-treats-depression.
Biospace; "Measuring 'Moodtraces': New App Helps Monitor Depression"; Feb. 27, 2015; pp. 1-2; located at http://www.biospace.com/news_print.asp?NewsEntityId=366575.
Bystritsky et al.; "A Pilot Study of Cranial Electrotherapy Stimulation for Generalized Anxiety Disorder"; Feb. 6, 2008; pp. el-e6; Physicians Postgraduate Press, Inc.
Carreno et al.; "The Allure of Transcutaneous Vagus Nerve Stimulation as a Novel Therapeutic Modality"; Biological Psychiatry; Feb. 15, 2016; pp. 260-261; vol. 79; Society of Biological Psychiatry.
Clancy et al.; "Non-invasive Vagus Nerve Stimulation in Healthy Humans Reduces Sympathetic Nerve Activity"; Brain Stimulation; 2014; pp. 871-877; vol. 7; Elsevier Inc.
Cook et al.; "Effects of Adjunctive Trigeminal Nerve Stimulation in Major Depressive Disorder in a Dose Ranging Trial"; First International Brain Stimulation Conference, Singapore; Mar. 3, 2015; p. 1; Poster P2.93.
Cook et al.; "Trigeminal nerve stimulation in major depressive disorder: Acute outcomes in an open pilot study"; Epilepsy & Behavior; 2013; pp. 221-226; vol. 28.
Culic et al.; "Signatures of Depression in Non-Stationary Biometric Time Series"; Computational Intelligence and Neuroscience; 2009; pp. 1-7 plus one end page; Hindawi Publishing Corporation.
Djupesland et al.; "Impedance Changes Elicited by Electrocutaneous Stimulation"; Audiology; 1977; pp. 355-364.
Edwards, Luke; "Jabra Pulse review: Heart-rate monitor earphones put a virtual personal trainer in your ears"; Pocket-lint; Oct. 27, 2014; pp. 1-8; located at http://www.pocket-lint.com/review/131340-jabra-pulse-review-heart-rate-monitor-earphones-put-a-virtual-personal-trainer-in-your-ears.
Ellrich et al.; "Peripheral Nerve Stimulation Inhibits Nociceptive Processing: An Electrophysiological Study in Healthy Volunteers"; Neuromodulation; 2005; pp. 225-232; vol. 8, No. 4; International Neuromodulation Society.
Ellrich, Jens; "Transcutaneous Vagus Nerve Stimulation"; European Neurological Review, Epilepsy; 2011; pp. 254-256; Touch Briefings.
Fakhir et al.; "Face Recognition Based on Features Measurement Technique"; UKSim-AMSS 8th European Modelling Symposium; 2014; pp. 158-162.
Fang et al.; "Transcutaneous Vagus Nerve Stimulation Modulates Default Mode Network in Major Depressive Disorder"; Biological

(56) References Cited

OTHER PUBLICATIONS

Psychiatry, Archival Report; Feb. 15, 2016 and available online Apr. 2, 2015; pp. 266-273; Elsevier Inc. on behalf of Society of Biological Psychiatry.

Fluke Corporation; "Fluke Industrial/Electrical Thermal Imagers, Models: Ti25 and Ti10"; 2009-2011; pp. 1-3.

He et al.; "Auricular Acupuncture and Vagal Regulation"; Evidence-Based Complementary and Alternative Medicine; 2012; pp. 1-6; Hindawi Publishing Corporation.

Johnson et al.; "The effects of auricular transcutaneous electrical nerve stimulation (TENS) on experimental pain threshold and autonomic function in healthy subjects"; Pain; 1991; pp. 337-342; vol. 46, No. 3 (Abstract only).

Julian et al.; "The Effects of Mechanical Stimulation on Some Electrical Properties of Axons"; The Journal of General Physiology; Nov. 1, 1962; pp. 297-313; vol. 46.

Kalyani et al.; "Neurohemodynamic correlates of 'OM' chanting. A pilot functional magnetic resonance imaging study"; International Journal of Yoga; Jan.-Jun. 2011; pp. 3-6; vol. 4, No. 1.

Karavidas, Maria; "Heart Rate Variability Biofeedback for Major Depression"; Biofeedback; Spring 2008; pp. 18-21; vol. 36, No. 1; Association for Applied Psychophysiology & Biofeedback.

Kataria et al.; "A Survey of Automated Biometric Authentication Techniques"; Nirma University International Conference on Engineering (NUiCONE); 2013; pp. 1-6; IEEE.

Kessel et al., "The Relationship between Body and Ambient Temperature and Corneal Temperature"; Investigative Ophthalmology & Visual Science; Dec. 2010; pp. 6593-6597; vol. 51, No. 12, Association for Research in Vision and Ophthalmology.

Kim et al.; "Epidermal Electronics"; Science; Aug. 12, 2011; pp. 838-843 plus two pages; vol. 333.

Kim et al.; "Flexible and Stretchable Electronics for Biointegrated Devices"; Annu Rev. Biomed. Eng.; 2012; pp. 113-128 plus two pages; vol. 14.

Komarnitki et al.; "Clinical anatomy of the auriculotemporal nerve in the area of the infratemporal fossa"; Folia Morphol (Warsz); Aug. 2012; pp. 187-193; vol. 71, No. 3 (Abstract only).

Legon et al.; "Pulsed Ultrasound Differentially Stimulates Somatosensory Circuits in Humans as Indicated by EEG and fMRI"; PLOS One; Dec. 2012; pp. 1-14; vol. 7, Issue 12, No. e51177.

Leistritz et al.; "Connectivity Analysis of Somato-sensory Evoked Potentials in Patients with Major Depression"; Methods Inf. Med.; 2010; pp. 484-491; Schattauer.

Lu et al.; "Limitations of oximetry to measure heart rate variability measures"; Cardiovascular Eng.; Sep. 2009; pp. 119-125; vol. 9, No. 3 (Abstract only).

Medical Xpress; "New disposable biosensor may help physicians determine which patients can safely be fed following surgery"; Aug. 7, 2014; pp. 1-4; located at http://medicalxpress.com/news/2014-08-disposable-biosensor-physicians-patients-safely.html Meijerman et al.; "Cross-sectional anthropometric study of the external ear"; Journal of Forensic Sciences; Mar. 2007; pp. 286-293; vol. 52, No. 2 (Abstract only).

Meijerman et al.; "Cross-Sectional Anthropometric Study of the External Ear, Chapter 5"; 2006; pp. 79-98; located at https://openaccess.leidenuniv.nl/bitstream/handle/1887/4292/Chapter+5.PDF;jsessionid=983F196AE54E664EBBF070731EAA0A14?sequence=28.

Napadow et al.; "Evoked Pain Analgesia in Chronic Pelvic Pain Patients using Respiratory-gated Auricular Vagal Afferent Nerve Stimulation"; Pain Med.; Jun. 2012; pp. 777-789; vol. 13, No. 6.

National Instituie of Mental Health; "Major Depression Among Adults"; printed on Feb. 4, 2016; pp. 1-2; located at http://www.nimh.nih.gov/health/statistics/prevalence/major-depression-among-adults.shtml.

Netter, Frank H.; Atlas of Human Anatomy, Third Edition; 2002; 612 pages; Elsevier Health Sciences Division.

Neurosigma, Inc.; "eTNS Therapy: How eTNS Works as an Alternative to Vagus Nerve Stimulation (VNS)"; printed on Jul. 30, 2014; pp. 1-3; located at http://www.monarch-etns.com/etns-therapy.

Nguyen et al.; "Heart-Rate Monitoring Control System Using Photoplethysmography (PPG), Senior Project, Electrical Engineering Department"; California Polytechnic State University, San Luis Obispo; 2011; pp. 1-42 plus 5 pages.

Nutt, DJ; "Relationship of neurotransmitters to the symptoms of major depressive disorder"; J. Clin. Psychiatry; 2008; pp. 4-7; vol. 69, Supp E1 (Abstract only).

Oliveri et al. "Effects of Auricular Transcutaneous Electrical Nerve Stimulation on Experimental Pain Threshold"; Physical Therapy; Jan. 1986; pp. 12-16, plus Errata and 2 pages; vol. 66, No. 1.

O'Rahilly et al.; "Chapter 44: The Ear"; Basic Human Anatomy; 2008; pp. 1-10; located at https://www.dartmouth.edu/~humananatomy/part_8/chapter_44.html.

PCT International Search Report; International App. No. PCT/US2016/023905; dated Jul. 4, 2016; pp. 1-5.

Phys.org; "The goose bump sensor: A step toward direct detection of human emotional states"; Jun. 24, 2014; pp. 1-2; located at http://phys.org/news/2014-06-goose-sense-human-emotional-states.html.

Ristić et al.; "Analgesic and antinociceptive effects of peripheral nerve neurostimulation in an advanced human experimental model"; European Journal of Pain; 2008; pp. 480-490; vol. 12; Elsevier Ltd.

Rong et al.; "Transcutaneous vagus nerve stimulation for the treatment of depression: a study protocol for a double blinded randomized clinical trial"; BMC Complementary and Alternative Medicine; 2012; pp. 1-6.

Salvatore et al.; "Wafer-scale design of lightweight and transparent electronics that wraps around hairs"; Nature Communications; 2014; pp. 1-8; Macmillan Publishers Limited.

Samani et al.; "An Arbitrary Waveform Wearable Neuro-stimulator System for Neurophysiology Research on Freely Behaving Animals"; Journal of Medical Signals and Sensors; Apr.-Jun. 2014; pp. 94-102 vol. 4. No. 2.

Science Daily; "'Tickling' your ear could be good for your heart"; Aug. 19, 2014; pp. 1-2; located at: http://www.sciencedaily.com/releases/2014/08/140819200211.htm.

Sciencedaily; "New non-invasive form of vagus nerve stimulation works to treat depression"; Feb. 4, 2016; pp. 1-6; located at http://www.sciencedaily.com/releases/2016/02/160204111728.htm.

Seeing Machines; "faceLAB 5" Specification Sheet; 2012; pp. 1.

Shastri et al.; "Imaging Facial Signs of Neurophysiological Responses"; IEEE Transactions on Biomedical Engineering; Feb. 2009; pp. 477-484; vol. 56, No. 2.

Shiffman et al.; "Ecological Momentary Assessment"; Annual Review of Clinical Psychology; Apr. 2008 (First Published Online Nov. 28, 2007); pp. 1-32; vol. 4.

Straube et al.; "Treatment of chronic migraine with transcutaneous stimulation of the auricular branch of the vagal nerve (auricular t-VNS): a randomized, monocentric clinical trial"; The Journal of Headache Pain; 2015; pp. 1-9; vol. 16, No. 63.

Su et al.; "A simple approach to facial expression recognition"; Proceedings of the 2007 WSEAS International Conference on Computer Engineering and Applications, Queensland, Australia; Jan. 17-19, 2007; pp. 456-461.

Su et al.; "Mechanics of finger-tip electronics"; Journal of Applied Physics; 2013; pp. 164511-1 through 164511-6 plus one page; vol. 114.

Sullivan et al.; "A Morphometric Study of the External Ear: Age and Sex Related Differences"; Jul. 26, 2010; pp. 1-12; located at: http://www.drsullivan.com/scientific-publications/a-morphometric-study-of-the-external-ear-age-and-sex-related-differences/.

Tekdemir et al.; "A clinic-anatomic study of the auricular branch of the vagus nerve and Arnold's ear-cough reflex"; Surg. Radiol. Anat.; 1998; pp. 253-257; vol. 20, No. 4 (Abstract only).

Tyler et al.; "Remote Excitation of Neuronal Circuits Using Low-Intensity, Low-Frequency Ultrasound"; PLoS One; Oct. 2008; pp. 1-11: vol. 3, Issue 10, No. e3511.

Van Leusden et al.; "Transcutaneous Vagal Nerve Stimulation (tVNS): a new neuromodulation tool in healthy humans?", Frontiers in Psychology; Feb. 10, 2015; pp. 1-4; vol. 6, Article 102.

(56) References Cited

OTHER PUBLICATIONS

Webb et al.; "Ultrathin conformal devices for precise and continuous thermal characterization of human skin"; Nature Materials; Oct. 2013; pp. 938-944, one page (Erratum), and pp. 1-27 (Supplementary Information); vol. 12; Macmillan Publishers Limited.
Weintraub, Arlene; "Brain-Altering Devices May Supplant Drugs—and Pharma Is Ok With That"; Forbes.com; Feb. 24, 2015; pp. 1-4; located at http://www.forbes.com/sites/arleneweibtraub/2015/02/24/brain-altering-devices-may-supplant-drugs-and-pharma-is-ok-with-that/.
Wheeler et al.; "Face Recognition at a Distance System for Surveillance Applications"; Fourth IEEE International Conference on Biometrics: Theory Applications and Systems (BTAS); 2010; pp. 1-8; IEEE.
Wilson-Pauwels et al.; "Cranial Nerves in Health and Disease, Second Edition"; 2002; pp. i-ix, 1-245, cover, and back cover; BC Decker Inc.; Hamilton, Ontario, Canada.
Wong and Salleo, Eds.; "Flexible Electronics: Materials and Applications"; 2009; pp. i-xviii and pp. 1-462; Springer Science+Business Media, LLC.
Wu et al.; "Eulerian Video Magnification for Revealing Subtle Changes in the World"; CM Transactions on Graphics (TOG)—SIGGRAPH 2012 Conference Proceedings; Jul. 2012; pp. 1-8; Article No. 65; vol. 31, Issue 4.
Xu et al.; "Soft Microfluidic Assemblies of Sensors, Circuits, and Radios for the Skin"; Science; Apr. 4, 2014; pp. 70-74 and one page; vol. 344.
Yap et al.; "A Short Review of Methods for Face Detection and Multifractal Analysis"; International Conference on CyberWorlds; 2009; pp. 231-236.
U.S. Appl. No. 15/340,217, Goodall et al.
U.S. Appl. No. 15/340,145, Goodall et al.
U.S. Appl. No. 15/291,358, Hyde et al.
U.S. Appl. No. 15/996,621, Goodall et al.
U.S. Appl. No. 15/673,087, Goodall et al.
Hill, Simon; "Will a Magnet Destroy a Smartphone or Hard Drive?"; Digital Trends; May 31, 2015; pp. 1-7; located at https://www.digitaltrends.com/mobile/how-magnets-really-affect-phones-hard-drives/.
Supermagnete; "Can magnets damage electric devices?"; printed on Jul. 19, 2017; pp. 1-5; located at https://www.supermagnete.de/eng/faq/What-is-the-safe-distance-that-I-need-to-keep-to-my-devices.
U.S. Appl. No. 16/058,174, Goodall et al.
Amazon.com; "SleepPro™ Snore Stopper Wristband—Smart Anti Snoring Biofeedback Sensor Nasal Tracker Anti-Snore . . . "; printed on Aug. 7, 2018; pp. 1-5; located at: https:www.amazon.com/SleepProTM-Snore-Stopper-Wristband-Biofeedback/dp/B07CS4MDVW/ref=sr_1_4_a_it?ie=UTF8&qid=1533675358&sr=8-4&keywords=snore+stopper+wristband&dpID=513KnJCQPWL&preST=_SY300_QL70_&dpSrc=srch.
Askin et al.; "Low dose high frequency ultrasound therapy for stellate ganglion blockade in complex regional pain syndrome type I: a randomised placebo controlled trial"; Int J Clin Exp Med; 2014; pp. 5603-5611; vol. 7, No. 12.
Clover, Juli; "Popular Sleep Cycle iPhone App Expands to Apple Watch With 'Snore Stopper' and Haptic Wake Up Features"; Apr. 19, 2018; pp. 1-9; located at https://www.macrumors.com/2018/04/19/sleep-cycle-apple-watch-snore/.
Daulatzai, Mak Adam; "Role of Sensory Stimulation in Amelioration of Obstructive Sleep Apnea"; Sleep Disorders; 2011; 12 pages; vol. 2011, Article ID 596879.
Howland, Robert H.; "Vagus Nerve Stimulation"; Curr Behav Neurosci Rep.; Jun. 2014; pp. 64-73; vol. 1, No. 2.
Juan et al.; "Vagus Nerve Modulation Using Focused Pulsed Ultrasound: Potential Applications and Preliminary Observations in a Rat"; Int J Imaging Syst Technol.; Mar. 2014; pp. 67-71; vol. 24, No. 1.
Smith et al.; "Stochastic Resonance Effects on Apnea, Bradycardia, and Oxygenation: A Randomized Controlled Trial"; Pediatrics; Dec. 2015; ten pages; vol. 136, No. 6.
Watson, Tim; "Transcuatneous Electrical Nerve Stimulation (TENS)"; printed on Aug. 7, 2018; pp. 1-17; located at: http://www.electrotherapy.org/modality/transcutaneous-electrical-nerve-stimulation-tens.
Blizzard Entertainment: "Starcraft Manual"; 1998; pp. 1-98.
Youtube.com; Screen Capture from Youtube video clip entitled "Grr . . . VS H.O.T-Forever@2000 Hanaro OSL Finals Game 1"; uploaded Oct. 8, 2006 by Mickey Toss; 1 page; located at https://www.youtube.com/watch?v=FO5fH3ifIQA.
Youtube.com; Screen Capture from Youtube video clip entitled "Starcraft Campaign Episode 1—Terran Original"; uploaded Nov. 19, 2011 by ItellYaHuat; 1 page; located at https://www.youtube.com/watch?v=jr2MDSdxcsA.
European Patent Office, Supplementary European Search Report, Pursuant to Rule 62 EPC; App. No. EP 16773778; dated Sep. 28, 2018 (received by our Agent on Oct. 5, 2018); pp. 1-6.

\* cited by examiner

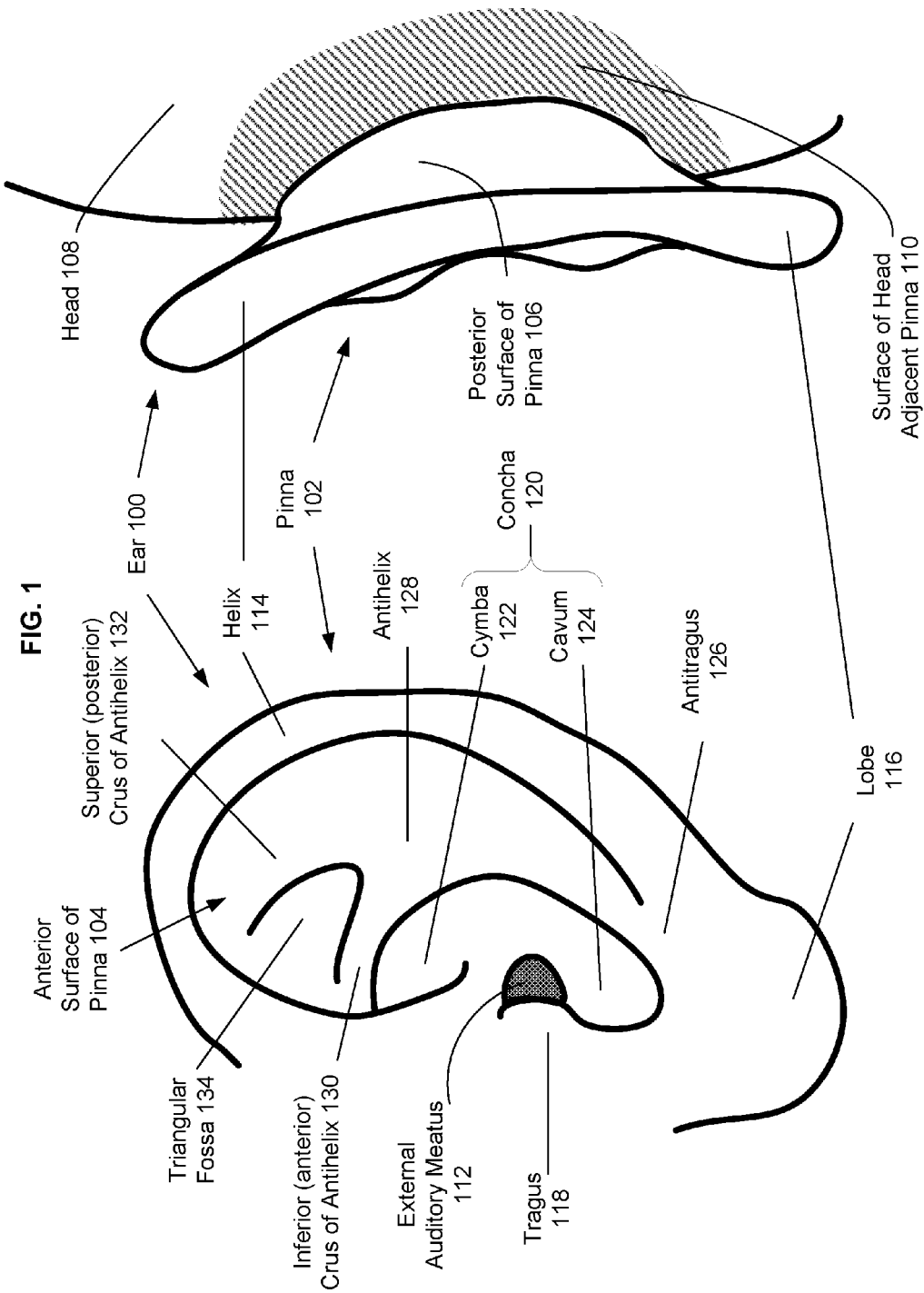

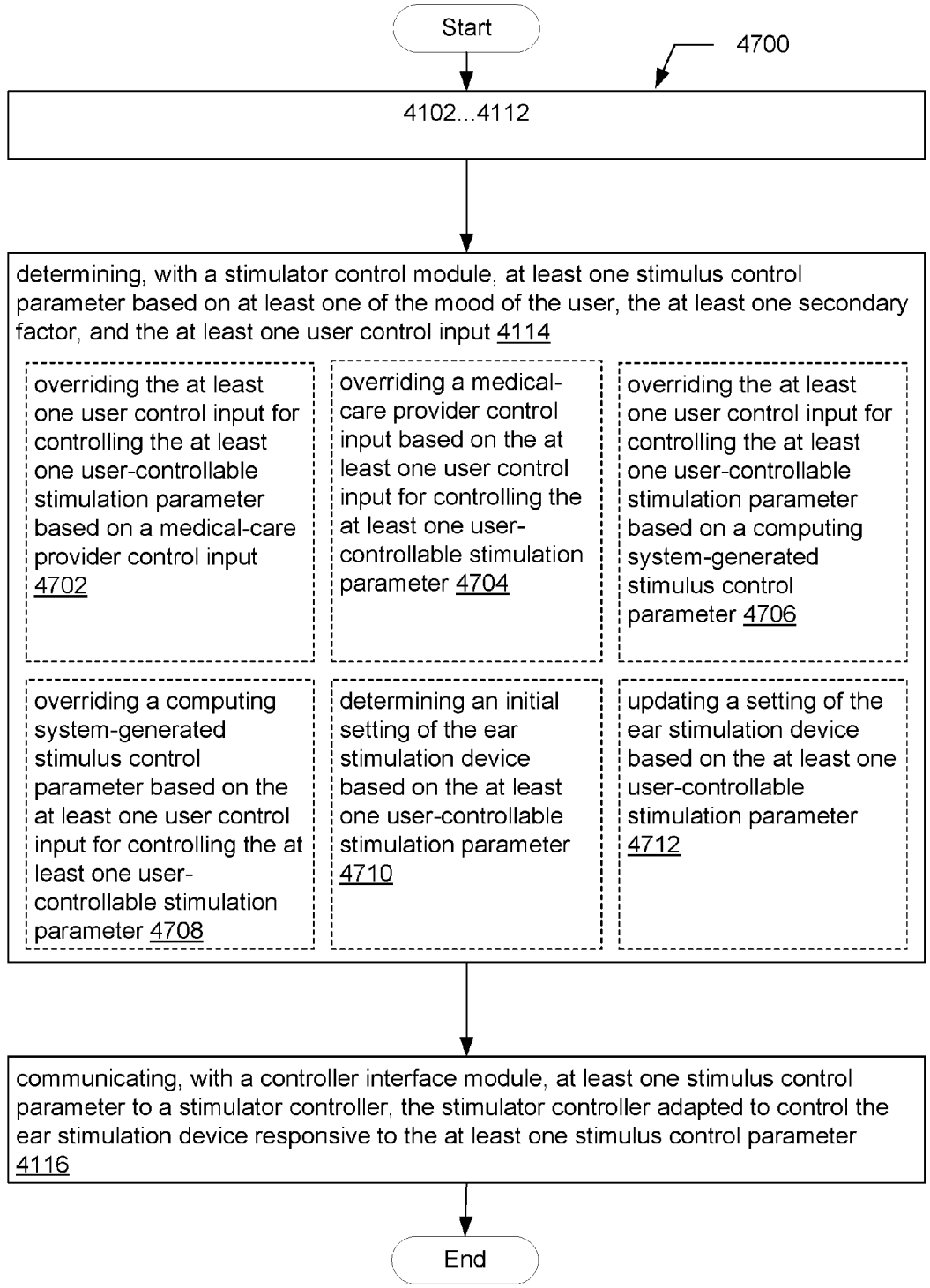

CONTROLLING EAR STIMULATION IN RESPONSE TO IMAGE ANALYSIS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation-in-part of U.S. patent application Ser. No. 14/670,504, entitled EAR STIMULATION WITH NEURAL FEEDBACK SENSING, naming RODERICK A. HYDE, MURIEL Y. ISHIKAWA, JORDIN T. KARE, ERIC C. LEUTHARDT, MARK A. MALAMUD, STEPHEN L. MALASKA, NATHAN P. MYHRVOLD, ELIZABETH A. SWEENEY, CLARENCE T. TEGREENE, CHARLES WHITMER, LOWELL L. WOOD, JR., AND VICTORIA Y. H. WOOD, as inventors, filed 27 Mar. 2015, which is currently co-pending or is an application of which a currently co-pending application is entitled to the benefit of the filing date.

The present application constitutes a continuation-in-part of U.S. patent application Ser. No. 14/670,537, entitled VIBRATORY EAR STIMULATION SYSTEM AND METHOD, naming RODERICK A. HYDE, MURIEL Y. ISHIKAWA, JORDIN T. KARE, ERIC C. LEUTHARDT, MARK A. MALAMUD, STEPHEN L. MALASKA, NATHAN P. MYHRVOLD, ELIZABETH A. SWEENEY, CLARENCE T. TEGREENE, CHARLES WHITMER, LOWELL L. WOOD, JR., AND VICTORIA Y. H. WOOD, as inventors, filed 27 Mar. 2015, which is currently co-pending or is an application of which a currently co-pending application is entitled to the benefit of the filing date.

The present application constitutes a continuation-in-part of U.S. patent application Ser. No. 14/670,560, entitled METHOD AND SYSTEM FOR CONTROLLING EAR STIMULATION, naming RODERICK A. HYDE, MURIEL Y. ISHIKAWA, JORDIN T. KARE, ERIC C. LEUTHARDT, MARK A. MALAMUD, STEPHEN L. MALASKA, NATHAN P. MYHRVOLD, ELIZABETH A. SWEENEY, CLARENCE T. TEGREENE, CHARLES WHITMER, LOWELL L. WOOD, JR., AND VICTORIA Y. H. WOOD, as inventors, filed 27 Mar. 2015, which is currently co-pending or is an application of which a currently co-pending application is entitled to the benefit of the filing date.

The present application constitutes a continuation-in-part of U.S. patent application Ser. No. 14/670,582, entitled USER INTERFACE METHOD AND SYSTEM FOR EAR STIMULATION, naming RODERICK A. HYDE, MURIEL Y. ISHIKAWA, JORDIN T. KARE, ERIC C. LEUTHARDT, MARK A. MALAMUD, STEPHEN L. MALASKA, NATHAN P. MYHRVOLD, ELIZABETH A. SWEENEY, CLARENCE T. TEGREENE, CHARLES WHITMER, LOWELL L. WOOD, JR., AND VICTORIA Y. H. WOOD, as inventors, filed 27 Mar. 2015, which is currently co-pending or is an application of which a currently co-pending application is entitled to the benefit of the filing date.

The present application constitutes a continuation-in-part of U.S. patent application Ser. No. 14/670,620, entitled NEURAL STIMULATION METHOD AND SYSTEM WITH AUDIO OUTPUT, naming RODERICK A. HYDE, MURIEL Y. ISHIKAWA, JORDIN T. KARE, ERIC C. LEUTHARDT, MARK A. MALAMUD, STEPHEN L. MALASKA, NATHAN P. MYHRVOLD, ELIZABETH A. SWEENEY, CLARENCE T. TEGREENE, CHARLES WHITMER, LOWELL L. WOOD, JR., AND VICTORIA Y. H. WOOD, as inventors, filed 27 Mar. 2015, which is currently co-pending or is an application of which a currently co-pending application is entitled to the benefit of the filing date.

The present application constitutes a continuation-in-part of U.S. patent application Ser. No. 14/670,656, entitled RECOMMENDATION METHOD AND SYSTEM FOR TREATMENTS INCLUDING EAR STIMULATION, naming RODERICK A. HYDE, MURIEL Y. ISHIKAWA, JORDIN T. KARE, ERIC C. LEUTHARDT, MARK A. MALAMUD, STEPHEN L. MALASKA, NATHAN P. MYHRVOLD, ELIZABETH A. SWEENEY, CLARENCE T. TEGREENE, CHARLES WHITMER, LOWELL L. WOOD, JR., AND VICTORIA Y. H. WOOD, as inventors, filed 27 Mar. 2015, which is currently co-pending or is an application of which a currently co-pending application is entitled to the benefit of the filing date.

The present application constitutes a continuation-in-part of U.S. patent application Ser. No. 15/291,358, entitled NERVE STIMULATION SYSTEM AND RELATED CONTROLLER, naming RODERICK A. HYDE, MURIEL Y. ISHIKAWA, JORDIN T. KARE, ERIC C. LEUTHARDT, MARK A. MALAMUD, STEPHEN L. MALASKA, NATHAN P. MYHRVOLD, BRITTANY SCHEID, ELIZABETH A. SWEENEY, CLARENCE T. TEGREENE, CHARLES WHITMER, LOWELL L. WOOD, JR., AND VICTORIA Y. H. WOOD, as inventors, filed 12 Oct. 2016, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a neural stimulation system includes, but is not limited to, a neural signal sensor adapted to sense a neural signal from a subject, the neural signal indicative of a physiological status of the subject, a neural stimulator adapted to produce a stimulus responsive to the sensed neural signal, the stimulus configured to activate at least one sensory nerve fiber innervating at least a portion of a pinna of the subject, and a securing member configured to secure the neural stimulator to the pinna. In addition to the foregoing, other system aspects are described in the claims, drawings, and text forming a part of the disclosure set forth herein.

In an aspect, a method includes, but is not limited to, sensing with a neural signal sensor a neural signal indicative of a physiological status of a subject, the neural signal sensor located in or on a portion of a body of the subject, determining with signal analysis circuitry at least one parameter of the sensed neural signal, and delivering a neural stimulus with a neural stimulation device worn on a pinna of the subject responsive to the sensed neural signal, wherein the neural stimulus is configured to modulate the activity of at least one sensory nerve fiber innervating at least a portion of the pinna of the subject. In addition to the foregoing, other method aspects are described in the claims, drawings, and text forming a part of the disclosure set forth herein.

A wearable neural stimulation device includes, but is not limited to, a vibratory mechanical stimulator adapted to produce a vibratory stimulus of sufficient frequency and amplitude to modulate the activity of at least one mechanoreceptor with a receptive field on at least a portion of a pinna of a subject, and a securing member configured to secure the vibratory mechanical stimulator to the pinna. In addition to the foregoing, other device aspects are described in the claims, drawings, and text forming a part of the disclosure set forth herein.

In an aspect, a method includes, but is not limited to, delivering a vibratory mechanical stimulus to at least a portion of a pinna of a subject with a neural stimulation device worn on the pinna of the subject, wherein the vibratory mechanical stimulus is of sufficient frequency and amplitude to modulate the activity of at least one mechanoreceptor with a receptive field on the at least a portion of the pinna. In addition to the foregoing, other method aspects are described in the claims, drawings, and text forming a part of the disclosure set forth herein.

In an aspect, a neural stimulation system includes, but is not limited to, a wearable neural stimulation device and a personal computing device, the wearable neural stimulation device including a neural stimulator adapted to produce a stimulus for activating at least one sensory nerve fiber innervating at least a portion of a pinna of a subject, a securing member configured to secure the neural stimulator to the pinna, control circuitry incorporated into the wearable neural stimulation device for controlling operation of the neural stimulator, and first communication circuitry incorporated into the wearable neural stimulation device and operatively connected to the control circuitry, the first communication circuitry configured for at least one of sending a signal to and receiving a signal from a personal computing device; and the personal computing device including a user interface for at least one of presenting information to and receiving information from a user, control circuitry operatively connected to the user interface, second communication circuitry configured for at least one of sending a signal to and receiving a signal from the first communication circuitry, and instructions that when executed on the personal computing device cause the personal computing device to perform at least one of sending a signal to and receiving a signal from the wearable neural stimulation device via the second communication circuitry. In addition to the foregoing, other system aspects are described in the claims, drawings, and text forming a part of the disclosure set forth herein.

In an aspect, a system includes, but is not limited to, a personal computing device comprising circuitry for receiving a neural activity signal, the neural activity signal indicative of a physiological status of a subject, circuitry for determining a neural stimulus control signal based at least in part on the neural activity signal, and circuitry for outputting the neural stimulus control signal to a neural stimulation device including an external neural stimulator configured to be carried on a pinna of the subject, wherein the neural stimulus control signal is configured to control delivery of a neural stimulus by the external neural stimulator, the neural stimulus configured to activate at least one sensory nerve fiber innervating at least a portion of the pinna. In addition to the foregoing, other system aspects are described in the claims, drawings, and text forming a part of the disclosure set forth herein.

In an aspect, a method includes, but is not limited to, receiving a neural activity signal at a personal computing device, the neural activity signal indicative of a physiological status of a subject, determining a neural stimulus control signal based at least in part on the neural activity signal, and outputting the neural stimulus control signal from the personal computing device to a neural stimulation device including an external neural stimulator configured to be carried on a pinna of the subject, wherein the neural stimulus control signal is configured to control delivery of a neural stimulus by the external neural stimulator, the neural stimulus configured to activate at least one sensory nerve fiber innervating at least a portion of the pinna. In addition to the foregoing, other method aspects are described in the claims, drawings, and text forming a part of the disclosure set forth herein.

In an aspect, a computer program product includes, but is not limited to, a non-transitory signal-bearing medium bearing one or more instructions for receiving a neural activity signal, the neural activity signal indicative of a physiological status of a subject, one or more instructions for determining a neural stimulus control signal based at least in part on the neural activity signal, and one or more instructions for outputting the neural stimulus control signal to a neural stimulation device including an external neural stimulator configured to be carried on a pinna of the subject, wherein the neural stimulus control signal is configured to control delivery of a neural stimulus by the external neural stimulator, the neural stimulus configured to activate at least one sensory nerve fiber innervating at least a portion of the pinna. In addition to the foregoing, other aspects of a computer program product are described in the claims, drawings, and text forming a part of the disclosure set forth herein.

In an aspect, a method includes, but is not limited to receiving a physiological activity signal at a personal computing device, the physiological activity signal indicative of a physiological status of a subject, determining a neural stimulus control signal based at least in part on the physiological activity signal, outputting the neural stimulus control signal from the personal computing device to a neural stimulation device including an external neural stimulator configured to be carried on a pinna of the subject, wherein the neural stimulus control signal is configured to control delivery of a neural stimulus by the external neural stimulator, the neural stimulus configured to activate at least one sensory nerve fiber innervating at least a portion of the pinna, and presenting information to the subject via a user interface. In addition to the foregoing, other method aspects are described in the claims, drawings, and text forming a part of the disclosure set forth herein.

In an aspect, a system includes, but is not limited to a personal computing device including circuitry for receiving a physiological activity signal at a personal computing device, the physiological activity signal indicative of a physiological status of a subject, circuitry for determining a neural stimulus control signal based at least in part on the physiological activity signal, the neural stimulus control signal is configured to control delivery of a neural stimulus by the external neural stimulator, the neural stimulus configured to activate at least one sensory nerve fiber innervating at least a portion of the pinna, circuitry for outputting the neural stimulus control signal from the personal computing device to a neural stimulation device including an external neural stimulator configured to be carried on a pinna of the subject, and circuitry for presenting information to the subject via a user interface. In addition to the foregoing, other personal computing device aspects are described in the claims, drawings, and text forming a part of the disclosure set forth herein.

In an aspect, a computer program product includes, but is not limited to, a non-transitory signal-bearing medium bearing one or more instructions for receiving a physiological activity signal, the physiological activity signal indicative of a physiological status of a subject, one or more instructions for determining a neural stimulus control signal based at least in part on the physiological activity signal, one or more instructions for outputting the neural stimulus control signal to a neural stimulation device including an external neural stimulator configured to be carried on an ear of a subject, wherein the neural stimulus control signal is configured to control delivery of a neural stimulus by the external neural stimulator, the neural stimulus configured to activate at least one sensory nerve fiber innervating at least a portion of the pinna, and one or more instructions for presenting information to the subject via a user interface. In addition to the foregoing, other computer program product aspects are described in the claims, drawings, and text forming a part of the disclosure set forth herein.

In an aspect, a system includes, but is not limited to a personal computing device including circuitry for receiving a physiological activity signal at a personal computing device, the physiological activity signal indicative of a physiological status of a subject, circuitry for determining a neural stimulus control signal based at least in part on the physiological activity signal, circuitry for outputting the neural stimulus control signal from the personal computing device to a neural stimulation device including an external neural stimulator configured to be carried on a pinna of the subject, wherein the neural stimulus control signal is configured to control delivery of a neural stimulus by the external neural stimulator, the neural stimulus configured to activate at least one sensory nerve fiber innervating at least a portion of the pinna, and circuitry for outputting an audio output signal via an audio output of the personal computing device. In addition to the foregoing, other system aspects are described in the claims, drawings, and text forming a part of the disclosure set forth herein.

In an aspect, a method includes, but is not limited to, receiving a physiological activity signal at a personal computing device, the physiological activity signal indicative of a physiological status of a subject, determining a neural stimulus control signal based at least in part on the physiological activity signal, outputting the neural stimulus control signal from the personal computing device to a neural stimulation device including an external neural stimulator configured to be carried on a pinna of the subject, wherein the neural stimulus control signal is configured to control delivery of a neural stimulus by the external neural stimulator, the neural stimulus configured to activate at least one sensory nerve fiber innervating at least a portion of the pinna, and outputting an audio output signal via an audio output of the personal computing device. In addition to the foregoing, other method aspects are described in the claims, drawings, and text forming a part of the disclosure set forth herein.

In an aspect, a computer program product includes, but is not limited to, a non-transitory signal-bearing medium bearing one or more instructions for receiving a physiological activity signal at a personal computing device, the physiological activity signal indicative of a physiological status of a subject, one or more instructions for determining a neural stimulus control signal based at least in part on the physiological activity signal, one or more instructions for outputting the neural stimulus control signal from the personal computing device to a neural stimulation device including an external neural stimulator configured to be carried on a pinna of the subject, wherein the neural stimulus control signal is configured to control delivery of a neural stimulus by the external neural stimulator, the neural stimulus configured to activate at least one sensory nerve fiber innervating at least a portion of the pinna, and one or more instructions for outputting an audio output signal via an audio output of the personal computing device. In addition to the foregoing, other computer program product aspects are described in the claims, drawings, and text forming a part of the disclosure set forth herein.

In an aspect, a method includes, but is not limited to, determining a vibratory stimulus control signal with stimulation control circuitry in a personal computing device, and outputting the vibratory stimulus control signal from the personal computing device to a wearable mechanical stimulation device including a vibratory mechanical stimulator configured to be carried on a pinna of a subject, wherein the vibratory stimulus control signal is configured to control delivery of a vibratory stimulus by the vibratory mechanical stimulator, the vibratory stimulus configured to activate at least one mechanoreceptor with a receptive field on at least a portion of the pinna. In addition to the foregoing, other method aspects are described in the claims, drawings, and text forming a part of the disclosure set forth herein.

In an aspect, a system includes, but is not limited to, a personal computing device including circuitry for determining a vibratory stimulus control signal, and circuitry for outputting the vibratory stimulus control signal to a wearable mechanical stimulation device including a vibratory mechanical stimulator configured to be carried on a pinna of a subject, wherein the vibratory stimulus control signal is configured to control delivery of a vibratory stimulus by the vibratory mechanical stimulator, the vibratory stimulus configured to activate at least one mechanoreceptor with a receptive field on at least a portion of the pinna. In addition to the foregoing, other system aspects are described in the claims, drawings, and text forming a part of the disclosure set forth herein.

In an aspect, a computer program product includes, but is not limited to, a non-transitory signal-bearing medium bearing one or more instructions for determining a vibratory stimulus control signal configured to control delivery of a vibratory stimulus by a vibratory mechanical stimulator, the vibratory stimulus configured to activate at least one mechanoreceptor with a receptive field on at least a portion of a pinna of a subject, and one or more instructions for outputting the vibratory stimulus control signal to a wearable mechanical stimulation device including the least one vibratory mechanical stimulator. In addition to the foregoing, other computer program product aspects are described in the claims, drawings, and text forming a part of the disclosure set forth herein.

In an aspect, a method includes, but is not limited to, receiving identifying information at a computing system, the identifying information identifying at least one of a subject and a neural stimulation device associated with the subject, the neural stimulation device configured to be carried on an ear of a subject and including an external neural stimulator, and transmitting a recommendation relating to a treatment regimen from the computing system to a personal computing device used by the subject, the treatment regimen including delivery of a neural stimulus to the subject with the external neural stimulator, the neural stimulus configured to activate at least one sensory nerve fiber innervating skin on or in the vicinity of the ear of the subject. In addition to the foregoing, other method aspects are described in the claims, drawings, and text forming a part of the disclosure set forth herein.

In an aspect, a system includes, but is not limited to, circuitry for receiving identifying information identifying at least one of a subject and a neural stimulation device associated with the subject, the neural stimulation device configured to be carried on an ear of a subject and including an external neural stimulator, and circuitry for providing a recommendation relating to a treatment regimen to the subject, the treatment regimen including delivery of a neural stimulus to the subject with the external neural stimulator, the neural stimulus configured to activate at least one sensory nerve fiber innervating skin on or in the vicinity of the ear of the subject. In addition to the foregoing, other system aspects are described in the claims, drawings, and text forming a part of the disclosure set forth herein.

In an aspect, a computer program product includes, but is not limited to, a non-transitory signal-bearing medium bearing one or more instructions for receiving identifying information identifying at least one of a subject and a neural stimulation device associated with the subject, the neural stimulation device configured to be carried on an ear of a subject and including an external neural stimulator, and one or more instructions for providing a recommendation relating to a treatment regimen to the subject, the treatment regimen including delivery of a neural stimulus to the subject with the external neural stimulator, the neural stimulus configured to activate at least one sensory nerve fiber innervating skin on or in the vicinity of the ear of the subject. In addition to the foregoing, other computer program product aspects are described in the claims, drawings, and text forming a part of the disclosure set forth herein.

In an aspect, a method of controlling an ear stimulation device with a personal computing device includes, but is not limited to, capturing, with image capture circuitry on the personal computing device, via a user-facing camera associated with the personal computing device, an image of a user of the personal computing device; processing the image, using image processing circuitry on the personal computing device, to determine at least one parameter; and controlling, with neural stimulus control signal determination circuitry on the personal computing device, based at least in part on the at least one parameter, delivery of a stimulus to at least one nerve innervating an ear of the user with the ear stimulation device. In a further aspect, the method includes processing the image, using the image processing circuitry, to determine the presence of at least one earpiece of the ear stimulation device located at an ear of the user; the ear of the user at which the at least one earpiece is located, the ear selected from a right ear of the user and a left ear of the user; and at least one attribute of the at least one earpiece indicative of usability of the at least one earpiece with one of the left or the right ear of the user; determining, using application software on the personal computing device, the ear at which the earpiece is usable, based on the at least one attribute of the at least one earpiece; determining, using application software on the personal computing device, whether the ear at which the at least one earpiece is located is the ear at which the earpiece is usable; and if the ear at which the at least one earpiece is located is not the ear at which the earpiece is usable, sending a control signal from the personal computing device to the ear stimulation device, under control of the neural stimulus control signal determination circuitry, to prevent delivery of a stimulus to the ear at which the earpiece is located via the earpiece. In addition to the foregoing, other method aspects are described in the claims, drawings, and text forming a part of the disclosure set forth herein.

In an aspect, an ear stimulation device control system includes, but is not limited to, a personal computing device; a user-facing camera associated with the personal computing device; image capture circuitry adapted to capture an image of a user of the personal computing device from the user-facing camera; image processing circuitry configured to process the image to determine at least one parameter; and neural stimulus control signal determination circuitry configured to control delivery of a stimulus to at least one nerve innervating an ear of the user with an ear stimulation device, based at least in part on the at least one parameter. In a further aspect, image processing circuitry includes an earpiece location module configured to process the image to determine the presence of at least one earpiece of the ear stimulation device located at an ear of the user; the ear of the user at which the at least one earpiece is located, the ear selected from a right ear of the user and a left ear of the user; and at least one attribute of the at least one earpiece indicative of usability of the at least one earpiece with one of the left or the right ear of the user; and the neural stimulus control signal determination circuitry is configured to determine the ear at which the earpiece is usable, based on the at least one attribute of the at least one earpiece; determine whether the ear at which the at least one earpiece is located is the ear at which the earpiece is usable; and if the ear at which the at least one earpiece is located is not the ear at which the earpiece is usable, send a control signal from the personal computing device to the ear stimulation device to prevent delivery of the stimulus to the a least one nerve innervating the ear of the user. In addition to the foregoing, other system aspects are described in the claims, drawings, and text forming a part of the disclosure set forth herein.

In an aspect, a method of controlling an ear stimulation device with a personal computing device includes, but is not limited to, detecting at electrical signal input circuitry, via at least one first electrode of an earpiece of an ear stimulation device, an electrical signal indicative of electrical contact of the at least one first electrode with the ear of a user of a personal computing device, wherein the at least one earpiece is operably connected to the personal computing device, and wherein the ear stimulation device is adapted to stimulate at least one nerve innervating the ear of the user of the personal computing device; determining, using contact determination circuitry on the personal computing device, whether the at least one first electrode is in good electrical contact with the ear of the user; if the at least one first electrode is not in good electrical contact with the ear of the user, sending a control signal from the personal computing device to the ear stimulation device, under control of neural stimulus control signal determination circuitry on the personal computing device, to prevent delivery via the earpiece of a stimulus to the ear at which the earpiece is located; and delivering, under control of notification circuitry on the personal computing device, a notification to the user relating to the status of the at least one first electrode. In addition to the foregoing, other method aspects are described in the claims, drawings, and text forming a part of the disclosure set forth herein.

In an aspect, an ear stimulation device control system includes, but is not limited to, a personal computing device configured to control delivery via an ear stimulation device of a stimulus to at least one nerve innervating an ear of a user of the personal computing device, the ear stimulation device including at least one first electrode, and the personal computing device including electrical signal circuitry adapted to receive an electrical signal indicative of electrical contact of the at least one first electrode with the ear of a user of the personal computing device; contact determination circuitry configured to determine whether the at least one first electrode is in good electrical contact with the ear of the user; neural stimulus control signal determination circuitry configured to send a control signal from the personal computing device to the ear stimulation device to prevent delivery of the stimulus if the at least one first electrode is not in good electrical contact with the ear of the user; and notification circuitry configured to deliver a notification to the user relating to the status of the at least one first electrode. In addition to the foregoing, other system aspects are described in the claims, drawings, and text forming a part of the disclosure set forth herein.

In an aspect, a personal computing device application for monitoring use of a nerve stimulation system by a user includes, but is not limited to, an audio delivery module adapted to control delivery of an audio signal from an audio signal source to an audio earpiece via an audio output of the personal computing device, the audio earpiece having associated therewith an ear stimulation device configured to stimulate a nerve innervating the ear of the user; a mood assessment module adapted to receive mood-related input from the user via a first input structure associated with the personal computing device; and assess a mood of the user based at least in part upon the mood-related input; a secondary factor input module adapted to receive at least one input relating to at least one secondary factor relating to the user via a second input structure associated with the personal computing device; user control module adapted to receive at least one user control input via a third input structure of the personal computing device, the user control input for controlling user-controllable stimulation parameters of the ear stimulation device; a stimulator control module adapted to determine at least one stimulus control parameter based on at least one of the mood of the user, the at least one secondary factor, and the at least one user control input; and a controller interface module for communicating the at least one stimulus control parameter to a stimulator controller adapted to control the ear stimulation device responsive to the at least one stimulus control parameter. In addition to the foregoing, other system aspects are described in the claims, drawings, and text forming a part of the disclosure set forth herein.

In an aspect, a method of controlling an ear stimulation device with a personal computing device includes, but is not limited to, receiving an audio signal at the personal computing device from an audio signal source; delivering the audio signal to an audio earpiece worn by a user via an audio output of the personal computing device, the audio earpiece having associated therewith an ear stimulation device configured to stimulate a nerve innervating the ear of the user; receiving with a mood assessment module, via a first input structure associated with the personal computing device, a mood-related input from the user; assessing, with the mood assessment module, a mood of the user based at least in part upon the mood-related input; receiving with a secondary factor input module, via a second input structure associated with the personal computing device, at least one input relating to at least one secondary factor relating to the user; receiving with a user control module, via a third input structure associated with the personal computing device, at least one user control input for controlling at least one user-controllable stimulation parameter of the ear stimulation device; determining, with a stimulator control module, at least one stimulus control parameter based on at least one of the mood of the user, the at least one secondary factor, and the at least one user control input; and communicating, with a controller interface module, at least one stimulus control parameter to a stimulator controller, the stimulator controller adapted to control the ear stimulation device responsive to the at least one stimulus control parameter. In addition to the foregoing, other method aspects are described in the claims, drawings, and text forming a part of the disclosure set forth herein.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1 is an illustration of the external anatomy of the ear of a human.

FIG. 47 is a flow diagram of a method.

DETAILED DESCRIPTION

Figure 2A:
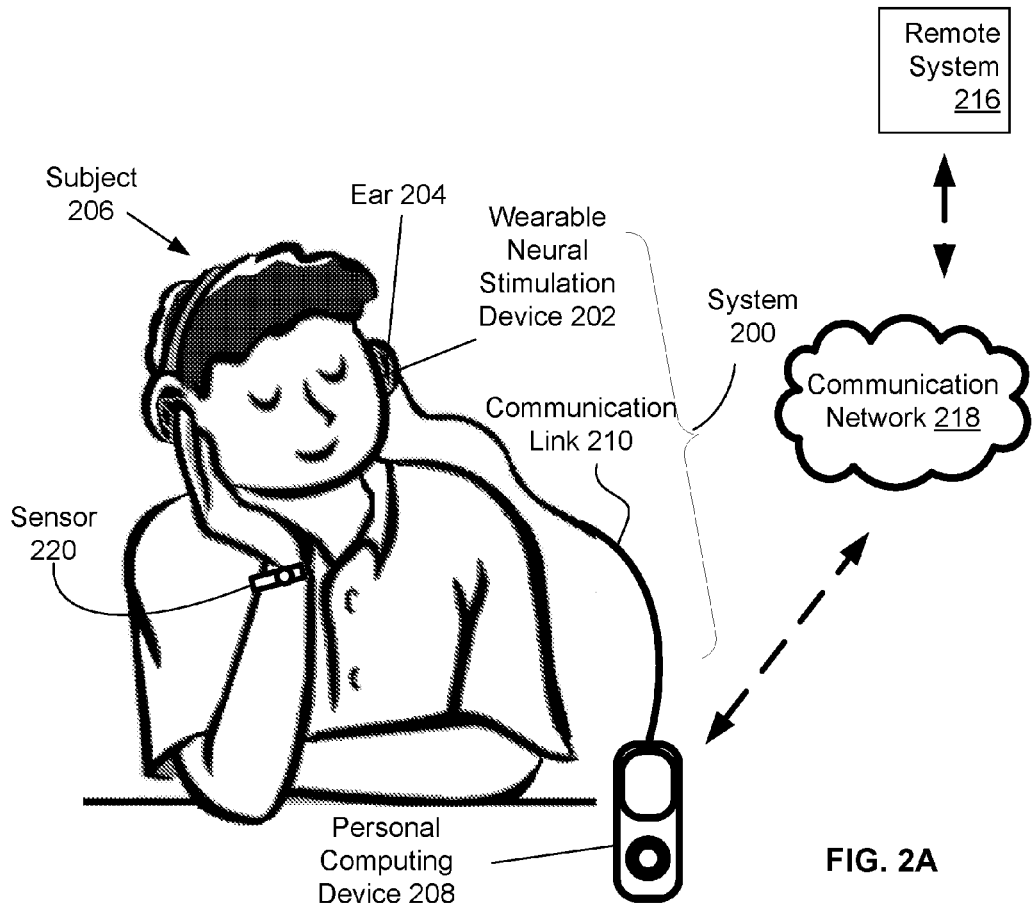
FIG. 2A is an illustration of a system including a neural stimulation device worn on the ear of a subject.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Various studies indicate that stimulation of the ear can have beneficial effects on the health of a subject. For example, Rong et al., "Transcutaneous vagus nerve stimulation for the treatment of depression: a study protocol for a double blinded randomized clinical trial," BMC Complementary and Alternative Medicine 2012, 12:255, which is incorporated herein by reference, describes the possibility of using transcutaneous stimulation of the vagus nerve via portions of the ear to treat major depressive disorder (MDD) and other disorders, including epilepsy, bipolar disorder, and morbid obesity. Ellrich, "Transcutaneous Vagus Nerve Stimulations," European Neurological Review, 2011; 6(4): 254-256, which is incorporated herein by reference, describes transcutaneous vagus nerve stimulation via the ear for treating epilepsy and depression.

Nerves innervating the skin on or in the vicinity of the ear of the subject include, e.g., the facial nerve (cranial nerve VII), the glossopharyngeal nerve (cranial nerve IX), the auricular branch of the vagus nerve (cranial nerve X), the auriculotemporal branch of trigeminal nerve (cranial nerve V), the lesser occipital nerve (spinal nerve C3), and the greater auricular nerve (spinal nerves C2, C3). These nerves contain various nerve fibers including sensory nerve fibers, including, for example, nerve fibers from skin mechanoreceptors. Various types of skin mechanoreceptors are well characterized and are innervated by fibers having diameters in the range of approximately 5 to 12 μm (also known as Aβ fibers). Skin mechanoreceptors include, for example, slowly adapting mechanoreceptors, which are more sensitive to continuous stimulation, and rapidly adapting mechanoreceptors, which are more sensitive to transient stimuli. Rapidly adapting mechanoreceptors include Pacinian corpuscles and Meissner's corpuscles, for example.

Mechanoreceptors are activated well by cyclical or vibratory (e.g., sinusoidal) mechanical stimuli having frequencies in the range of 1 Hz to 1000 Hz. In some aspects, such mechanical stimuli may include indentation of the skin by a few micrometers to a few millimeters. Pacinian corpuscles are thought to be most responsive to vibratory mechanical stimuli with frequencies in the range of 200 Hz-300 Hz, while Meissner's Corpuscles are thought to be most responsive to vibratory mechanical stimuli with frequencies in the range of 30-40 Hz.

Electrical stimuli having sinusoidal or other waveforms are also effective for activating sensory fibers. Stimuli may be applied cyclically, for example. See e.g., Ellrich, "Transcutaneous Vagus Nerve Stimulations," European Neurological Review, 2011; 6(4):254-256, which is incorporated herein by reference.

For reference, FIG. 1 depicts an ear 100 of a human subject, showing anatomical structures which may be referred to herein. The external portion of ear 100 is referred to as the pinna 102. FIG. 1 depicts a front/side view of ear 100, showing anterior surface of pinna 104, and a back view of ear 100, showing posterior surface of pinna 106 as well as head 108 of the subject. The surface of the head 108 adjacent the pinna 102 is indicated by shading and reference number 110. Anatomical features of the ear include external auditory meatus 112 (the external ear canal), helix 114, lobe 116, and tragus 118. Concha 120, the indented region in the vicinity of external auditory meatus 112, is comprised of cymba 122 and cavum 124, and bounded by antitragus 126 and antihelix 128. Antihelix 128 includes inferior (anterior) crus of antihelix 130 and superior (posterior) crus of antihelix 132, which bound triangular fossa 134.

Figure 2B:
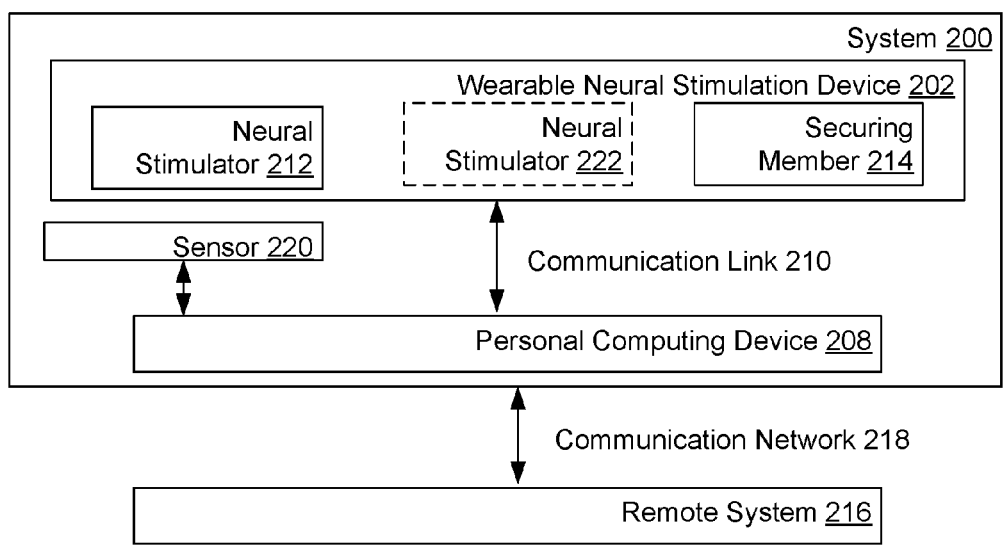
FIG. 2B is a block diagram of the system of FIG. 2A.

FIGS. 2A and 2B depict a generalized system 200 including a wearable neural stimulation device 202 for delivering a stimulus to an ear 204 of a subject 206. System 200 includes a personal computing device 208 in communication with wearable neural stimulation device 202 via communication link 210. Personal computing device 208 can be an audio player, a mobile phone, a computer, or any of various other devices having computing capability (e.g., microprocessor based devices) and including application software and/or suitable hardware for controlling operation of wearable neural stimulation device 202. In an aspect, personal computing device 208 is a wearable computing device. In an aspect, wearable neural stimulation device 202 is used to deliver a stimulus sufficient to activate one or more nerves or nerve branches innervating the skin on or in the vicinity of ear 204 of subject 206. In an aspect, personal computing device 208 is used to control delivery of the stimulus to ear 204 of subject 206. As illustrated in the block diagram of FIG. 2B, and described in greater detail herein below, wearable neural stimulation device 202 includes neural stimulator 212 and securing member 214 for securing neural stimulator 212 to ear 204. In an aspect, personal computing device 208 is configured to send, or receive, information relating to operation of the wearable neural stimulation device 202 to, or from, one or more remote system 216 via a communications network 218. Control of stimulation may be based on data from one or more sensor 220, including, but not limited to, physiological sensors, neural activity sensors, motion sensors, location sensors, or environmental sensors, for example. In some aspects, sensor 220 is worn by the subject at a location distinct from wearable neural stimulation system 202 (e.g., on an armband as depicted in FIG. 2A). In other aspects, one or more sensors are located on a wearable neural stimulation device that can be implanted in the subject, located on the personal computing device, or located elsewhere in the environment of the subject, as depicted and described in the following text and accompanying figures.

In the embodiment of FIGS. 2A and 2B, and in other embodiments described herein, neural stimulator 212 can be any of various types of neural stimulators, including but not limited to mechanical, electrical, magnetic, ultrasonic, optical, or chemical stimulators, as will be discussed in greater detail herein below. In an aspect, neural stimulation devices as described herein can include multiple (two or more) neural stimulators (see e.g., optional additional neural stimulator 222 in FIG. 2B). If multiple neural stimulators are used, they may all be of the same type, or may be of several different types.

In an aspect, neural stimulator 212 is a mechanical stimulator. In an aspect, a mechanical stimulator includes, for example, a vibratory mechanical stimulator that delivers a cyclical or vibrating mechanical stimulus to the skin of the ear of the subject. Vibratory mechanical stimulators can include, for example, various types of vibrating mechanical devices, e.g., electromechanical, piezoelectric, movable coil, electrostatic, magnetostrictive, isodynamic, and/or MEMS devices, for example as used for manufacturing small-scale speakers and microphones.

In an aspect, neural stimulator 212 includes a transcutaneous electrical stimulator for delivering a transcutaneous electrical stimulus. For example, neural stimulator 212 may include an electrode or electrical contact designed for contacting the skin surface, for example as described in Rong et al., "Transcutaneous vagus nerve stimulation for the treatment of depression: a study protocol for a double blinded randomized clinical trial," BMC Complementary and Alternative Medicine 2012, 12:255, which is incorporated herein by reference. In an aspect, neural stimulator 212 includes a magnetic stimulator for delivering a transcutaneous magnetic stimulus. For example, such a magnetic stimulator may include one or more coil through which electrical current is passed to generate a magnetic field. The magnetic field induces electrical currents within the tissue in/around the ear of the subject to activate neural structures. In an aspect, neural stimulator 212 includes an ultrasonic stimulator, for example as described in Legon et al., "Pulsed Ultrasound Differentially Stimulates Somatosensory Circuits in Humans as Indicated by EEG and fMRI," PLOS ONE 7(12): e5177. Doi:10.01371/journal.pone.0051177, December 2012, which is incorporated herein by reference. In some aspects, other types of neural stimulators, such as optical or chemical stimulators are used. See, for example, stimulators described in U.S. Pat. No. 8,170,658 to Dacey, Jr. et al., which is incorporated herein by reference.

In some aspects, circuitry for driving delivery of the neural stimulus is included fully or partially in wearable neural stimulation device 202. In some aspects, some or all of the circuitry for driving delivery of the neural stimulus are housed separately from wearable neural stimulation device 202, and a control signal for driving delivery of the neural stimulus by neural stimulator 212 is provided by personal computing device 208, or from remote system 216 via communication network 218.

Various examples and embodiments of neural stimulation devices are described herein. In various aspects of neural stimulation systems described herein, neural stimulation devices are wearable, i.e. the device can be carried by or worn on the ear of a subject, secured by a securing member, in order to position one or more neural stimulator with respect to a portion of the ear of the subject, or in some cases, in the vicinity of the ear of the subject. Various types of securing members may be used, without limitation. A securing member may also serve to position one or more sensors on or in the vicinity of the ear of the subject and may also include or support other system components, such as electrical circuitry components. Examples of neural stimulation devices including different types of securing members are shown in FIGS. 3-6.

Figure 3:
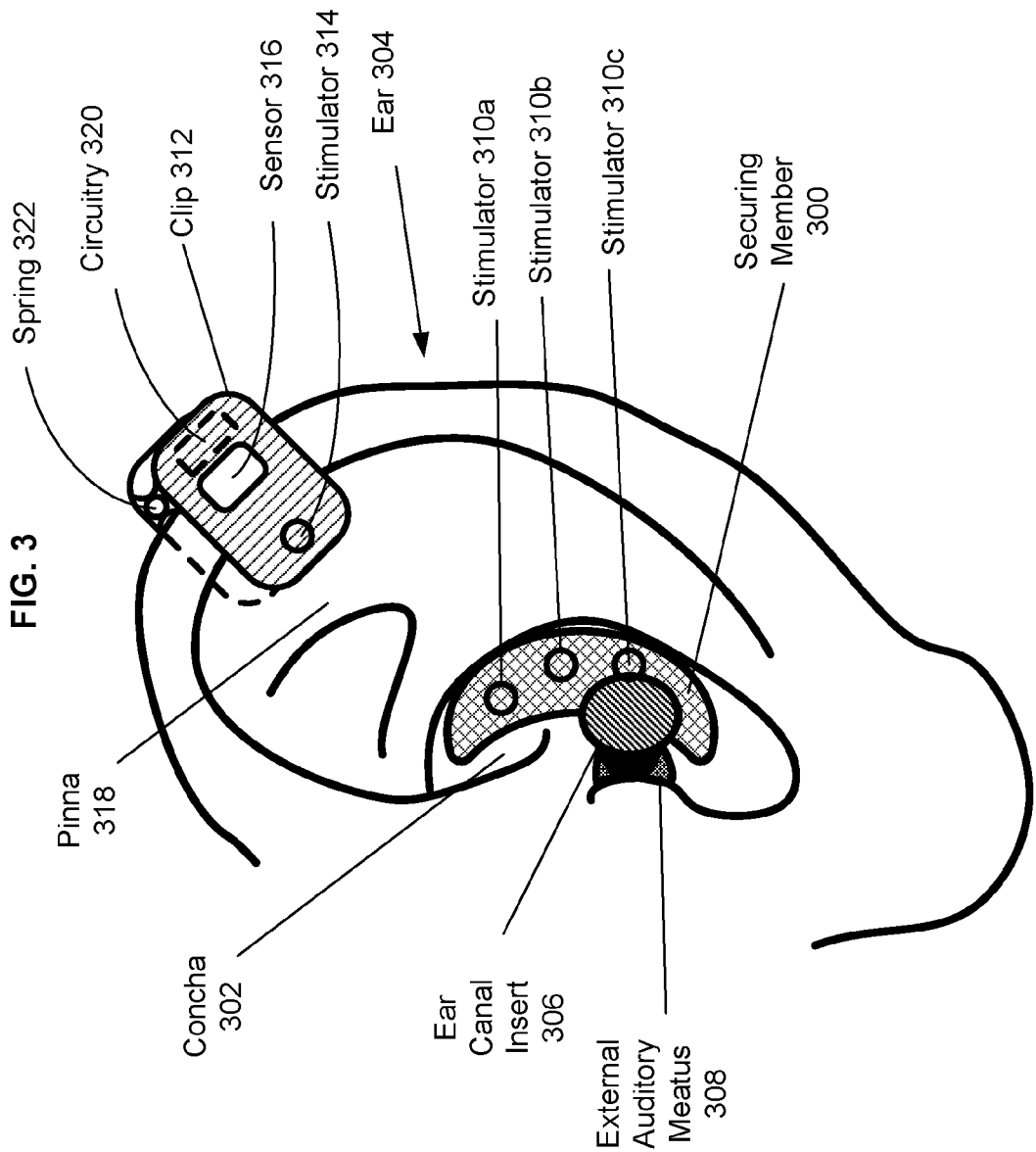
FIG. 3 depicts a stimulation device including a securing member configured to fit in the concha, and a clip securing member.

FIG. 3 depicts securing member 300, which is a concha-fitted member configured to fit into concha 302 of ear 304. In this example, securing member 300 has a size and shape sufficient to be retained in concha 302 by friction and/or tensioning of securing member 300 with respect to concha 302. Other system components may be attached to securing member 300, e.g., ear canal insert 306, which extends into external auditory meatus (ear canal) 308 and stimulators 310a, 310b, and 310c. In addition, system components may be built into or contained within securing member 300, e.g., control and/or communication circuitry (not shown) used to drive stimulators 310a, 310b, and 310c and/or provide for communication with e.g., a personal computing device (not shown). A battery can be provided in securing member 300 to power the device for wireless operation. FIG. 3 also depicts a second type of securing member, clip 312, for attaching stimulator 314 and/or sensor 316 to the pinna 318 of the subject. Circuitry 320 provides for wireless communication between stimulator 314/sensor 316 and circuitry on securing member 300 or a personal computing device or remote system. Spring 322 provides spring force to secure clip 312 onto pinna 318. Clip 312 may be formed of a resilient material or formed from two sections of rigid material, joined at a hinge.

FIGS. 4A and 4B depict securing member 400 having a hanger-style configuration designed to hang on pinna 402. The hanger-style configuration is similar to the configuration used in certain types of headsets for listening to music. Securing member 400 includes anterior portion 404, which in use (shown in FIG. 4B) is positioned anterior to the ear of the subject (i.e. in front of pinna 402); over-ear portion 406, which arcs over and behind pinna 402; and posterior portion 408, which fits behind pinna 402. In an aspect, securing member 400 includes downward extension 410. In an aspect, wired communication link 412 (e.g., a cable) provides for connection of electrical components on securing member 400 to a remote computing device. For example, electrodes 414a and 414b on posterior portion 408 of securing member 400 are used to deliver electrical stimulation under control of a control signal delivered via wired communication link 412. Securing member 400 also includes ear canal insert 416, which fits into the external auditory meatus 112. A sensor 418 on ear canal insert 416 can be used to sense a physiological signal, which in some aspects is used to determine the stimulation delivered with electrodes 414a and 414b. Physiological sensor 418 may include, for example, an electrode for sensing a heart rate, or other physiological sensor as described in greater detail elsewhere herein. Additional sensors 420 and 422 are located on the aspect of posterior portion 408, facing and adapted to contact the surface of the head adjacent the pinna 402. In an aspect, sensors 420 and 422 are electrodes configured to detect an electroencephalographic (EEG) signal.

Figure 5:
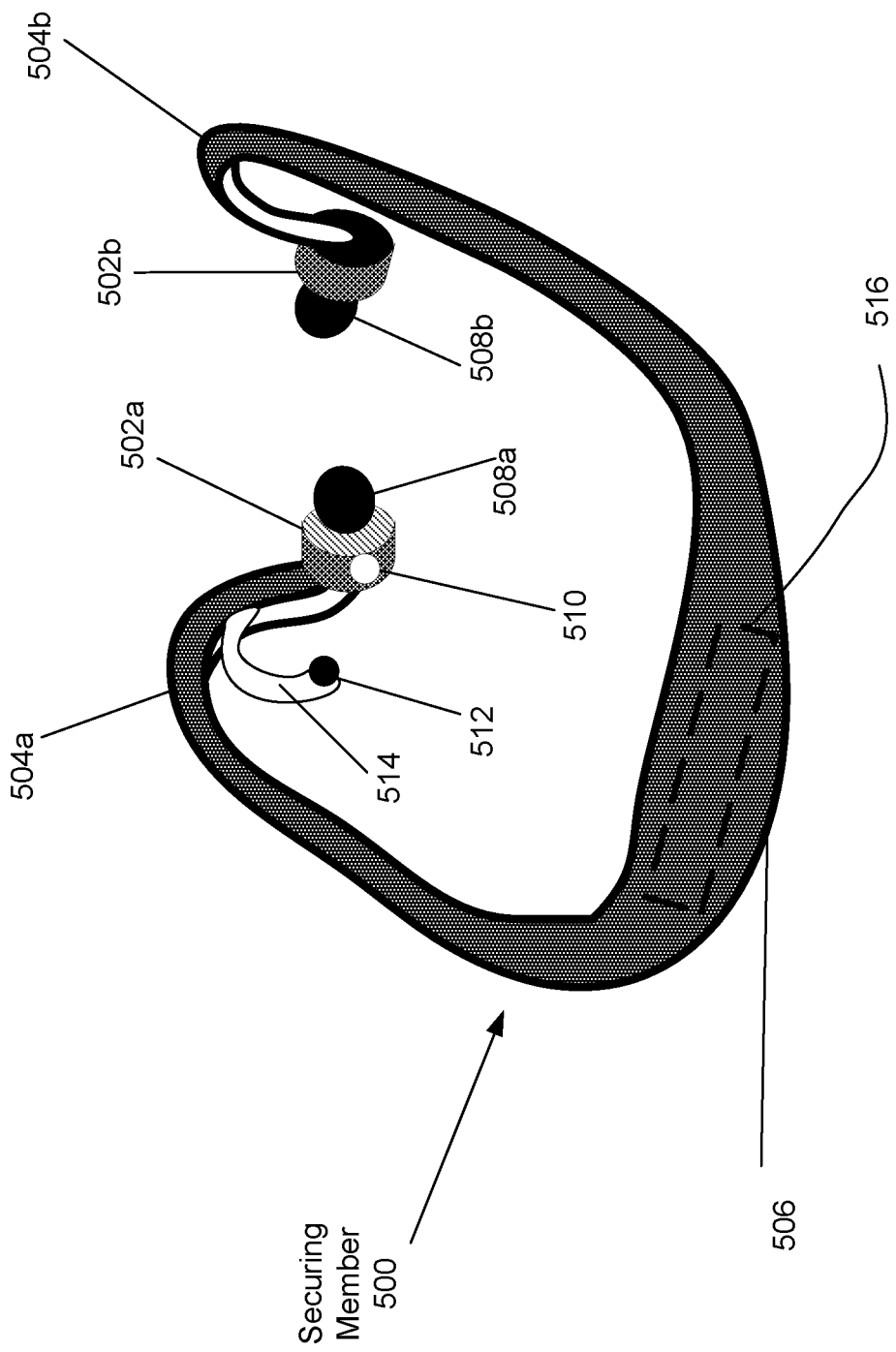
FIG. 5 depicts an embodiment of a stimulation device.

FIG. 5 depicts securing member 500 having a loop configuration of a type used for wireless headsets. Securing member 500 includes earpieces 502a and 502b, which fit into the left and right ears of a subject, respectively (e.g., fitting into one or both of the concha and external auditory meatus). Securing member 500 also includes arcs 504a and 504b, which fit over and behind the two ears of the subject, and connecting loop 506 which fits behind the head of the subject and connects earpieces 502a and 502b. In an aspect, securing member 500 is sufficiently rigid to maintain earpieces 502a and 502b in position in the ears of the subject while the subject moves about (e.g., walking or running). In an aspect, ear canal inserts 508a and 508b fit into the ear canals of the subject. A neural stimulator 510 may be positioned on earpiece 502a, as shown, or alternatively (or in addition) on ear canal extension 508a. A secondary neural stimulator 512 may be located on pinna extension 514. Extension 514 serves to position secondary neural stimulator 512 on the pinna of the subject at a desired location. In an aspect, extension 514 can be adjusted by elastic or plastic deformation to change the positioning of neural stimulator 512 on the pinna. In some aspects, extension 514 can include an adjustable linkage that provides for positioning of neural stimulator 512 with respect to the pinna.

FIG. 5 depicts a system in which neural stimulators 510 and 512 are positioned on securing member 500 so as to deliver stimulation to the left ear of the subject. Depending upon the desired application, neural stimulators can be positioned on one or both ears of the subject. In some aspects, stimulation is delivered to only one ear, while in other aspects, stimulation is delivered to both ears.

In some aspects, stimulator 512 located on pinna extension 514 can be used as the only, or primary neural stimulator, and stimulator 510 on earpiece 502a can be omitted. Earpieces 502a and 502b can function to hold securing member 500 in place with respect to the head of the subject, and, optionally, to deliver sound (such as a voice signal from a phone or music from an audio player) to the ears of the subject, independent of carrying stimulator 510. Circuitry 516 in securing member 506 includes communication circuitry for wirelessly communicating with other system components, for example a personal computing device (e.g., an audio player, a mobile phone, or a laptop computer). In addition, circuitry 516 may provide for wireless communication with a sensor located at a distance from securing member 500. For example, the wireless headset device depicted in FIG. 5 can be used in combination with sensors in one or more locations, not limited to sensors on securing member 500. Sensors include any type of physiological sensor located in, on or adjacent to the body of the subject (e.g., implanted sensors, sensors secured to the body, sensors in wearable items such as clothing, wristbands); remote sensors, environmental sensors, motion sensors, location sensors, and/or other types of sensors, without limitation.

Figure 6:
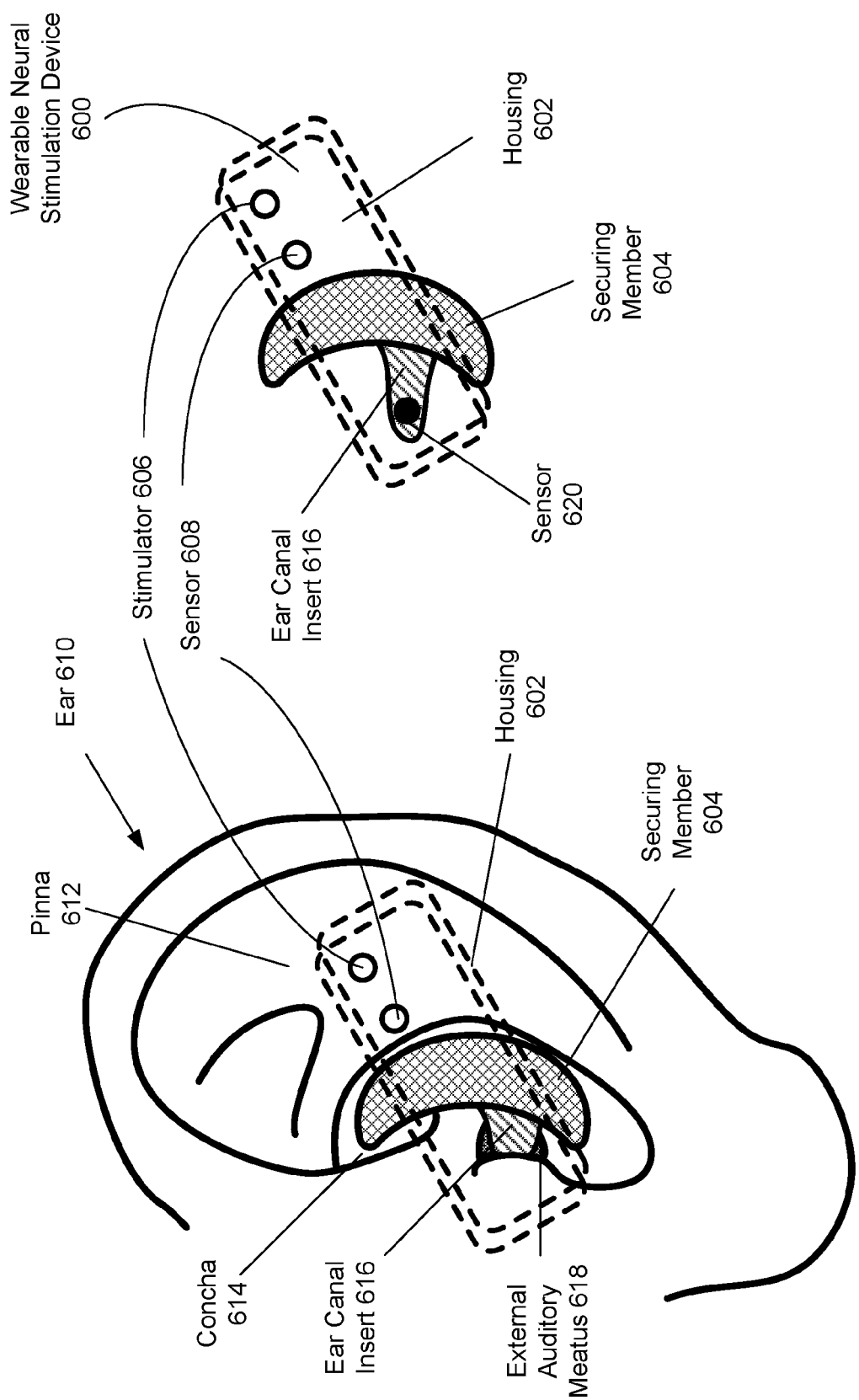
FIG. 6 depicts an embodiment of a stimulation device.

FIG. 6 depicts a further example of a wearable neural stimulation device 600 including a housing 602 attached to a securing member 604. Housing 602 is shown only in a dashed outline so that the position of stimulator 606 and sensor 608 with respect to ear 610 can be seen. Housing 602 is a thin, flat box-like structure, with stimulator 606 and sensor 608 mounted on the exterior of housing 602 on the side facing pinna 612. Housing 602 is fastened to or formed integrally with securing member 604. Securing member 604 fits into concha 614 to secure device 600 to ear 610. Ear canal insert 616 fits into external auditory meatus 618. Sensor 620 on ear canal insert 616 senses a physiological signal from external auditory meatus 618. Sensor 608 is an environmental sensor that senses light from the environment of the subject, e.g., to determine whether it is day or night.

Figure 7:
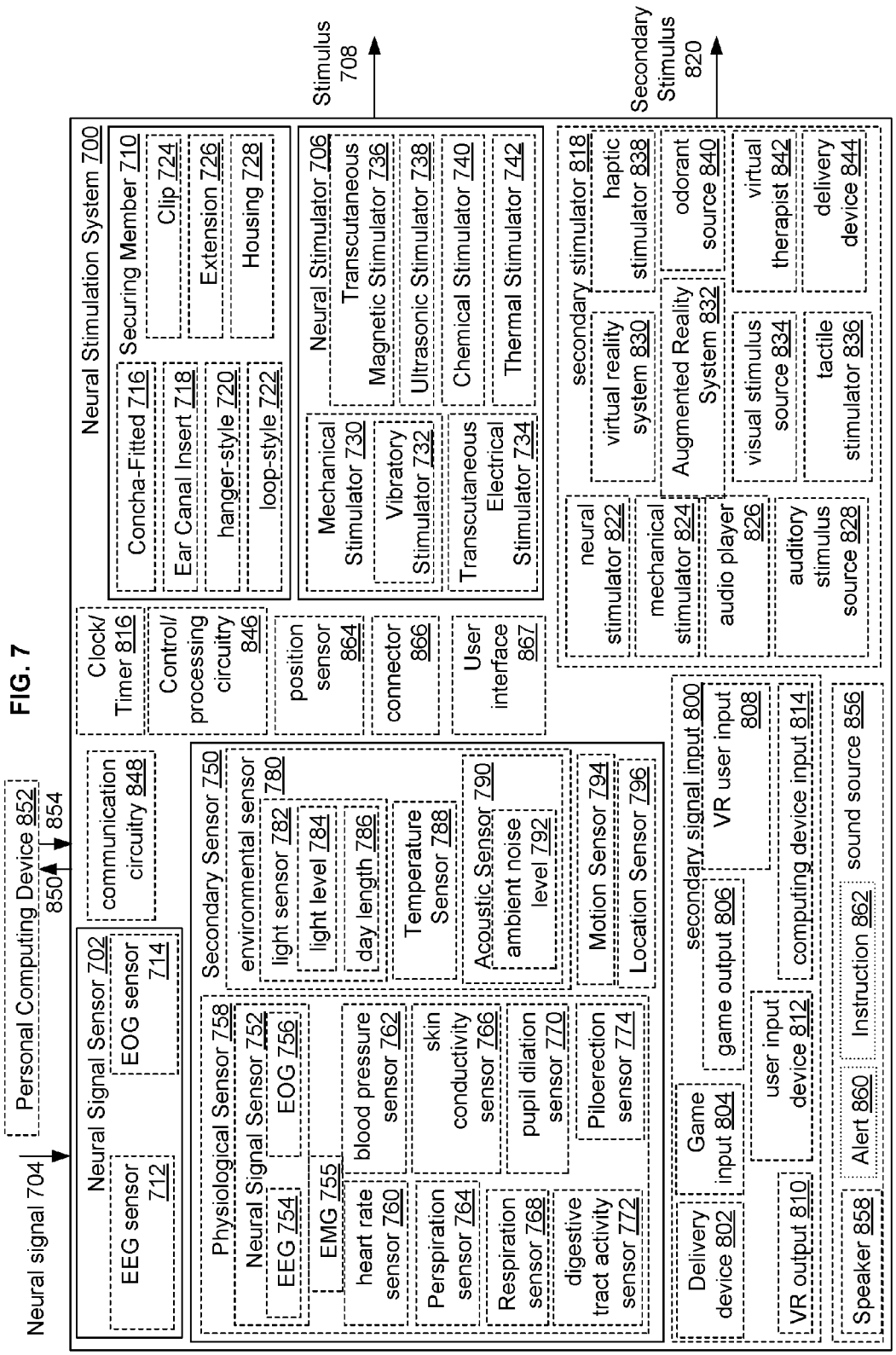
FIG. 7 is a block diagram of a neural stimulation system.

FIG. 7 is a block diagram of a neural stimulation system 700. Neural stimulation 700 system includes neural signal sensor 702, which is adapted to sense a neural signal 704 from a subject. Neural signal 704 may be an electroencephalographic (EEG) signal or electrooculographic (EOG) signal, and in an aspect is indicative of a physiological status of the subject. Neural stimulation system 700 also includes neural stimulator 706, which is adapted to produce a stimulus 708 responsive to sensed neural signal 704, stimulus 708 configured to activate at least one sensory nerve fiber innervating at least a portion of a pinna of the subject. Neural stimulation system 700 also includes securing member 710 configured to secure neural stimulator 706 to the pinna of the subject.

In various aspects, neural signal sensor 702 can be an electroencephalographic signal sensor 712 or electrooculographic signal sensor 714. Electroencephalographic signal sensor 712 can be configured to fit within an ear canal of a subject, e.g., on an ear canal insert as depicted in FIG. 4A (for example as described in U.S. Patent Publication 2003/0195588 to Fischell et al., or U.S. Patent Publication 2006/0094974 to Cain, both of which are incorporated herein by reference). EOG sensor 714 can be located on an extension (e.g., similar to extension 514 shown in FIG. 5) to position EOG sensor 714 on the subject's temple or side of the subject's head. An electromyographic signal sensor could be similarly placed. Physiological status of the subject, as indicated by neural signal 704, may include indications or symptoms of various types of physiological status, including various brain-related disorders or statuses, or other physiological statuses. Brain-related disorders include, for example, mental health disorders (e.g., psychological or psychiatric disorder), depression, post-traumatic stress disorder, seasonal affective disorder, anxiety, headache (e.g., primary headache, cluster headache, or migraine headache), or epilepsy). Neural signal sensor 704 may include other types of neural signal sensors, including external or implantable sensors, located in or on the ear or other part of the body. One or more neural signal sensors may be used.

Figure 4:
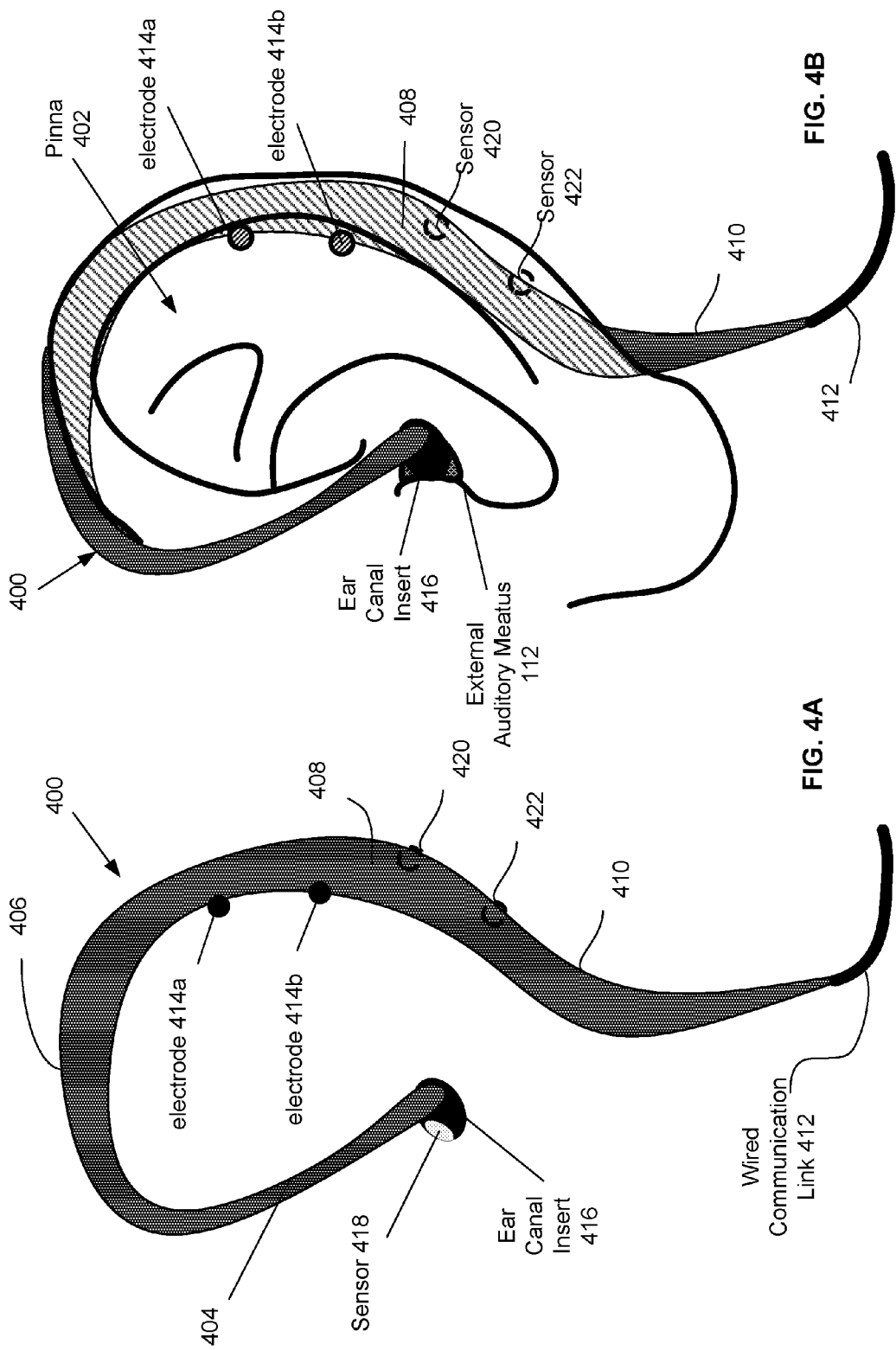
FIG. 4A depicts a stimulation device including a hanger-style securing member.
FIG. 4B depicts the stimulation device of FIG. 4A positioned on an ear.

In various aspects, securing member 710 is configured to secure neural stimulator 706 to different portions of the pinna of the subject. For example, in an aspect, securing member 710 includes a concha-fitted portion 716, configured to fit into the concha of the subject (e.g., as depicted in FIG. 3). In an aspect, securing member 710 includes an ear canal insert 718 configured to fit in the ear canal of the subject (e.g., as depicted in FIGS. 4A, 4B, and 5). In another aspect, securing member 710 is a hanger-style securing member 720, as depicted in FIGS. 4A and 4B. Hanger-style securing member 720 can be used to secure the neural stimulator to the back of the pinna, or to the surface of the head adjacent the pinna. In another aspect, securing member 710 is a loop-style securing member 722, (e.g., of the type depicted in FIG. 5). In another aspect, securing member 710 includes a clip 724 (e.g., of the type depicted in FIG. 3). A clip may be used to secure neural stimulator 706 to various parts of the front or back of the pinna, including the front or back of the ear lobe. In another aspect, securing member 720 includes an extension 726 (e.g., such as extension 514 depicted in FIG. 5). Such an extension can be used to position the neural stimulator in virtually any desired position on the pinna, or on the head adjacent to and above, below, in front of, or behind the ear. In an aspect, securing member 710 includes a housing 728. It should be noted that housing 710 may in some cases function as an extension. For example, housing 602 depicted in FIG. 6 also functions as an extension extending from securing member 604 to provide for placement and securing of stimulator 606 and sensor 608 on a portion of the pinna 612 not immediately adjacent securing member 604. Securing member 710 can be configured to secure the neural stimulator to the concha, tragus, front or back of the pinna, the helix, or various other parts of the pinna, e.g., the triangular fossa, antihelix, superior or inferior crus of the antihelix, antitragus, or tragus of the subject. In some aspects securing member 710 is permanently configured to position neural stimulator 706 in a particular position with respect to the ear of the subject, wherein in some aspects securing member 710 is adjustable such that the positioning of neural stimulator 706 can be selected by the subject. For example, a sensor or stimulator may be secured to a particular portion of the pinna by being pressed sufficiently firmly against the pinna by the securing member or extension to form a reliable mechanical or electrical contact with the pinna. In an aspect, securing member 710 includes a shape memory material. Various materials may be suitable for the construction of securing member 710, including but not limited to hard or soft, elastically or plastically deformable polymers, metals, ceramics, glasses, and composites formed therefrom. Flexible or stretchable electronic circuitry, formed from flexible materials or structures (e.g. conductors having, e.g., a serpentine design) or resilient conductive materials such as conductive polymers can be used in sensors and stimulators that conform to the pinna. While discussion herein has focused on positioning of the neural stimulator by securing member 710, it will be appreciated that securing member 710 can also be configured to position sensors with respect to the ear in a similar fashion. Several such examples are provided in FIGS. 3-6.

In an aspect, the neural stimulator 706 is positioned with respect to securing member 710 such that when securing member 710 is worn on the pinna, neural stimulator 706 is positioned (secured) over a specific region of the pinna, e.g., a region of the pinna innervated by a cranial nerve, e.g., the vagus nerve, the facial nerve, the trigeminal nerve, or the glossopharyngeal nerve. Such positioning may be selected based upon knowledge of the innervation of the pinna, for example, as provided in references texts such as Cranial Nerves in Health and Disease, by Linda Wilson-Pauwels, Elizabeth J. Akesson, Patricia A. Stewart, and Sian D. Spacey; BC Decker Inc.; 2 edition (Jan. 1, 2002); ISBN-10: 1550091646/ISBN-13: 978-1550091649, which is incorporated herein by reference.

As noted above, neural stimulator 706 may be, for example, a mechanical stimulator 730 (e.g., a vibratory mechanical stimulator 732), a transcutaneous electrical stimulator 734, a transcutaneous magnetic stimulator 736, an ultrasonic stimulator 738, a chemical stimulator 740, a thermal stimulator 742, or other type of stimulator.

As shown in FIG. 7, in an aspect, neural stimulation system 700 includes at least one secondary sensor 750. In an aspect, neural signal sensor 702 is a primary neural signal sensor, and secondary sensor 750 is a secondary neural signal sensor 752, which may be, for example, an electroencephalographic (EEG) sensor 754, or electrooculographic (EOG) sensor 756. The secondary neural signal sensor 752 may be of the same or different type as primary neural signal sensor 702, and may be located at the same or different location on the body as primary neural signal sensor 702. In an aspect, secondary sensor 750 is a physiological sensor 758, for example, an electromyographic (EMG) sensor 755, a heart rate sensor 760 (which may be used to heart rhythm variability, as well as heart rate, and may include, but is not limited to, and EKG or pulse-oximeter based heart rate sensor), blood pressure sensor 762, perspiration sensor 764, skin conductivity sensor 766, respiration sensor 768, pupil dilation sensor 770, digestive tract activity sensor 772, or piloerection sensor 774. In another aspect, secondary sensor 750 is an environmental sensor, for example a light sensor 782, which may be configured to sense light level 784 and or day length 786. Environmental sensor 750 may include a temperature sensor 788, or an acoustic sensor 790, e.g., configured to sense ambient noise level 792. Other types of sensors for providing information regarding the state of the subject and his or her environment may be used, without limitation, including motion sensor 794 or location sensor 796, for example. A variety of physiological and environmental sensors are described in U.S. Pat. No. 8,204,786 to LeBoueuf et al., which is incorporated herein by reference. Digestive tract activity may be sensed with external acoustical sensors, for example as described in "New disposable biosensor may help physicians determine which patients can safely be fed following surgery," MedicalXpress, Aug. 7, 2014, which is incorporated herein by reference.

In an aspect, neural stimulation system 700 includes a secondary signal input 800. In various aspects, the signal received at secondary signal input 800 includes a signal from a delivery device 802 (indicative of delivery of a drug or nutraceutical to the subject), an input to a game 804 (e.g., a signal corresponding to the subjects input to a video game played by the subject), an output from a game 806 (e.g., a signal output by a game system indicative of a state of or an event in a game played by the subject), a user input to a virtual reality system 808, an output from a virtual reality system 810 (e.g., a signal output by the VR system indicative of an state of or an event in the VR system), a user input device 812 (e.g., a user input device of a computing device or a user input to the neural stimulation system), or a computing device input 814 (e.g., a data input). Inputs received via a user input device or computing device input may be indicative of intake of a food item, beverage, nutraceutical, or pharmaceutical by the subject, for example. Inputs received via a user input device may be provided by the subject, or by another user, e.g. a medical caregiver. Inputs may be provided spontaneously by the user, or in response to a prompt or query. In an aspect, inputs may be provided by the user in response to queries or prompts that form a part of a quiz, questionnaire, or survey, including, e.g. questions presented in yes/no or multiple choice response format. User responses provided in response to such prompts or queries may indicate the subject's mental or emotional state. Inputs received via a data input may include, for example, health-related information of the subject, including genome information or microbiome information of the subject, information from medical-records of the subject, or other information pertaining to the health of the subject.

In an aspect, neural stimulation system 700 includes a clock or timer 816. In various aspects, neural stimulator 706 is adapted to produce stimulus 708 based at least in part on a time of day indicated by clock/timer 816, and/or based at least in part on a date indicated by clock/timer 816.

Data drawn from one or more neural signals, physiological signals, environmental signals, or other secondary signals (e.g. obtained with secondary sensor 750 in FIG. 7) or secondary inputs (e.g. secondary signal input 800 in FIG. 7), as well as clock or timer information, can be correlated with a mental or emotional state of the subject, reported to a medical care provider or other party, and/or stored in the subject's medical or health records. In particular, values of any such parameters that are indicative of worsening mental or physical/physiological status of the subject can be reported to a medical care provider so that an appropriate intervention can be made, and/or used as a basis for modulating the delivery of neural stimulation.

In various aspects, neural stimulation system 700 includes at least one secondary stimulator 818 for delivery a secondary stimulus 820 to the subject. In an aspect, secondary stimulator 818 is a secondary neural stimulator 822, which may be any of the various types of neural stimulators described in connection with neural stimulator 706, and which may be of the same or different type as neural stimulator 706. Alternatively, secondary stimulator 818 may include a mechanical stimulator 824, an audio player 826, an auditory stimulus source 828, a virtual reality system 830, an augmented reality system 832, a visual stimulus source 834, a tactile stimulator 836, a haptic stimulator 838, an odorant source 840, a virtual therapist, or a delivery device 844, for delivering a drug or nutraceutical, for example.

In various aspects, neural stimulation system 700 includes control circuitry 846 carried by securing member 710 (either directly on securing member 710, or on an extension or housing connected to securing member 710, e.g., as depicted in FIGS. 3-6), the control circuitry 846 configured to control neural stimulator 706.

In an aspect, neural stimulation system 700 includes communication circuitry 848 carried by securing member 710 and configured for at least one of sending one or more signal 850 to a personal computing device 852 and receiving one or more signal 854 from personal computing device 852.

In an aspect, neural stimulation system 700 includes a sound source 856, for delivering an auditory signal to the subject. Sound source 856 may be, for example, a speaker 858. Sound source 856 may be configured (e.g., with appropriate electronic circuitry, not shown) to delivery an instruction 860 or alert 862 to the subject.

In an aspect, neural stimulation system 700 includes position sensor 864 for sensing the position of neural stimulator 706 with respect to the pinna of the subject. Position sensor 864 may detect the position of neural stimulator 706 with respect to the pinna by detecting electrical activity from a nerve, by detecting an image of the ear and determining the position based on landmarks in the image, or by detecting a temperature, pressure, or capacitive signal indicative of adequate contact of the stimulator with the ear, for example.

In an aspect, neural stimulation system 700 includes connector 866 for connecting the neural stimulator to a personal computing device. Connector 866 includes, for example, a jack or port for creating a wired (cable) connection with the personal computing device. In an aspect, neural stimulation system 700 includes user interface 867 for receiving input from the subject or presenting information to the subject. In an aspect, user interface 867 includes a small display, one or more indicator lights and simple user inputs, such as one or more buttons or dials for adjusting device setting and viewing and modifying system settings.

Figure 8:
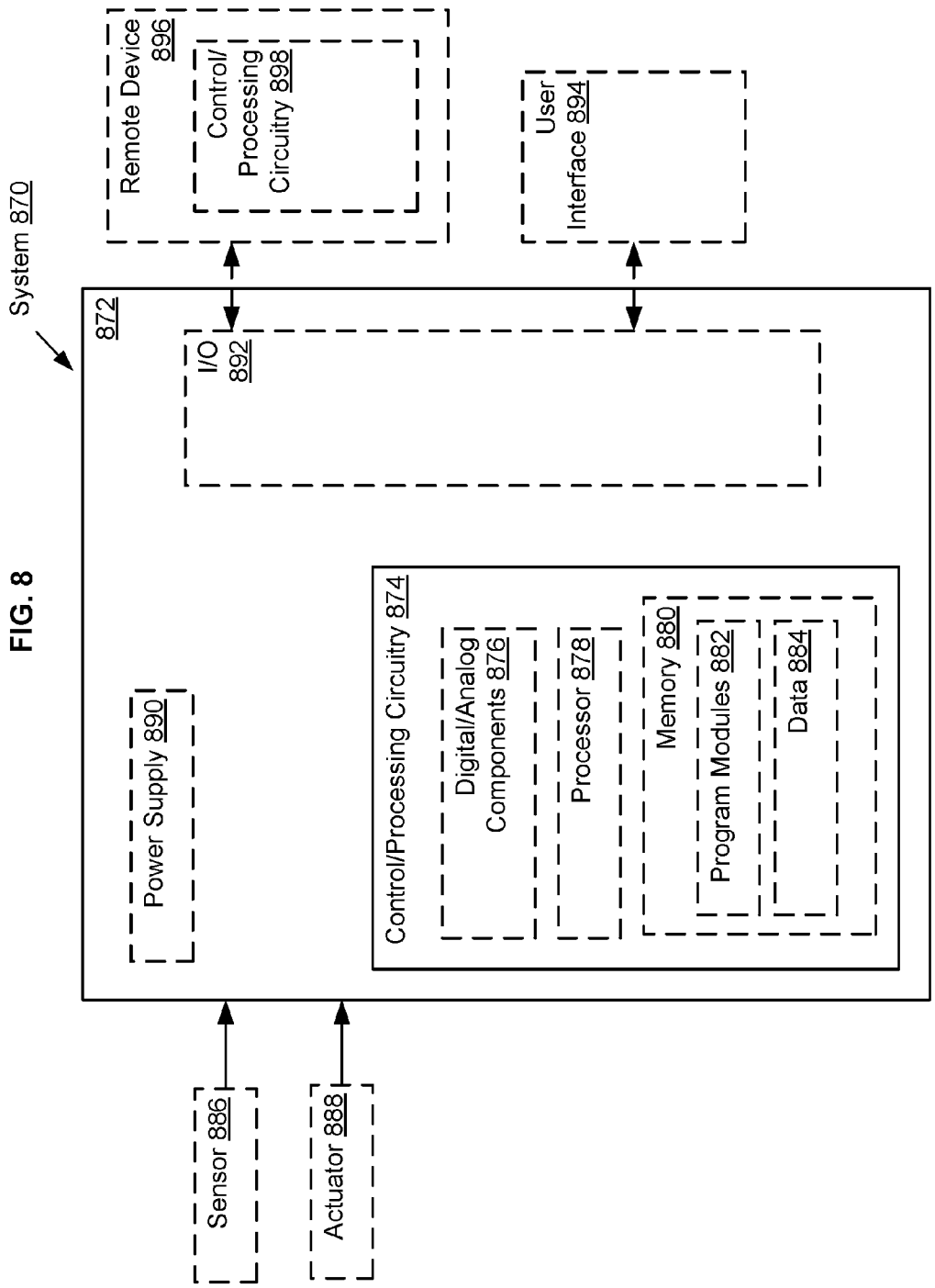
FIG. 8 is a block diagram of a computing system.

FIG. 8 illustrates a generalized form of circuitry-based systems as depicted in FIG. 7 and elsewhere herein. Although specific embodiments are described herein, those skilled in the art will appreciate that methods and systems as described herein can be implemented in various ways. Reference is made herein to various circuitry systems and subsystems (e.g., neural stimulation system 700 includes control/processing circuitry 846 in FIG. 7, which may be considered to be control/processing circuitry. As shown generically in FIG. 8, a system 870 includes a circuitry-based system 872. Circuitry-based system 872, which in some aspects is a computing device or computing subsystem, includes control/processing circuitry 874, which includes any or all of digital and/or analog components 876, one or more processor 878 (e.g., a microprocessor), and memory 880, which may store one or more program module 882 and/or data 884. In some aspects, control/processing circuitry provides for preliminary handling of data from one or more sensor 886, transfer of data to remote device 896, receipt of control signal from remote device 896, and actuation of actuator 888, which may be for example a neural stimulator (such as neural stimulator 706 as shown in FIG. 7). Systems as described herein may receive signals from various sensors (e.g., sensor 886 depicted in FIG. 8). System 870 may include other components as known to those skilled in the art, e.g., one or more power supply 890, I/O structure 892, clock, timer, data bus, etc. I/O structure 892 permits communication with various types of user interface devices (represented by user interface 894, which may include one or more input devices such as a keyboard, button, switch, computer mouse, or touchscreen or one or more output devices such as screen, sound source, alphanumeric display, Braille display, etc.) and communication with various types of remote device 896, e.g., remote system 216 in FIGS. 2A-2B, which may have control/processing capability conferred by control/processing circuitry 898.

In a general sense, the various embodiments described herein can be implemented, individually and/or collectively, by various types of electrical circuitry having a wide range of electrical components such as hardware, software, firmware, and/or virtually any combination thereof. Electrical circuitry (including control/processing circuitry 846 in FIG. 7, for example) includes electrical circuitry having at least one discrete electrical circuit, electrical circuitry having at least one integrated circuit, electrical circuitry having at least one application specific integrated circuit, electrical circuitry forming a computing device configured by a computer program (e.g., a computer configured by a computer program which at least partially carries out processes and/or devices described herein, or a microprocessor configured by a computer program which at least partially carries out processes and/or devices described herein), electrical circuitry forming a memory device, which may include various types of memory (e.g., random access, flash, read only, etc.)), electrical circuitry forming a communications device (e.g., communication circuitry 848 in FIG. 7) (e.g., a modem, communications switch, optical-electrical equipment, etc.), and/or any non-electrical analog thereto, such as optical or other analogs (e.g., graphene based circuitry). In an embodiment, the system is integrated in such a manner that the system operates as a unique system configured specifically for function of the neural stimulation system described herein. In an embodiment, one or more associated computing devices of the system operate as specific use computers for purposes of the claimed system, and not general use computers. In an embodiment, one or more of the associated computing devices of the system are hard-wired with a specific ROM to instruct the one or more computing devices.

In a general sense, the various aspects described herein which can be implemented, individually and/or collectively, by a wide range of hardware, software, firmware, and/or any combination thereof can be viewed as being composed of various types of "electrical circuitry."

At least a portion of the devices and/or processes described herein can be integrated into a data processing system. A data processing system generally includes one or more of a system unit housing, a video display, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

In various embodiments, methods as described herein may be performed according to instructions implementable in hardware, software, and/or firmware. Such instructions may be stored in non-transitory machine-readable data storage media, for example. The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Optical aspects of implementations will typically employ optically-oriented hardware, software, and or firmware.

In some implementations described herein, logic and similar implementations may include software or other control structures. Electrical circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components.

Implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled//implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit).

This detailed description sets forth various embodiments of devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In an embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to non-transitory machine-readable data storage media such as a recordable type medium such as a floppy disk, a hard disk drive, a Compact Disc (CD), a Digital Video Disk (DVD), a digital tape, a computer memory, etc. A signal bearing medium may also include transmission type medium such as a digital and/or an analog communication medium (e.g., a fiber optic cable, a waveguide, a wired communications link, a wireless communication link (e.g., transmitter, receiver, transmission logic, reception logic, etc.) and so forth).

Figure 9:
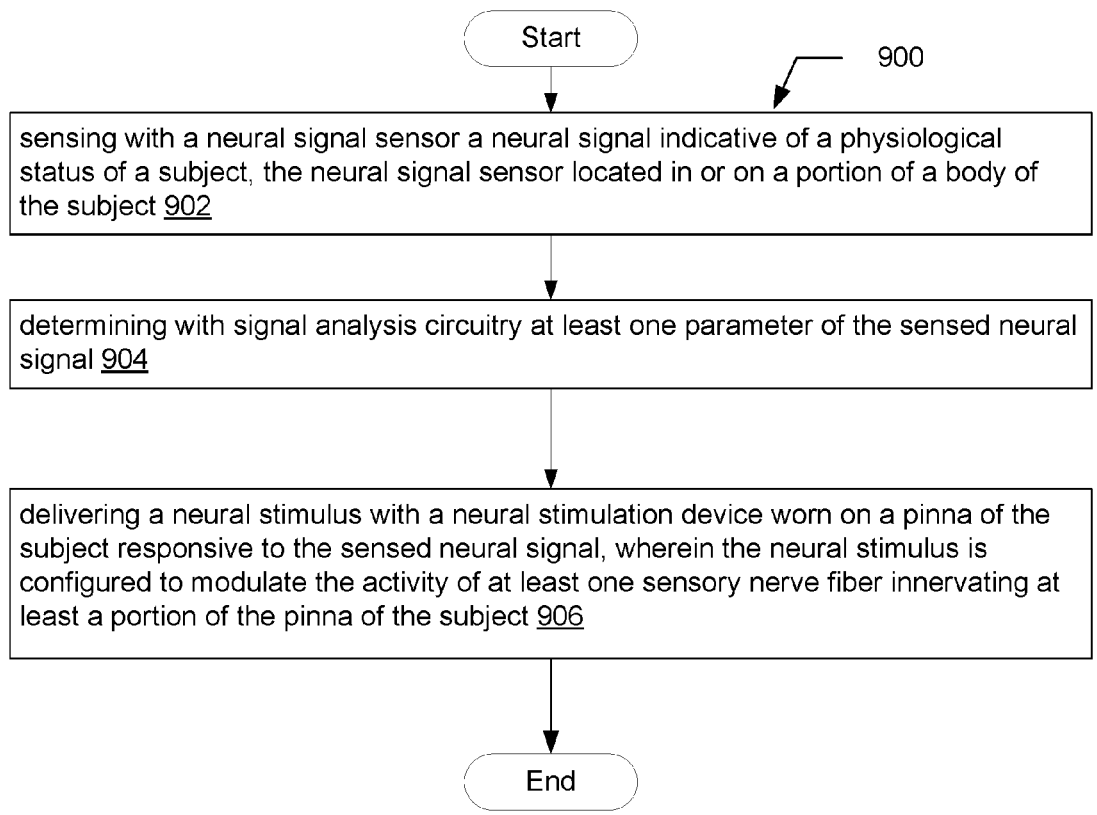
FIG. 9 is a flow diagram of a method.

FIG. 9 is a flow diagram of a method 900 relating to use of a neural stimulation system as depicted in FIG. 7. Here and elsewhere, method steps outlined with dashed lines represent steps that are included in some, but not all method aspects, and combinations of steps other than those specifically depicted in the figures are possible as would be known by those having ordinary skill in the relevant art. Method 900 includes sensing with a neural signal sensor a neural signal indicative of a physiological status of a subject, the neural signal sensor located in or on a portion of a body of the subject, as indicated at 902; determining with signal analysis circuitry at least one parameter of the sensed neural signal, as indicated at 904; and delivering a neural stimulus with a neural stimulation device worn on a pinna of the subject responsive to the sensed neural signal, wherein the neural stimulus is configured to modulate the activity of at least one sensory nerve fiber innervating at least a portion of the pinna of the subject, as indicated at 906. In an aspect, the neural stimulus is of sufficient frequency and amplitude to modulate the activity of the at least one sensory nerve fiber innervating the at least a portion of the pinna of the subject. For example, in various aspects the neural stimulus has a frequency in the approximate range of 1 Hz-1000 Hz, 10 Hz-500 Hz, 30 Hz-40 Hz, 10 Hz-50 Hz, 10 Hz-80 Hz, 50 Hz-100 Hz, or 200-300 Hz. In an aspect, the stimulus has a sinusoidal waveform. In other aspects, the stimulus may have a triangular, rectangular, square, trapezoidal, or other waveform, delivered cyclically, with cycle frequencies in the ranges listed above. It will be appreciated that depending on the stimulus waveform or pulse shape, or envelope shape, a given stimulus may include higher or lower frequencies. The neural stimulus may be delivered according to programmed pattern, which may be stored in memory on the neural stimulation device or on a personal computing device or other remote device in communication with the neural stimulation device. In various aspects, the neural stimulus is delivered continuously, intermittently, and/or in a time-varying fashion. The neural stimulus may be a pulsed stimulus.

In an aspect, the neural stimulus is delivered with a neural stimulation device and/or neural stimulus configured to activate a cranial nerve, such as the vagus nerve, facial nerve, trigeminal nerve, or glossopharyngeal nerve. The neural stimulation device can be configured to stimulate a particular nerve by one or both of positioning the neural stimulator on at least a portion of a receptive field of the nerve of interest, and selecting the amplitude and other stimulus parameters (e.g. frequency, waveform, duration) of the stimulus delivered to activate the nerve fibers in the nerve of interest.

In an aspect, the method includes delivering the neural stimulus responsive to the at least one parameter of the sensed neural signal. The at least one parameter may include, for example, a frequency content of an electroencephalographic signal, an amplitude of an electroencephalographic signal, a rate of eye movement determined from an electrooculogram, or a gaze direction determined from an electrooculogram. In some aspects, such parameters are indicative of a brain-related disorder, or symptoms thereof. In an aspect, method 900 includes delivering the neural stimulus in response to detection of symptoms of a brain-related disorder (which may be, for example, any mental health disorder (e.g., psychological or psychiatric disorder), depression, post-traumatic stress disorder, seasonal affective disorder, anxiety, headache (e.g., primary headache, cluster headache, or migraine headache), or epilepsy). In an aspect, the method includes delivering the neural stimulus until symptoms of the brain-related disorder are no longer detected.

In an aspect, method 900 includes sensing at least one secondary signal with a secondary sensor. In an aspect, delivery of the neural stimulus may be started, stopped, or modulated in response to the secondary signal. The secondary signal may be a secondary neural signal (of the same or different type and sensed from the same or from a different location than the primary neural signal), or it may another type of physiological signal, an environmental signal, a location signal, or a signal from a motion sensor, for example. Such secondary signals may provide additional information relevant for determining whether the neural stimulus should be applied, assessing the subject's response to the neural stimulus, identifying appropriate time of delivery of the neural stimulus, etc. The secondary signal may include other types of secondary signal, e.g., as received by secondary signal input 800 in FIG. 7. In an aspect, method 900 includes delivering at least one secondary stimulus to the subject in addition to the neural stimulus delivered with the neural stimulation device. The secondary stimulus may be any of various types of secondary stimulus, e.g., as delivered with secondary stimulator 818 as described in FIG. 7. In various aspects, method 900 includes controlling the neural stimulation device with control circuitry located at least in part on the neural stimulation device, or with control circuitry located at least in part on a personal computing device in communication with the neural stimulation device worn on the pinna of the subject. In an aspect, method 900 includes sending a signal from the neural stimulation device worn on the pinna of the subject to a personal computing device or receiving a signal from a personal computing device at the neural stimulation device worn on the pinna of the subject. In an aspect, method 900 includes delivering an auditory instruction or an auditory alert to the subject with a sound source operatively connected to the neural stimulation device. In an aspect, method 900 includes sensing a position of the neural stimulation device relative to the pinna of subject with a position sensor operatively connected to the neural stimulation device. If the neural stimulation device is not positioned properly positioned, the auditory instruction or alert may remind the subject to correct the positioning of the neural stimulation device. Alternatively, or in addition, visual alerts can be provided to the subject, in the form of one or more blinking light, graphic, or a text message, delivered via an LED or other light emitting element, an alphanumeric display, a screen, or other display element on the neural stimulation device or on the personal computing device.

Figure 10:
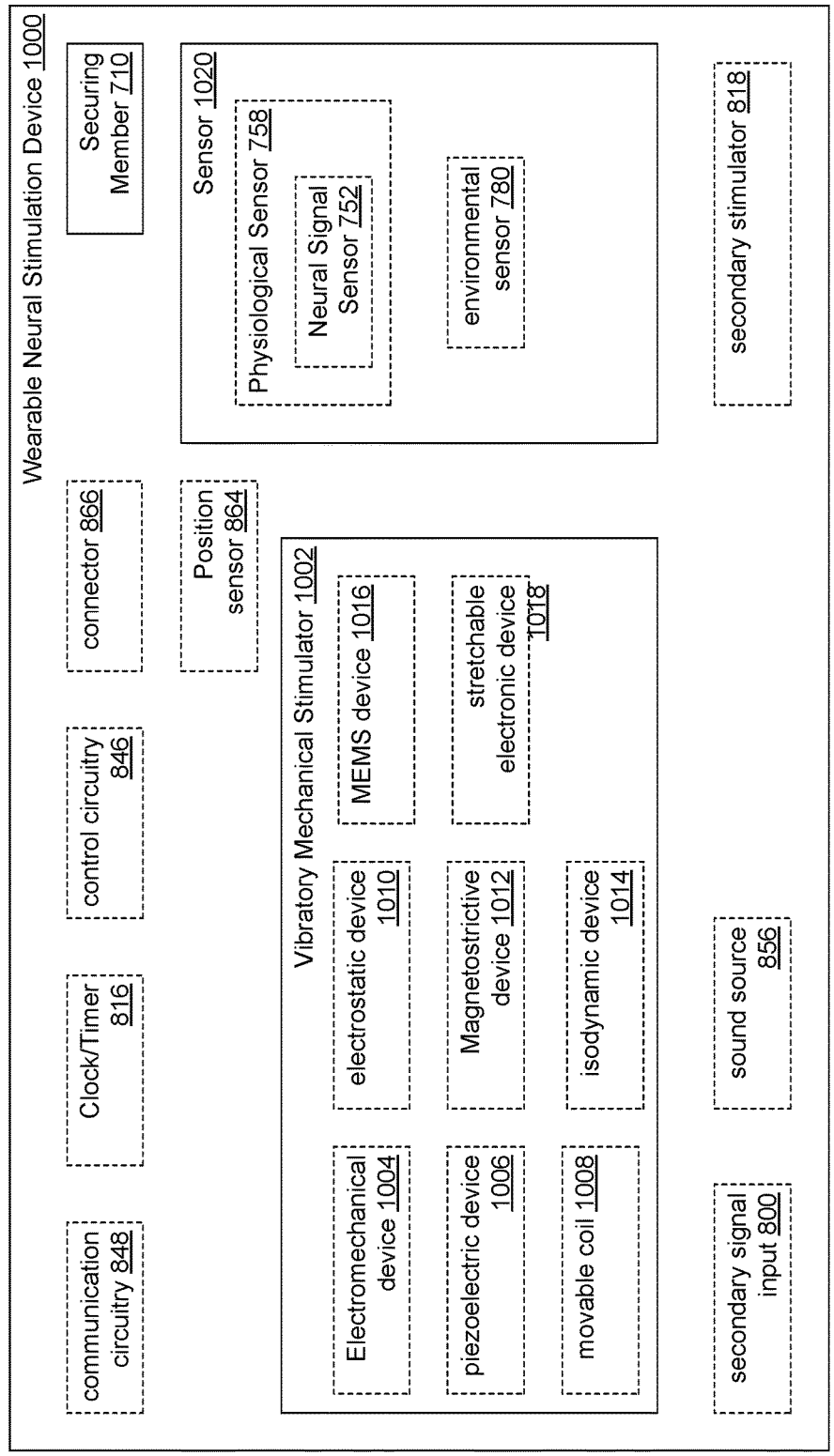
FIG. 10 is a block diagram of a neural stimulation device.

FIG. 10 depicts an embodiment of a wearable neural stimulation device 1000 that includes a vibratory mechanical stimulator 1002. Vibratory mechanical stimulator 1002 is adapted to produce a vibratory stimulus of sufficient frequency and amplitude to modulate the activity of at least one mechanoreceptor with a receptive field on at least a portion of a pinna of a subject, and a securing member 710 configured to secure vibratory mechanical stimulator 1000 to the pinna. Securing member 710 is as described herein above. Vibratory mechanical stimulator 1002 is a vibratory stimulator, such as vibratory stimulator 732 described generally in connection with FIG. 7. In various aspects, vibratory mechanical stimulator 1002 includes an electromechanical device 1004, piezoelectric device 1006, movable coil 1008, electrostatic device 1010, magnetostrictive device 1012, isodynamic device 1014, a MEMS device 1016, and/or a stretchable electronic device 1018.

In an aspect, neural stimulation device 1000 includes at least one sensor 1020, which may be any of the various types of sensors described in connection with secondary sensor 750 in FIG. 7, e.g., a physiological sensor 758, a neural signal sensor 752, an environmental sensor 780, a motion sensor 794 or a location sensor 796. In various aspects, neural stimulation device 1000 includes a secondary signal input 800, secondary stimulator 818, control circuitry 846 carried by securing member 710, communication circuitry 848, sound source 856, position sensor 864, and connector 866, all of which have been discussed in connection with FIG. 7.

Figure 11:
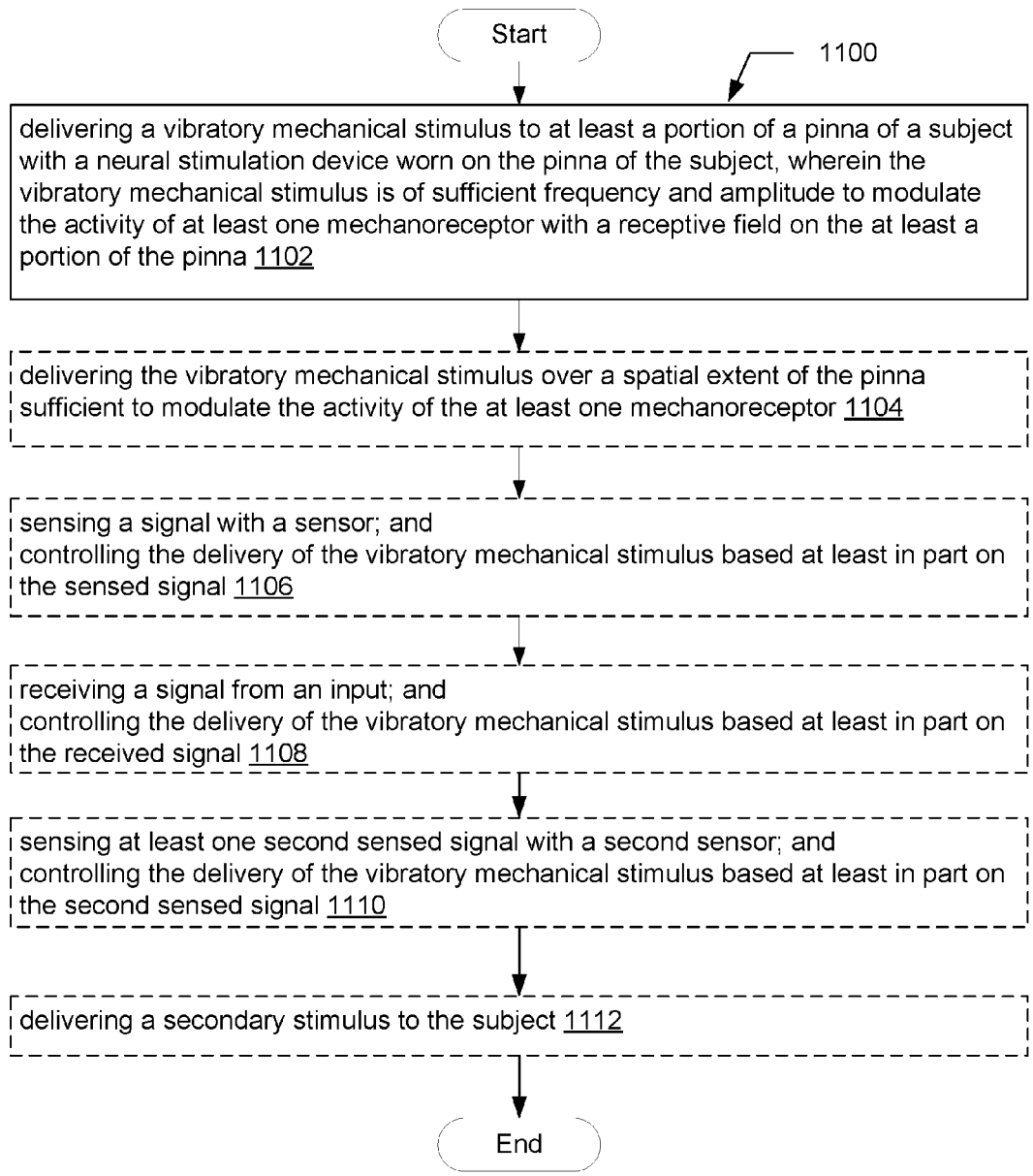
FIG. 11 is a flow diagram of a method.

FIG. 11 is a flow diagram of a method 1100 relating to use of a neural stimulation system as depicted in FIG. 10. In an aspect, method 1100 includes delivering a vibratory mechanical stimulus to at least a portion of a pinna of a subject with a neural stimulation device worn on the pinna of the subject, wherein the vibratory mechanical stimulus is of sufficient frequency and amplitude to modulate the activity of at least one mechanoreceptor with a receptive field on the at least a portion of the pinna, as indicated at 1102. In an aspect, method 1100 includes delivering the vibratory mechanical stimulus over a spatial extent of the pinna sufficient to modulate the activity of the at least one mechanoreceptor, as indicated at 1104.

In an aspect, the vibratory mechanical stimulus has a waveform sufficient to modulate the activity of the at least one mechanoreceptor with a receptive field on the at least a portion of the pinna. For example, the vibratory mechanical stimulus may have a sinusoidal or other waveform. In some aspects, the vibratory mechanical stimulus is delivered according to programmed pattern, which may include delivering the vibratory mechanical stimulus either continuously or intermittently.

In an aspect, as indicated at 1106, method 1100 includes sensing a signal with a sensor and controlling the delivery of the vibratory mechanical stimulus based at least in part on the sensed signal. The sensed signal may be any of the various types of signal sensed with sensor 1018 in FIG. 10. In various aspects, controlling delivery of the vibratory mechanical stimulus based at least in part on the sensed signal includes modulating delivery of the neural stimulus in response to the sensed signal, or delivering the vibratory mechanical stimulus in response to the sensed signal. In an aspect, controlling the delivery of the vibratory mechanical stimulus based at least in part on the sensed signal includes initiating delivery of the vibratory mechanical stimulus in response to the sensed signal.

In an aspect, method 1100 includes receiving a signal from an input and controlling the delivery of the vibratory mechanical stimulus based at least in part on the received signal, as indicated at 1108. The received signal may be e.g., any of the various types of input signals received at secondary signal input 800 in FIG. 10.

In an aspect, method 1100 includes sensing at least one second sensed signal with a second sensor and controlling the delivery of the vibratory mechanical stimulus based at least in part on the second sensed signal, as indicated at 1110.

In an aspect, method 1100 also includes delivering a secondary stimulus to the subject, as indicated at 1112, which may include delivering a secondary stimulus with a secondary stimulator 818, as described in connection with FIG. 7.

As discussed in connection with method 900, the vibratory mechanical stimulus can be delivered in response to detection of symptoms of a brain-related disorder, which may include, for example, a mental health disorder, depression, post-traumatic stress disorder, seasonal affective disorder, anxiety, headache, or epilepsy. In an aspect, method 1100 includes delivering the vibratory mechanical stimulus until symptoms of the brain-related disorder are no longer detected.

Figure 12:
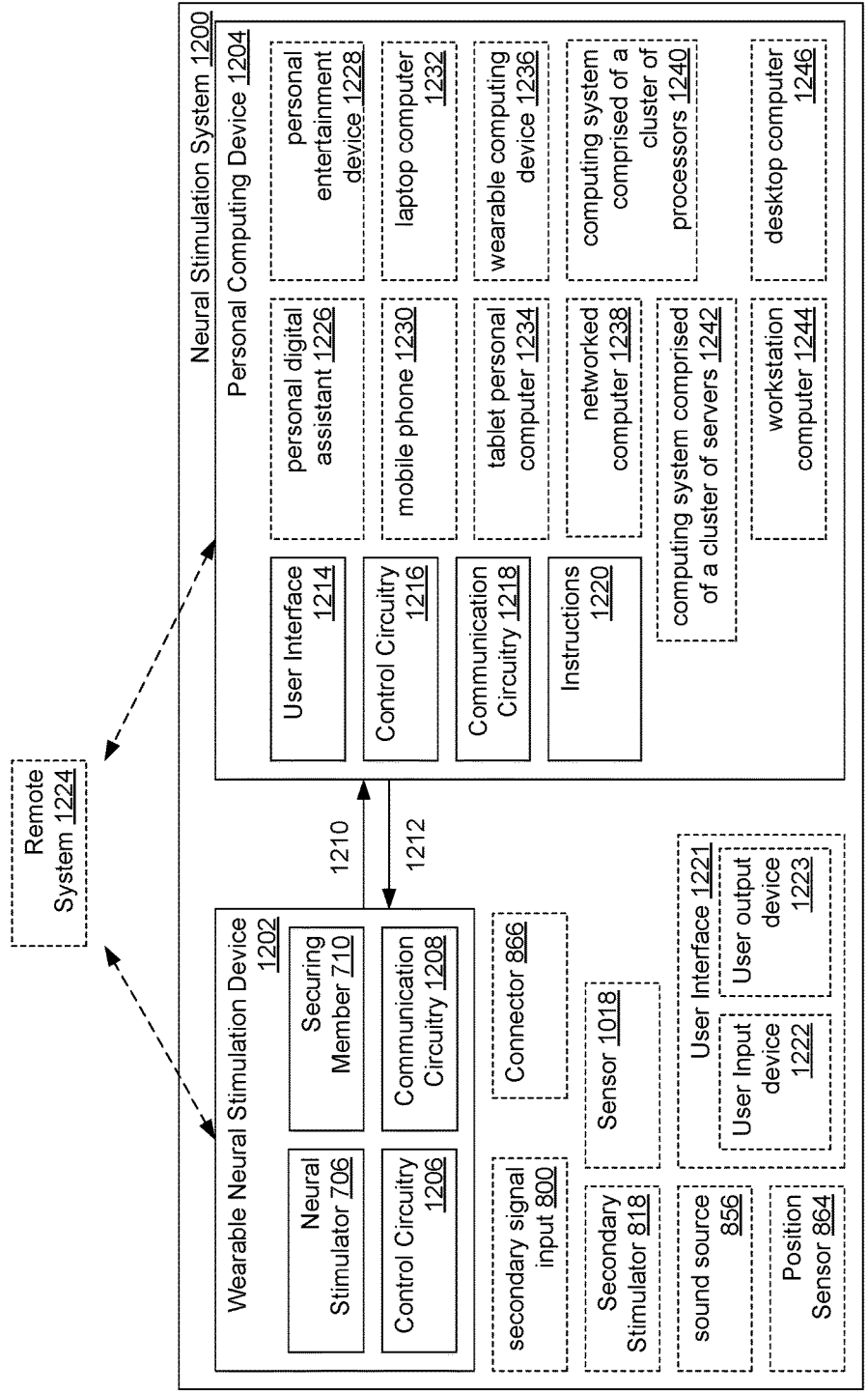
FIG. 12 is a block diagram of a neural stimulation system.

FIG. 12 depicts a neural stimulation system 1200 which includes a wearable neural stimulation device 1202 and personal computing device 1204. Personal computing device 1204 may be packaged separately from wearable neural stimulation device 1202, e.g., similar to the system depicted in FIGS. 2A and 2B. Wearable neural stimulation device 1202 includes neural stimulator 706, which is adapted to produce a stimulus for activating at least one sensory nerve fiber innervating at least a portion of a pinna of a subject, securing member 710 configured to secure the neural stimulator to the pinna, control circuitry 1206 for controlling operation of neural stimulator 706, and first communication circuitry 1208. Neural stimulator 706 and securing member 710 are as described herein above in connection with FIG. 7. Both control circuitry 1206 and first communication circuitry 1208 are incorporated into the wearable neural stimulation device 1202. First communication circuitry 1208 is operatively connected to control circuitry 1206 and is configured for at least one of sending a signal 1210 to and receiving a signal 1212 from personal computing device 1204. Other system components that may be included in or used in connection with wearable neural stimulation device 1202 include secondary signal input 800, secondary stimulator 818, sound source 856, position sensor 864 and connector 866, as described herein above in connection with FIG. 7, and sensor 1018 as described herein above in connection with FIG. 10. In an aspect, neural stimulation system 1200 includes user interface 1221, including user input device 1222 which is used to receive an input from the subject or other user, and user output device 1223. User input device 1222 may be any of various types of user input devices known to those of ordinary skill in the art, including but not limited to a button, keyboard, keypad, touchscreen, voice input, etc. In system 1200 and in other neural stimulation systems described herein, system components such as secondary signal input 800, secondary stimulator 818, sound source 856, position sensor 864, connector 866, sensor 1018, and user input device 1221 may in some cases be built into the wearable neural stimulation device (e.g., wearable neural stimulation device 1202) and in some cases be packaged separately but used in combination with the wearable neural stimulation device. For example, sensors may be located on the subject's body at a location other than the ear, or in the vicinity of the subject but not on the subject's body. In some cases, sensors may be implanted within the subject's body. Similarly, one or both of a secondary stimulator and a sound source can be located on the wearable neural stimulation device, on the subject's body distinct from the neural stimulation device, or in the vicinity of the subject but not on the subject's body.

Personal computing device 1202 includes a user interface 1214 for at least one of presenting information to and receiving information from a user, control circuitry 1216 operatively connected to user interface 1214, and second communication circuitry 1218 configured for at least one of sending a signal to and receiving a signal from the first communication circuitry 1208 carried by the housing of the wearable neural stimulation device. In addition, personal computing device 1202 includes instructions 1220 that when executed on personal computing device 1204 cause personal computing device 1204 to perform at least one of sending signal 1212 to and receiving signal 1210 from wearable neural stimulation device 1202 via second communication circuitry 1218.

Communication circuitry 1208 and communication circuitry 1218 provide for communication between wearable neural stimulation device 1202 and personal computing device 1204. In addition, in some aspects one or both of communication circuitry 1208 and communication circuitry 1218 provide for communication of wearable neural stimulation device 1202 or personal computing device 1204, respectively, with a remote system 1224. In some aspects, communication circuitry 1208 and communication circuitry 1218 provide for wired communication between wearable neural stimulation device and personal computing device 1204. Wired communication to wearable neural stimulation device may occur via connector 866. Alternatively, or in addition, a wireless communication link may be established between wearable neural stimulation device 1202 and personal computing device 1204, and/or between either wearable neural stimulation device 1202 or personal computing device 1204 and remote system 1224. In various aspects, a wireless communication link includes at least one of a radio frequency, wireless network, cellular network, satellite, WiFi, BlueTooth, Wide Area Network, Local Area Network, or Body Area Network communication link. Various types of communication links are suitable for providing communication between two remote locations. Communication between locations remote from each other may take place over telecommunications networks, for example public or private Wide Area Network (WAN). In general, communication between remote locations is not considered to be suitably handled by technologies geared towards physically localized networks, e.g., Local Area Network (LAN) technologies operation at Layer 1/2 (such as the forms of Ethernet or WiFi). However, it will be appreciated that portions (but not the entirety) of communication networks used in remote communications may include technologies suitable for use in physically localized network, such as Ethernet or WiFi.

In an aspect, personal computing device 1204 is personal digital assistant 1226, a personal entertainment device 1228, a mobile phone 1230, a laptop computer 1232, a tablet personal computer 1234, a wearable computing device 1236 (e.g., a fitness band, an item of clothing, attire, or eyewear incorporating computing capability), a networked computer 1238, a computing system comprised of a cluster of processors 1240, a computing system comprised of a cluster of servers 1242, a workstation computer 1244, and/or a desktop computer 1246. In various aspects, personal computing device 1204 includes one or more of a portable computing device, a wearable computing device, a mobile computing device, and a thin client computing device, for example.

Figure 13:
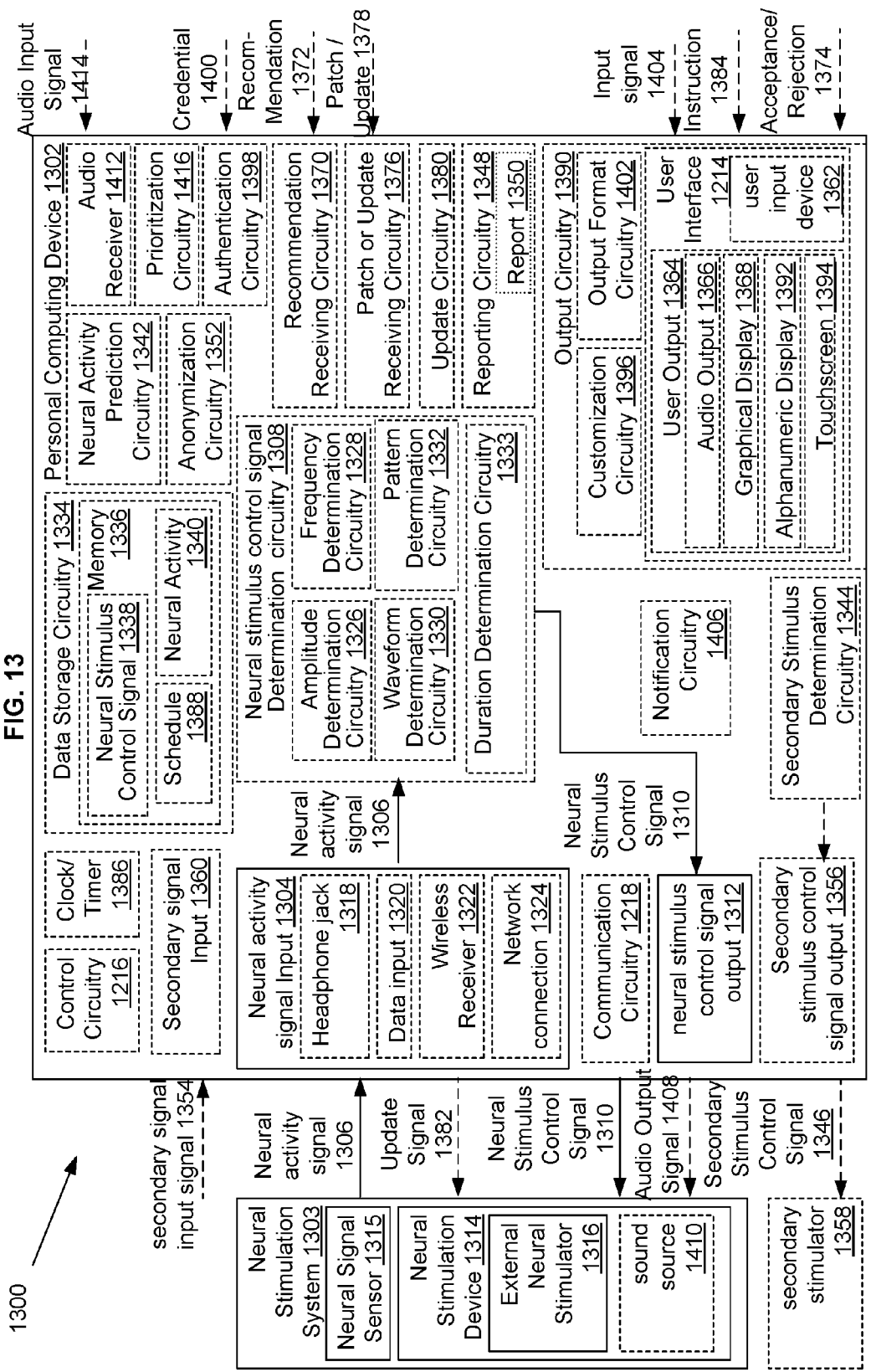
FIG. 13 is a block diagram of a system including a personal computing device.

FIG. 13 depicts aspects of a system 1300 including personal computing device 1302, for use in connection with neural stimulation system 1303, which is a neural stimulation system such as described herein above. Personal computing device 1302 is as described generally in connection with FIG. 12. In an aspect, personal computing device 1302 includes circuitry 1304 for receiving a neural activity signal 1306, circuitry 1308 for determining a neural stimulus control signal 1310 based at least in part on neural activity signal 1306, and circuitry 1312 for outputting neural stimulus control signal 1310 to neural stimulation device 1314. In an aspect, neural activity signal 1306 is sensed by neural signal sensor 1315, and is indicative of a physiological status of a subject. Neural activity signal 1306 may be an unprocessed neural signal, or neural activity signal 1306 may have been subjected to various types and amounts of signal processing, and/or analysis (including, but not limited to filtering, amplification, analog to digital conversion, signal averaging, conversion from time to frequency domain, feature extraction, and so forth). Neural activity signal 1306 may include neural activity sensed from one or more neural signal sensors 1315 (which may be electroencephalographic sensors or electrooculographic sensors, for example). Neural activity signal 1306 may include information derived from or associated with the sensed neural signal, and may include or be accompanied by additional information that identifies the type of signal, type of processing to which the signal has been subject, data formatting, device settings used during acquisition of the neural signal, etc. Neural signal sensor 1315 is a component of neural stimulation system 1303, and may be a component of neural stimulation device 1314, or used in association therewith, as described herein above. Neural stimulation device 1314 includes external neural stimulator 1316, which is configured to be carried on a pinna of the subject. Neural stimulus control signal 1310 is configured to control delivery of a neural stimulus by external neural stimulator 1316, the neural stimulus configured to activate at least one sensory nerve fiber innervating at least a portion of the pinna.

Neural activity signal input 1304 (the circuitry for receiving neural activity signal 1306) includes, for example, a headphone jack 1318, data input 1320, wireless receiver 1322, or network connection 1324. In various aspects neural activity signal input 1304 includes circuitry for receiving a signal from a body area network, a local area network, or a wide area network.

Neural stimulus control signal determination circuitry 1308 includes one or more of amplitude determination circuitry 1326 for determining a neural stimulus amplitude, frequency determination circuitry 1328 for determining a neural stimulus frequency, waveform determination circuitry 1330 for determining a neural stimulus waveform, pattern determination circuitry 1332 for determining a neural stimulus pattern, or duration determination circuitry 1333 for determining a neural stimulus duration. In an aspect, personal computing device 1302 includes data storage circuitry 1334 for storing data on the data storage device, including memory 1336 and circuitry for accessing data stored therein. Memory 1336 may contain stored preprogrammed stimulus patterns and waveforms as well as neural stimulus parameter values from which neural stimuli can be computed. In an aspect, system 1300 includes data storage circuitry 1334 for storing data on personal computing device 1302 representing neural stimulus control signal 1338. In an aspect, system 1300 includes data storage circuitry 1334 for storing data on personal computing device 1302 representing previous neural activity 1340. In an aspect, neural activity prediction circuitry 1342 predicts a future neural activity signal based on a previous neural activity signal.

In an aspect, system 1300 includes secondary stimulus determination circuitry 1344 for determining a secondary stimulus based on neural activity signal 1306. In an aspect, secondary stimulus determination circuitry 1344 determines the secondary stimulus control signal 1346 based on previous neural activity signal 1340.

In an aspect, system 1300 includes reporting circuitry 1348 for providing a report 1350 to at least one recipient. Reporting circuitry 1348 may cause report 1350 to be provided via a user interface 1214 (as described in connection with FIG. 12) or via a computing network (accessed via communication circuitry 1218). In an aspect, report 1350 is provided to the subject using the neural stimulation device 1314. In another aspect, report 1350 is provided to other parties, for example, a medical care provider, an insurance company, a service provider (e.g., a business or other entity that provides services related to the neural stimulation device or related to monitoring use of the neural stimulation device). In an aspect, report 1350 is provided to at least one social media contact (or 'friend'), or to a peer of the subject, e.g., via a social network. In an aspect, the recipient is a computing system, e.g. a computing system used for storing and/or processing healthcare information. In various aspects, anonymization circuitry 1352 is used to provide the report in anonymized form (e.g., with information identifying the subject removed therefrom). Reporting circuitry 1326 may include circuitry for including various information in report 1350, e.g., information relating to one or more of neural activity signal 1306 or information derived therefrom, neural stimulus control signal 1310, settings for neural stimulation device 1314 or personal computing device 1302, stored neural activity data 1340, secondary input signal 1354, and secondary stimulus control signal 1346. In an aspect, system 1300 includes secondary stimulus control signal output circuitry 1356 for delivering secondary stimulus control signal 1346 to secondary stimulator 1358. Secondary stimulator 1358 can be any type of stimulator, for example such as secondary stimulator 818 described in connection with FIG. 7.

In an aspect, system 1300 includes secondary signal input 1360 for receiving a secondary input signal 1354 at personal computing device 1302. In an aspect, neural stimulus control signal determination circuitry is configured to determine neural stimulus control signal 1310 based at least in part on secondary input signal 1354. Secondary input signal may be representative of a physiological parameter of the subject or an environmental parameter of the subject, and may include a signal sensed from a sensor on or associate with neural stimulation device 1314, or a sensor in the environment of the subject, and/or parameters or values derived from such sensed signals. In an aspect, the secondary input signal is indicative of a user input provided by the subject. In an aspect, secondary input signal 1354 may be received via user input 1362 in user interface 1214.

In an aspect, system 1300 includes circuitry for presenting a recommendation to the subject. The recommendation may be presented to the subject via user output 1364 of user interface 1214, e.g., via audio output 1366 and/or graphical display 1368 or transmitted to neural stimulation device 1303 and presented via a user interface on neural stimulation device 1303. In an aspect, system 1300 includes recommendation receiving circuitry 1370 for receiving recommendation 1372 at personal computing device 1302.

For example, in an aspect recommendation receiving circuitry 1370 receives recommendation 1372 via a computing network. In various aspects, recommendation 1372 is received from a medical care provider, from an insurance company, a service provider, an advisor, a computation-based system (including, e.g. an artificial intelligence), or a social media source, for example. In various aspects, recommendation receiving circuitry 1370 is configured to receive recommendations from particular sources, e.g. by receiving along with the recommendation a code indicating the source of the recommendation (e.g., a specific medical care provider, a medical care provider as opposed to a social media source), and to recognize a source of the recommendation and respond differently depending upon the source of the recommendation. Recommendation receiving circuitry 1370 may be configured such that recommendations from more credible sources may presented to the subject more promptly or more prominently, whereas recommendations from undesirable sources may be blocked, for example. Recommendation 1372 may relate to a configuration of neural stimulus control signal 1319 or secondary stimulus control signal 1346. In other aspects, recommendation 1372 relates to one or more of a consumer product, a service, a user experience, a user activity, or an organization that may be of interest to the subject, e.g., because the recommendations would enhance or be compatible with the effects of the neural stimulation received by the subject, or in some other manner relate to the neural stimulation or the condition which it is intended to treat. For example, the recommendation might be for software for storing, presenting, sharing, or reporting stimulation data or health data or for an organization that provides counseling to individuals with a particular condition. In an aspect, user input 1362 is configured to receive acceptance/rejection signal 1374 from the subject regarding acceptance or rejection of recommendation 1372.

In an aspect, system 1300 includes patch or update receiving circuitry 1376 for receiving patch/update 1378 at personal computing device 1302. Patch/update 1378 includes a software patch or update for software residing on personal computing device 1302 or neural stimulation device 1314 and may be received, for example, from the manufacturer of neural stimulation device 1314, from a service provider, or the like. In an aspect, personal computing device 1302 includes update circuitry 1380 for applying the patch or update to software installed on personal computing device 1302 or to software installed on neural stimulation device 1314, by sending update signal 1382 to neural stimulation system 1303. In an aspect, update circuitry 1380 also provides for updating a configuration of at least one of the neural stimulation device and the personal computing device, the configuration relating to operation of the neural stimulation device. In an aspect, update circuitry 1380 can be configured to update the configuration of at least one of the neural stimulation device and the personal computing device based on historical data (e.g., as stored in memory 1336). In another aspect, update circuitry 1380 is configured to update the configuration based on at least one instruction 1384. In an aspect, instruction 1384 is received via user input 1362 of personal computing device 1302. In another aspect, instruction 1384 is received from a computing network, (e.g., from a remote device or system, via a data input such as I/O 892 depicted in FIG. 8). In various aspects, instruction 1384 is received from a medical care provider, an insurance company, or a service provider, for example.

In another aspect, update circuitry 1380 is configured to update the configuration of at least one of the neural stimulation device and the personal computing device based on at least one recommendation 1372. As discussed herein above, recommendation 1372 is received by recommendation receiving circuitry 1370, and can be received from an advisor, from a computation-based system (e.g., an artificial intelligence, machine learning system, or search engine based on a data-driven technique), or from a social media source (for example, in various aspects, the recommendation is based on the at least one preference of at least one social media contact, peer, or role model of the subject). In addition, acceptance/rejection input 1374 is received from the subject by user interface 1214 regarding acceptance or rejection of the recommendation, and update circuitry 1380 updates the configuration responsive to acceptance of the recommendation by the subject (if the recommendation is rejected, no update is made in response to the recommendation). As an alternative, acceptance or rejection of the recommendation can be provided by a caregiver of the subject regarding received via either user interface 1214 or via a data input from a remote device or system. Update circuitry 1380 updates the configuration responsive to acceptance of the recommendation by the caregiver of the subject. In another aspect, update circuitry 1380 is configured to update the configuration of at least one of the neural stimulation device and the personal computing device based on an environmental parameter (based in a secondary input signal 1354 received at secondary signal input 1360. In another aspect, update circuitry 1380 is configured to update the configuration of at least one of the neural stimulation device and the personal computing device automatically. For example, in an aspect, the configuration is updated automatically according to a schedule, for example when the time and/or date indicated by clock/timer 1386 matches an update time/date in schedule 1388 stored in memory 1336.

In an aspect, neural activity signal input 1304 includes circuitry for receiving neural activity signal 1306 via a secure connection. In an aspect, neural control signal output 1312 includes circuitry for outputting neural stimulus control signal 1346 via a secure connection. The secure connection may include be provided through the use of an encrypted signal, for example.

In an aspect, system 1300 includes output circuitry 1390 for presenting information to the subject via user interface 1214, including e.g., audio output 1366, graphical display 1368, alphanumeric display 1392, touchscreen 1394, or other user interface devices, as known to those of ordinary skill in the art.

In an aspect, system 1300 includes customization circuitry 1396. Customization circuitry 1396 customizes for the subject one or both of the information, or the formatting of the information, that is presented to via user interface 1214, based on user preferences, for example.

In an aspect, system 1300 includes authentication circuitry 1398 for receiving a credential 1400 showing that the subject is an authorized user. In an aspect, output circuitry 1390 presents information to the subject via user interface 1214 only following receipt of credential 1400 showing that the subject is an authorized user. In various aspects, authentication circuitry 1398 receives a password, a personal identification number, a biometric feature, or a card authentication, for example.

In an aspect, output circuitry 1390 includes output format circuitry 1402 for presenting the information to the subject via user interface 1214 in a graphical format that mimics the graphical format of an audio player, in a graphical format that mimics the graphical format of a mobile phone, or in any other graphical format that mimics the graphical format of a familiar user interface. This permits the subject to use the neural stimulation device discretely, and present to observers the impression that the personal computing device is functioning as a mobile phone or audio player rather than being used in connection with a neural stimulation device. In an aspect, output circuitry 1390 changes or discontinues the presenting of information to the subject via the user interface in response to an input signal 1404. For example, output circuitry 1390 switches between a first graphical format and a second graphical format on user interface 1214 in response to input signal 1404. For example, the first graphical format may present information relating to the neural stimulus, while the second graphical format may mimic the format of a mobile phone or audio player. In an aspect, input signal 1404 is a user input signal, received for example via user interface 1214. In another aspect, input signal 1404 is a sensed environmental signal indicative of presence of another person (e.g., an audio input signal containing the detected voice of the other person, received via secondary input signal 1354). In an aspect, input signal 1404 is indicative of a time (e.g., a signal received from clock/timer 1386 on personal computing device 1302).

In an aspect, neural stimulus control signal determination circuitry 1308 modulates neural stimulus control signal 1310 in response to an override signal. For example, in an aspect override signal is input signal 1404 received via user input 1362. In an aspect, override signal is secondary input signal 1354, received via secondary signal input 1360. In an aspect, the override signal originates from a sensor that senses a physiological parameter, such as heart rate. In the event that the physiological parameter indicates an unsafe condition (e.g., the heart rate is too high or too low), the neural stimulus control signal determination circuitry 1308 modulates neural stimulus control signal 1310 to discontinue production of the neural stimulus. For example, in various aspects, the override signal originates from a sensor responsive to sensing a presence of a person other than the subject in the vicinity of the subject or responsive to sensing that the external neural stimulator is not properly positioned on the pinna of the subject. In an aspect, neural stimulus control signal determination circuitry 1308 modulates neural stimulus control signal 1310 to discontinue production of the neural stimulus. In an aspect, neural stimulus control signal determination circuitry 1308 modulates neural stimulus control signal 1310 to change an intensity of the neural stimulus. In addition to modulating or discontinuing the neural stimulus in response to an override condition (e.g., physiological parameter indicative of an unsafe condition, improper positioning of the external neural stimulator, etc.), a notification may be sent to the subject and/or to a medical care provider or other party regarding the override condition, to prompt the recipient of the notification to take corrective action, or for inclusion of the information in the subject's medical records.

In an aspect, secondary signal input 1360 is adapted to receive a position signal indicative of a position of the external neural stimulator with respect to the pinna of the subject. In connection therewith, system 1300 may also include notification circuitry 1406 for delivering a notification to the subject indicating that the external neural stimulator should be repositioned. In an aspect, notification circuitry 1406 includes circuitry for delivering the notification via a graphical display 1368 of personal computing device 1302. In an aspect, notification circuitry 1406 includes circuitry for delivering an auditory alert, either via audio output 1366 of personal computing device, or by generating an appropriate audio output signal 1408 for driving production of the auditory alert by a sound source 1410 on neural stimulation device 1314. In an aspect, notification circuitry 1406 includes circuitry for delivering a voice message (e.g., a preset message retrieved from memory 1336). In a further aspect, notification circuitry 1406 includes circuitry for storing information indicating that stimulator 1316 is improperly positioned in a data storage location (e.g., memory 1336) in personal computing device 1302. In another aspect, notification circuitry 1406 provides for storing information indicating that stimulator 1316 is improperly positioned in a data storage location in neural stimulation device 1314 (e.g., by transmitting such information to neural stimulation device 1314.

In an aspect, system 1300 includes circuitry for outputting an audio output signal, either via an audio output 1366 of personal computing device 1302 or via sound source 1410 of neural stimulation device 1314, where the audio output signal drives delivery of sound to the ear of the subject via a sound source. In an aspect, output circuitry 1390 is used to output the audio output signal via audio output 1366 of the personal computing device. In an aspect, communication circuitry 1218 is used for transmitting audio output signal 1408 to a sound source 1410 on neural stimulation device 1314. Alternatively, communication circuitry 1218 can be used to deliver an audio output signal to sound source distinct from the neural stimulation device (e.g., a sound source included in a device used by the subject, but not included in the neural stimulation device). In an aspect, output circuitry 1390 retrieves an audio signal from a data storage location (e.g., memory 1336) on personal computing device 1302, and generate audio output signal based on the retrieved audio signal. In another aspect, system 1300 includes audio receiver 1412 for receiving audio input signal 1414 from a telecommunication network. For example, in various aspects, audio input signal 1414 is a broadcast radio signal, a webcast audio signal, or a mobile phone signal.

In an aspect, system 1300 includes prioritization circuitry 1416 for prioritizing delivery of the neural stimulus control signal relative to the audio output signal (either audio output signal 1408 for delivery to sound source 1410, and/or an audio output signal delivered via audio output 1366 on personal computing device 1302). In an aspect, prioritization circuitry 1416 automatically discontinues outputting of the neural stimulus control signal 1310 and starts outputting of the audio output signal in response to receipt of audio input signal 1414. In another aspect, prioritization circuitry 1416 automatically declines audio input signal 1414 if the neural stimulus is currently being delivered. In another aspect, prioritization circuitry 1416 provides for circuitry for outputting the audio output signal simultaneously with neural stimulus control signal 1310. In another aspect prioritization circuitry 1416 provides for switching between outputting the audio output signal and outputting neural stimulus control signal 1346. Switching may occur in response to a user input received via user input 1362, or in response to sensor input received, for example, via secondary signal input 1360. In an aspect, prioritization circuitry 1416 performs switching between outputting the audio output signal and outputting neural stimulus control signal 1310 according to a schedule (stored, e.g., in memory 1336) in response to input from clock/timer 1386. In an aspect, prioritization circuitry 1416 switches between outputting the audio output signal and outputting the neural stimulus control signal responsive to receipt of the audio input signal 1414 from a telecommunication network. Prioritization circuitry 1416 may be configured to give higher priority to outputting of the neural stimulus control signal than to outputting of the audio output signal, or to give higher priority to outputting of the audio output signal than to outputting of the neural stimulus control signal. The priority of the signals may be determined by the preference of the subject. For example, the subject may consider it a higher priority to receive a phone call via his or her mobile phone than to continue received of a neural stimulation, and therefore may configure system 1300 so that neural stimulation is discontinued when a phone call is received. Alternatively, the subject may prefer that a neural stimulation session not be interrupted, and may configure system 1300 such that no phone calls will be received while neural stimulation is taking place. In other aspects, the subject may provide an input at user interface 1214 (e.g., by pressing a button) to switch between receiving neural stimulation and listening to music, as preferred. In another aspect, system 1300 is configured to deliver neural stimulation in combination with music.

Figure 14:
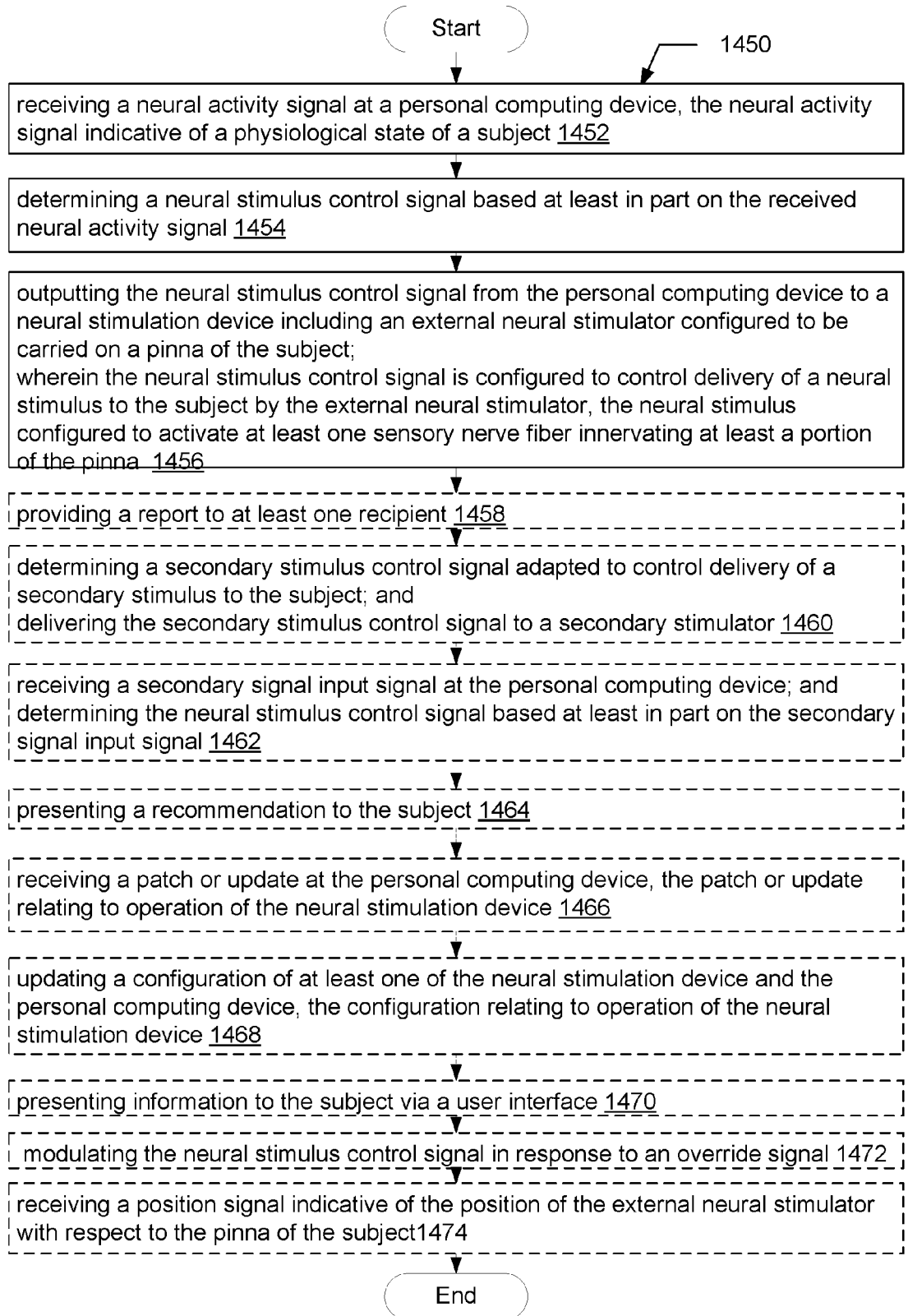
FIG. 14 is a flow diagram of a method.

FIG. 14 is a flow diagram of a method 1450 relating to use of a system including a personal computing device, as illustrated in FIG. 13. Method 1450 includes receiving a neural activity signal at a personal computing device, the neural activity signal indicative of a physiological status of a subject, as indicated at 1452. In addition, method 1450 includes determining a neural stimulus control signal based at least in part on the neural activity signal, as indicated at 1454, and outputting the neural stimulus control signal from the personal computing device to a neural stimulation device including an external neural stimulator configured to be carried on a pinna of the subject, wherein the neural stimulus control signal is configured to control delivery of a neural stimulus by the external neural stimulator, the neural stimulus configured to activate at least one sensory nerve fiber innervating at least a portion of the pinna, as indicated at 1456. In an aspect, determining the neural stimulus control signal includes determining a stimulation pattern. In various aspect, method 1450 includes additional steps, relating to the system functions described in greater detail in connection with FIG. 13. For example, in an aspect, method 1450 includes providing a report to at least one recipient, as indicated at 1458. In an aspect, method 1450 includes determining a secondary stimulus control signal adapted to control delivery of a secondary stimulus to the subject, and delivering the secondary stimulus control signal to a secondary stimulator, as indicated at 1460. For example, in an aspect, the secondary stimulator includes a game device, and the secondary stimulus control signal controls operation of the game device. In another aspect, the secondary stimulator includes computing system configured to deliver a virtual therapist experience, and the secondary stimulus control signal controls operation of the virtual therapist. In another aspect, the secondary stimulus includes an interactive activity delivered via a computing device, and the secondary stimulus control signal controls operation of the computing device.

In an aspect, method 1450 includes receiving a secondary input signal at the personal computing device and determining the neural stimulus control signal based at least in part on the secondary input signal, as indicated at 1462. For example, in an aspect the secondary input signal is indicative of a user input provided spontaneously by subject. Other secondary input signals are described herein above.

In an aspect, method 1450 includes presenting a recommendation to the subject, as indicated at 1464. Method 1450 may also include receiving the recommendation at the personal computing device, as described above in connection with FIG. 13.

In an aspect, method 1450 includes receiving a patch or update at the personal computing device, the patch or update relating to operation of the neural stimulation device, as indicated at 1466. In an aspect, the patch or update is for software installed on the personal computing device. In another aspect, the patch or update is for software installed on the neural stimulation device, in which case method 1450 may also include sending the patch or update to the neural stimulation device.

In an aspect, method 1450 includes updating a configuration of at least one of the neural stimulation device and the personal computing device, the configuration relating to operation of the neural stimulation device, as indicated at 1468. As discussed above, the configuration is updated based on at least one instruction. In another aspect, the configuration is updated based on at least one recommendation, responsive to receipt of an input regarding acceptance of the recommendation by the subject or a caregiver of the subject.

In an aspect, method 1450 includes presenting information to the subject via a user interface, as indicated at 1470. The method may also include changing or discontinuing the presenting of information to the subject via the user interface in response to an input signal. In an aspect, method 1450 includes modulating the neural stimulus control signal in response to an override signal, as indicated at 1472.

In an aspect, method 1450 includes receiving a position signal indicative of the position of the external neural stimulator with respect to the pinna of the subject, as indicated at 1474. Method 1450 may also include delivering a notification to the subject indicating that external neural stimulator should be repositioned. Other method aspects are discussed in connection with FIG. 13.

Figure 15:
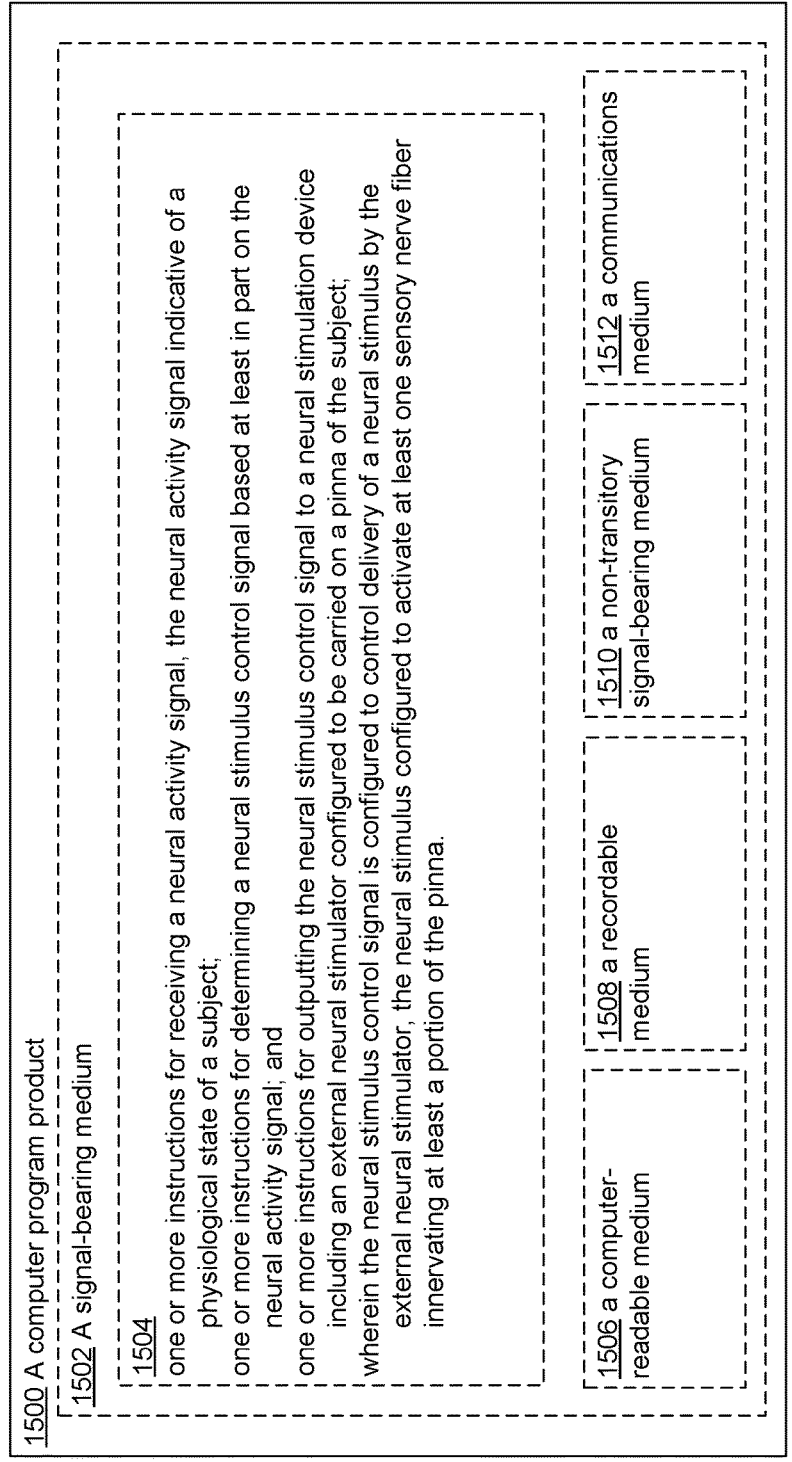
FIG. 15 is a block diagram of a computer program product relating to the method of FIG. 14.

FIG. 15 is a block diagram of a computer program product 1500 for implementing a method as described in connection with FIG. 14. Computer program product 1500 includes a signal-bearing medium 1502 bearing one or more instructions for receiving a neural activity signal, the neural activity signal indicative of a physiological status of a subject; one or more instructions for determining a neural stimulus control signal based at least in part on the neural activity signal; and one or more instructions for outputting the neural stimulus control signal to a neural stimulation device including an external neural stimulator configured to be carried on a pinna of the subject, wherein the neural stimulus control signal is configured to control delivery of a neural stimulus by the external neural stimulator, the neural stimulus configured to activate at least one sensory nerve fiber innervating at least a portion of the pinna, as indicated at 1504. Signal-bearing medium 1502 may be, for example, a computer-readable medium 1506, a recordable medium 1508, a non-transitory signal-bearing medium 1510, or a communications medium 1512, examples of which are described herein above.

Figure 16:
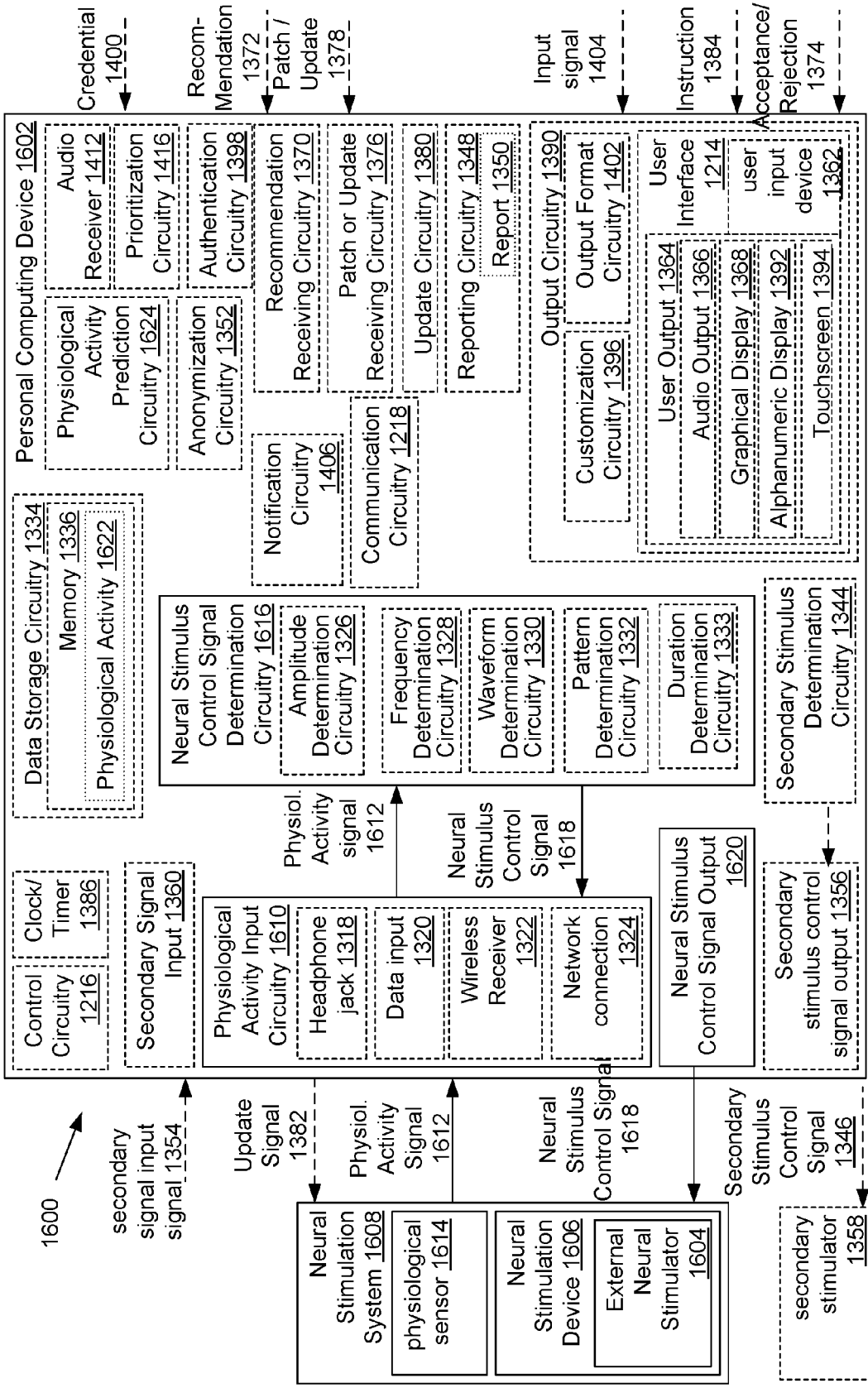
FIG. 16 is a block diagram of a system including a personal computing device.

FIG. 16 is a block diagram of a system 1600 including a personal computing device 1602 and external neural stimulator 1604, which comprises a part of neural stimulation device 1606 and neural stimulation system 1608. Personal computing device 1602 is as described generally in connection with FIG. 12. In an aspect, a system 1600 includes personal computing device 1602 including physiological activity input circuitry 1610 for receiving a physiological activity signal 1612 at personal computing device 1062. Physiological activity signal 1612 is sensed by physiological sensor 1614 in neural stimulation system 1608, and is indicative of a physiological status of a subject. Physiological sensor 1614 can be any of various types of physiological sensors, e.g., as described in connection with physiological sensor 758 in FIG. 7. In various aspects, physiological activity signal 1612 is representative of a heart rate (and in some cases heart rate rhythm variability), a blood pressure, perspiration, skin conductivity, respiration, pupil dilation, digestive tract activity, or piloerection. In some aspects, physiological activity signal 1612 is a neural activity signal, such as an electroencephalographic or electrooculographic signal. Physiological activity signal 1612 may be an electromyographic signal (indicative of muscle activity of the subject) or an electrocardiographic signal (indicative of cardiac activity of the subject). Physiological activity signal 1612 may be an unprocessed physiological signal, or physiological activity signal 1612 may have been subjected to various types and amounts of signal processing, and/or analysis (including, but not limited to filtering, amplification, analog to digital conversion, signal averaging, conversion from time to frequency domain, feature extraction, and so forth). Physiological activity signal 1612 may include activity sensed from one or more physiological sensors 1614. Physiological activity signal 1612 may include information derived from or associated with the sensed physiological signal, and may include or be accompanied by additional information that identifies the type of signal, type of processing to which the signal has been subject, data formatting, device settings used during acquisition of the physiological signal, etc. Personal computing device 1602 also includes neural stimulus control signal determination circuitry 1616 for determining neural stimulus control signal 1618 based at least in part on physiological activity signal 1612. Neural stimulus control signal 1618 is configured to control delivery of a neural stimulus by external neural stimulator 1604. In an aspect, the neural stimulus is configured to activate at least one sensory nerve fiber innervating at least a portion of the pinna. Personal computing device 1602 also includes neural stimulus control signal output circuitry 1620 for outputting neural stimulus control signal 1618 from personal computing device 1602 to neural stimulation device 1606. Neural stimulation device 1606 includes external neural stimulator 1604 configured to be carried on a pinna of the subject. Personal computing device 1602 also includes output circuitry 1390 for presenting information to the subject via user interface 1364 (as described herein above in connection with FIG. 13). Various elements of system 1600 are the same as like-numbered elements of the systems shown in FIG. 12 or 13, and accordingly will not be discussed in detail again in connection with FIG. 16. However, some components of system 1600 include different and/or additional features. For example, data storage circuitry 1334 is also adapted for storing physiological activity data 1622 representing physiological activity signal 1612 in memory 1336. In an aspect, physiological activity prediction circuitry 1624 predicts a future physiological activity signal based on a previous physiological activity signal. In addition, neural stimulus control signal determination circuitry 1616 determines the neural stimulus based on a previous physiological activity signal. Secondary stimulus determination circuitry 1344 is adapted to determine the secondary stimulus based on physiological activity signal 1612 or a previous physiological activity signal (e.g., stored in memory 1336). As noted above in connection with FIG. 13, in an aspect, secondary input signal 1354 is a physiological signal. It will be appreciated that secondary input signal 1354 in this context will be a secondary physiological signal, and physiological activity signal 1612 will be a primary physiological signal. In an aspect, physiological activity input circuitry 1610 includes circuitry for receiving physiological activity signal 1612 via a secure connection. In an aspect, neural stimulus control signal output 1620 includes circuitry for outputting neural stimulus control signal 1618 via a secure connection.

Figure 17:
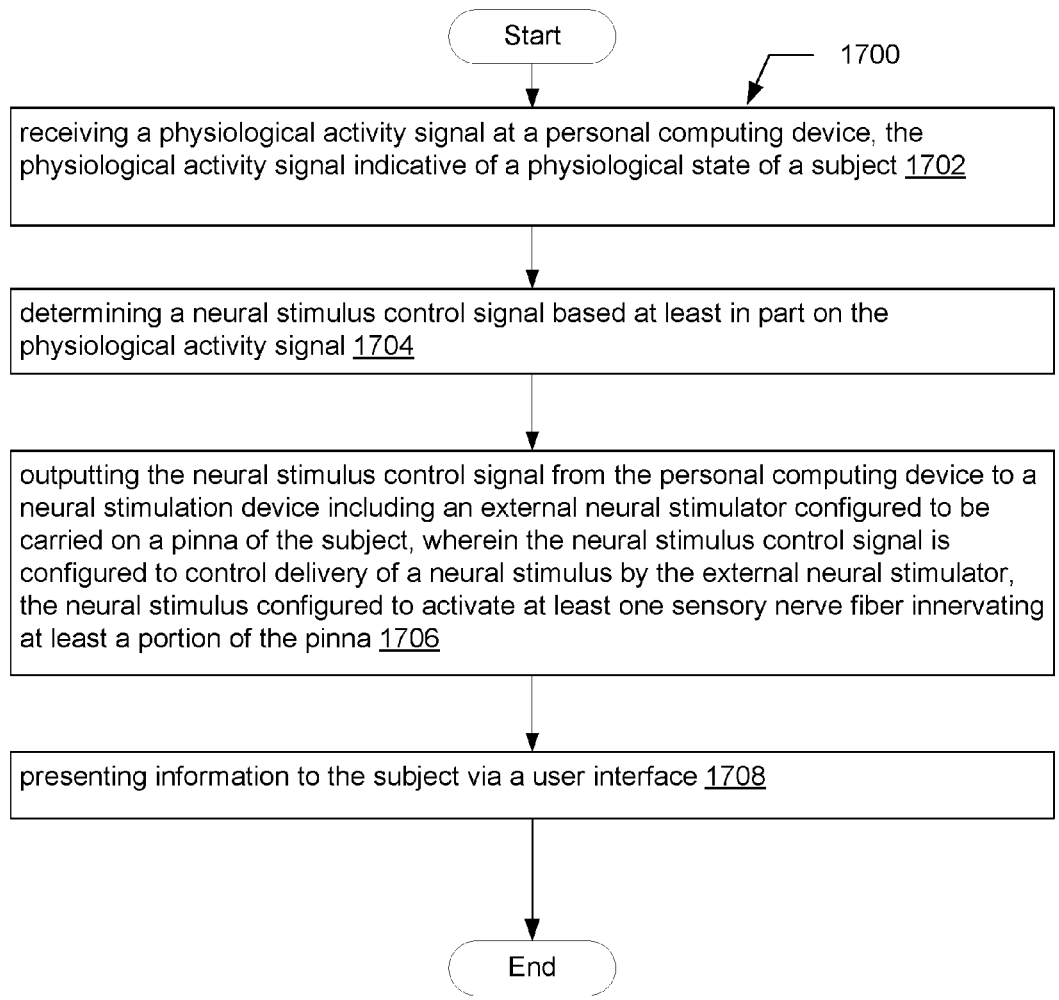
FIG. 17 is a flow diagram of a method.

FIG. 17 is a flow diagram of a method 1700 relating to use of a system as depicted in FIG. 16. In an aspect, method 1700 includes receiving a physiological activity signal at a personal computing device, the physiological activity signal indicative of a physiological status of a subject, as indicated at 1702; determining a neural stimulus control signal based at least in part on the physiological activity signal, as indicated at 1704; outputting the neural stimulus control signal from the personal computing device to a neural stimulation device including an external neural stimulator configured to be carried on a pinna of the subject, wherein the neural stimulus control signal is configured to control delivery of a neural stimulus by the external neural stimulator, the neural stimulus configured to activate at least one sensory nerve fiber innervating at least a portion of the pinna, as indicated at 1706; and presenting information to the subject via a user interface, as indicated at 1708. Other method aspects are discussed in connection with FIGS. 14 and 16.

Figure 18:
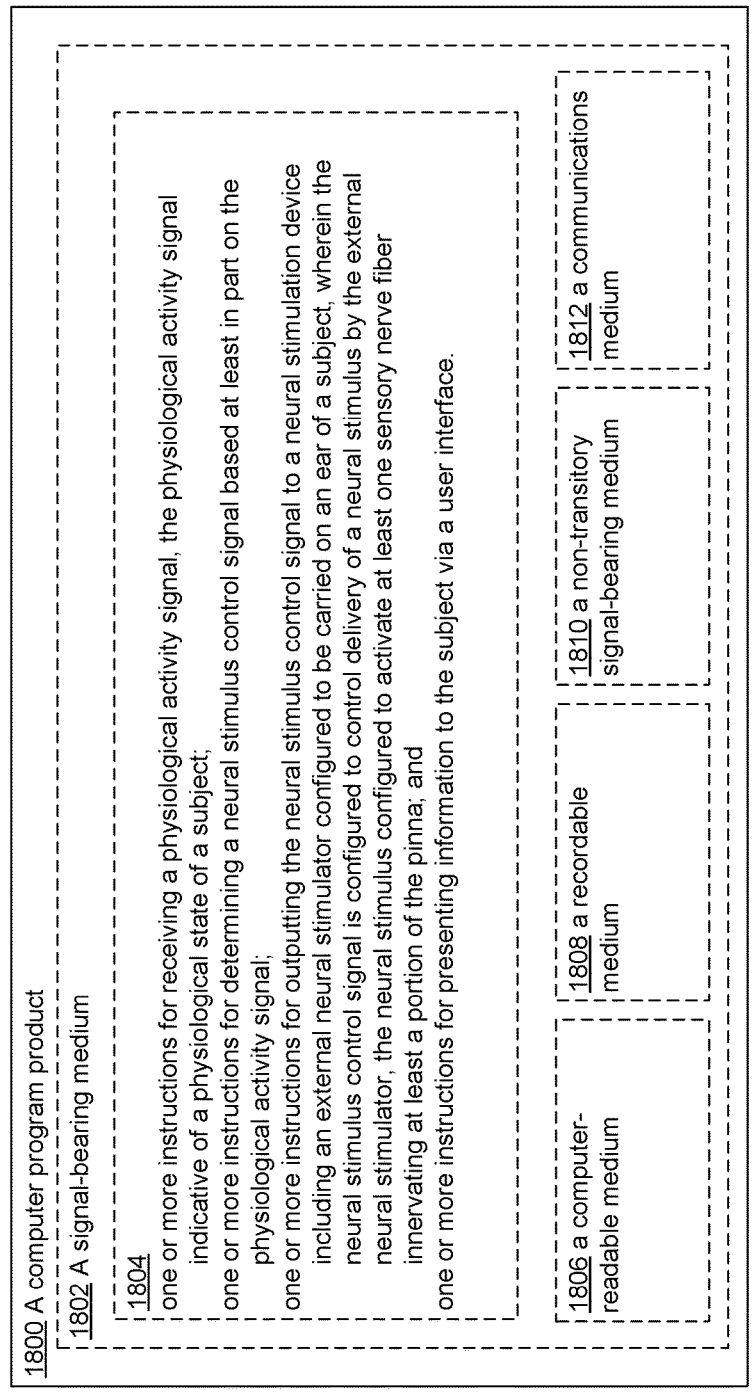
FIG. 18 is a block diagram of a computer program product relating to the method of FIG. 17.

FIG. 18 is a block diagram of a computer program product 1800 for implementing a method as described in connection with FIG. 17. Computer program product 1800 includes a signal-bearing medium 1802 bearing one or more instructions for receiving a physiological activity signal, the physiological activity signal indicative of a physiological status of a subject; one or more instructions for determining a neural stimulus control signal based at least in part on the physiological activity signal; one or more instructions for outputting the neural stimulus control signal to a neural stimulation device including an external neural stimulator configured to be carried on an ear of a subject, wherein the neural stimulus control signal is configured to control delivery of a neural stimulus by the external neural stimulator, the neural stimulus configured to activate at least one sensory nerve fiber innervating at least a portion of the pinna; and one or more instructions for presenting information to the subject via a user interface, as indicated at 1804. Signal-bearing medium 1802 may be, for example, a computer-readable medium 1806, a recordable medium 1808, a non-transitory signal-bearing medium 1810, or a communications medium 1812, examples of which are described herein above.

Figure 19:
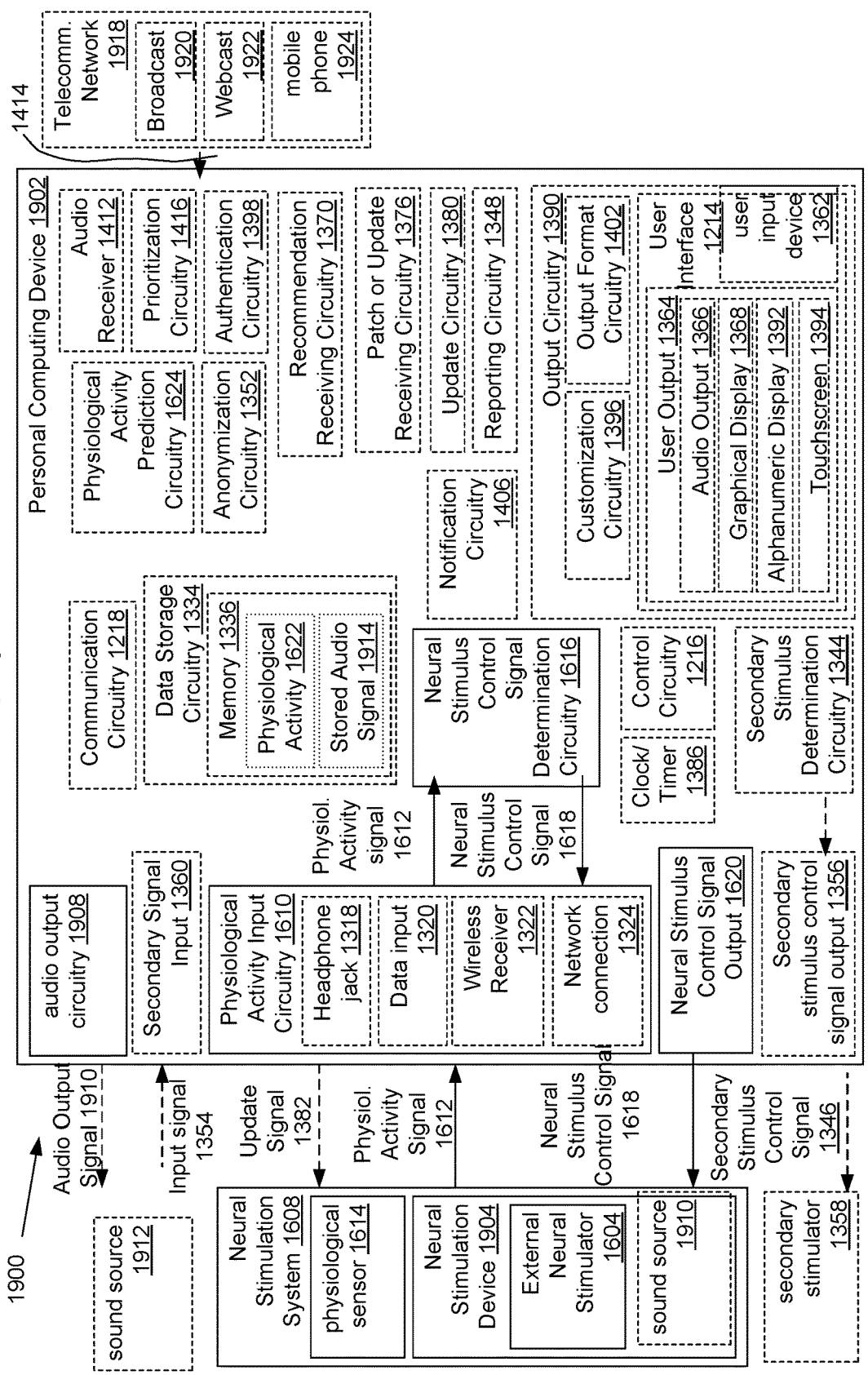
FIG. 19 is a block diagram of a system including a personal computing device.

FIG. 19 is a block diagram of a system 1900. FIG. 19 is similar to the system depicted in FIGS. 13 and 16, and like-numbered system components described in connection with these figures will not be described again in connection with FIG. 19. In an aspect, system 1900 includes a personal computing device 1902 including physiological activity input circuitry 1610 for receiving a physiological activity signal at personal computing device 1902, the physiological activity signal 1612 indicative of a physiological status of a subject. System 1900 also includes neural stimulus control signal determination circuitry 1616 for determining a neural stimulus control signal 1618 based at least in part on physiological activity signal 1612. In addition, system 1900 includes neural stimulus control signal output circuitry 1620 for outputting neural stimulus control signal 1618 from personal computing device 1902 to neural stimulation device 1904. Neural stimulation device 1904 includes external neural stimulator 1604 configured to be carried on a pinna of the subject, wherein neural stimulus control signal 1618 is configured to control delivery of a neural stimulus by the external neural stimulator, the neural stimulus configured to activate at least one sensory nerve fiber innervating at least a portion of the pinna. System 1900 also includes audio output circuitry 1908 for outputting an audio output signal 1910 via an audio output 1366 of personal computing device 1902. In an aspect, system 1900 includes circuitry for delivering the audio output signal to sound source 1910 on neural stimulation device. In another aspect, system 1900 includes circuitry for delivering audio output signal 1910 to sound source 1912 that is distinct from neural stimulation device 1904. For example, sound source 1912 may be a sound source in the environment of the subject but not on the neural stimulation device, including but not limited to a sound source on, built into, or associated with personal computing device 1902. In an aspect, system 1900 includes data storage circuitry 1334 for retrieving stored audio signal 1914 from a data storage location (memory 1336) on personal computing device 1902. In an aspect, system 1900 includes audio receiver 1412 for receiving the audio input signal from telecommunication network 1918. For example, in various aspects, the audio input signal is a broadcast radio signal 1920, a webcast audio signal 1922, or a mobile phone signal 1024.

In an aspect, system 1900 includes prioritization circuitry 1416 which prioritizes between delivery of neural stimulus and delivery of the audio output signal, based upon system settings and/or preferences of the subject. For example, prioritization circuitry 1416 provides for automatically discontinuing outputting of the neural stimulus control signal and starting outputting of the audio output signal in response to receipt of the audio input signal, automatically declining the audio input signal if the neural stimulus is currently being delivered, or outputting the audio output signal simultaneously with the neural stimulus control signal. In other aspects, prioritization circuitry 1416 provides switching between outputting the audio output signal and outputting the neural stimulus control signal, for example in response to a user input or a sensor input, according to a schedule, or in response to receipt of an audio input signal (e.g., a phone call) from a telecommunication network. Depending on preference of the subject or other considerations, prioritization circuitry 1416 can be configured to give higher priority to outputting of the neural stimulus control signal than to outputting of the audio output signal, or to give higher priority to outputting of the audio output signal than to outputting of the neural stimulus control signal.

Figure 20:
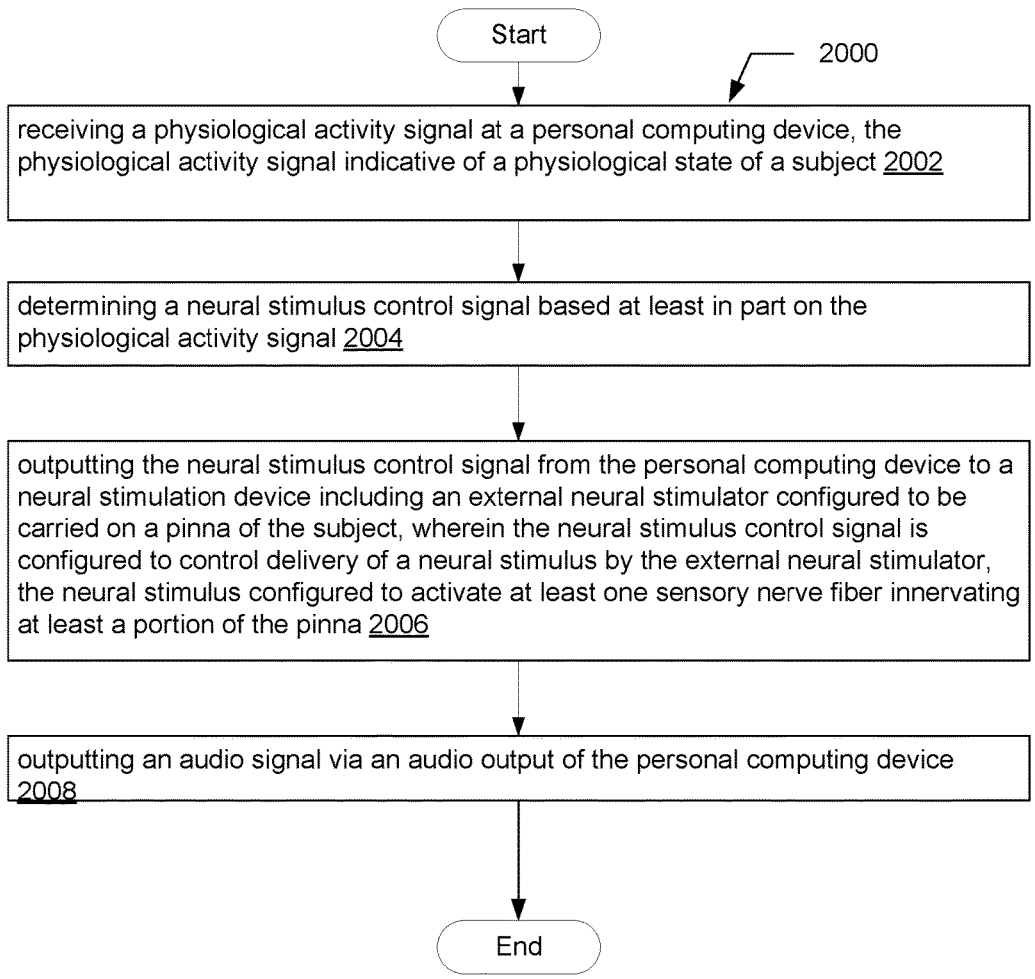
FIG. 20 is a flow diagram of a method.

FIG. 20 is a flow diagram of a method 2000 relating to use of a system as depicted in FIG. 19. In an aspect, method 2000 includes receiving a physiological activity signal at a personal computing device, the physiological activity signal indicative of a physiological status of a subject, as indicated at 2002; determining a neural stimulus control signal based at least in part on the physiological activity signal, as indicated at 2004; outputting the neural stimulus control signal from the personal computing device to a neural stimulation device including an external neural stimulator configured to be carried on a pinna of the subject, wherein the neural stimulus control signal is configured to control delivery of a neural stimulus by the external neural stimulator, the neural stimulus configured to activate at least one sensory nerve fiber innervating at least a portion of the pinna, as indicated at 2006; and outputting an audio output signal via an audio output of the personal computing device, as indicated at 2008. Other method aspects are discussed in connection with FIGS. 14 and 19.

Figure 21:
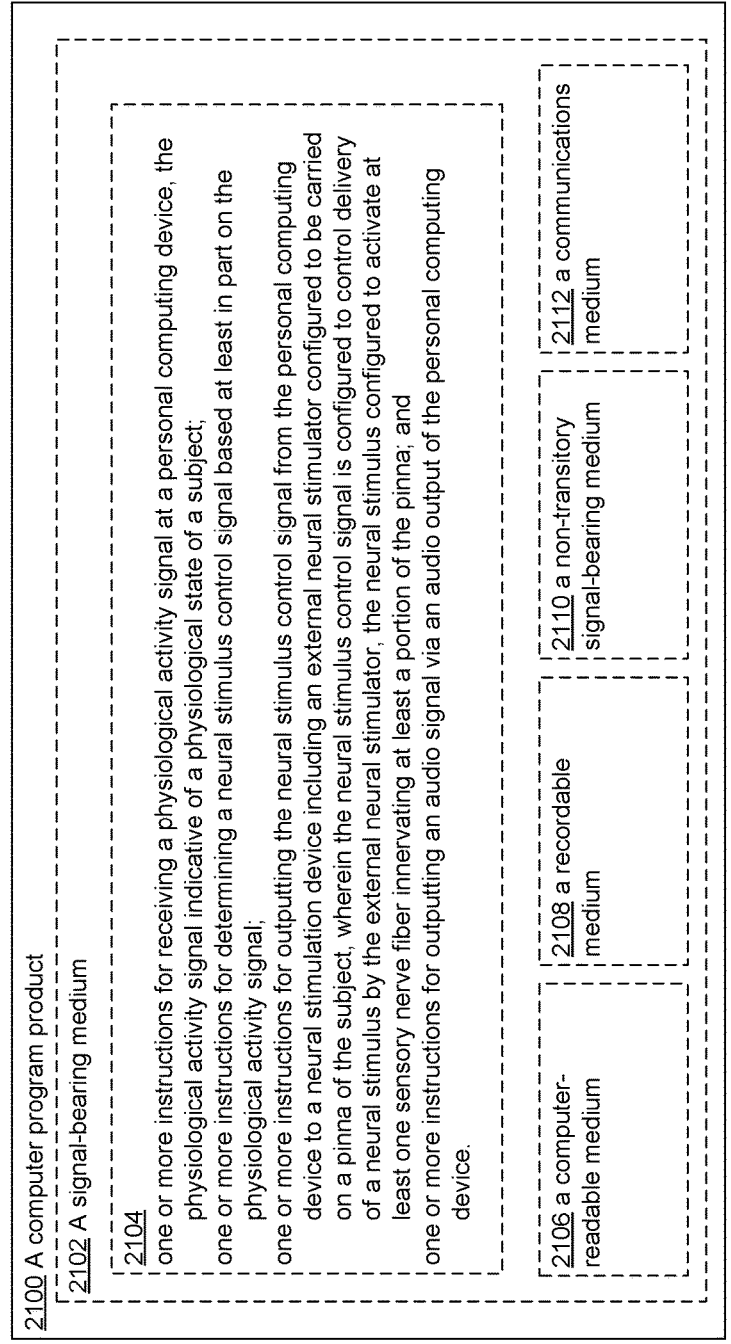
FIG. 21 is a block diagram of a computer program product relating to the method of FIG. 20.

FIG. 21 is a block diagram of a computer program product 2100 for implementing a method as described in connection with FIG. 20. Computer program product 2100 includes a signal-bearing medium 2102 bearing one or more instructions for receiving a physiological activity signal at a personal computing device, the physiological activity signal indicative of a physiological status of a subject, one or more instructions for determining a neural stimulus control signal based at least in part on the physiological activity signal, one or more instructions for outputting the neural stimulus control signal from the personal computing device to a neural stimulation device including an external neural stimulator configured to be carried on a pinna of the subject, wherein the neural stimulus control signal is configured to control delivery of a neural stimulus by the external neural stimulator, the neural stimulus configured to activate at least one sensory nerve fiber innervating at least a portion of the pinna, and one or more instructions for outputting an audio output signal via an audio output of the personal computing device, as indicated at 2104. Signal-bearing medium 2102 may be, for example, a computer-readable medium 2106, a recordable medium 2108, a non-transitory signal-bearing medium 2110, or a communications medium 2112, examples of which are described herein above.

Figure 22:
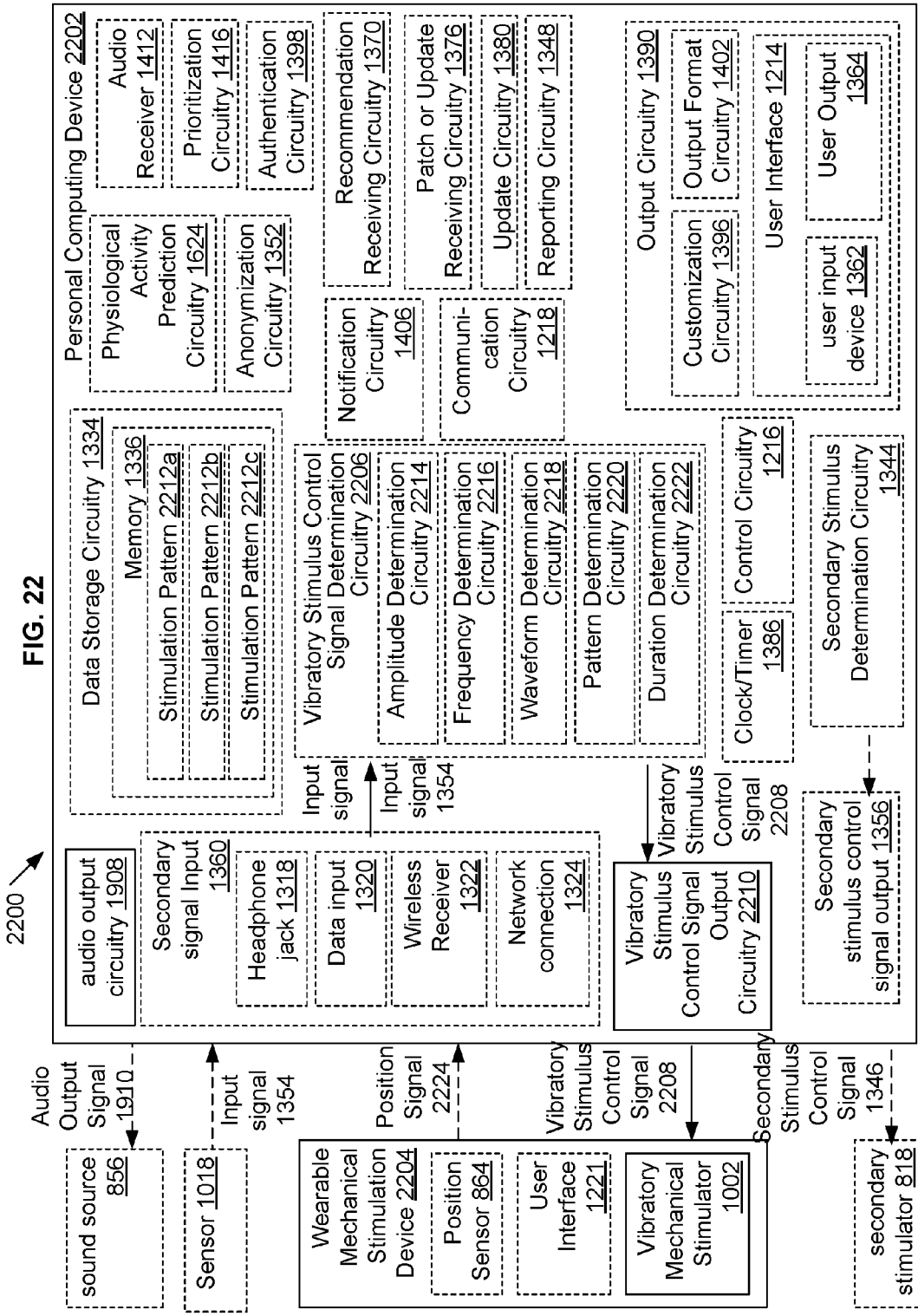
FIG. 22 is a block diagram of a system including a personal computing device.

FIG. 22 is a block diagram of a system 2200, which includes a personal computing device 2202 for use in combination with a wearable mechanical stimulation device 2204. FIG. 22 is similar to the systems depicted in FIGS. 13, 16 and 19 and like-numbered system components described in connection with these figures will not be described again in connection with FIG. 22. Personal computing device 2202 includes vibratory stimulus control signal determination circuitry 2206 for determining a vibratory stimulus control signal 2208, and vibratory stimulus control signal output circuitry 2210 for outputting vibratory stimulus control signal 2208 to wearable mechanical stimulation device 2204. Wearable mechanical stimulation device 2204 includes a vibratory mechanical stimulator 1002 configured to be carried on a pinna of a subject, wherein the vibratory stimulus control signal is configured to control delivery of a vibratory stimulus by the vibratory mechanical stimulator 1002, the vibratory stimulus configured to activate at least one mechanoreceptor with a receptive field on at least a portion of the pinna. In an aspect, wearable mechanical stimulation device 2204 is a wearable neural stimulation device 1000 of the type discussed in connection with FIG. 10, and can be considered a variant of wearable neural stimulation device 1202 depicted and discussed in connection with FIG. 12. In addition, in various aspects system 2200 includes additional components such as are included in neural stimulation system 1200 described in connection with FIGS. 7, 10 and/or 12, including, but not limited to, sensor 1018 for detecting input signal 1354, user interface 1221, position sensor 864, secondary stimulator 818, and sound source 856. Personal computing device 2202 can be any of the various types of personal computing devices described in connection with FIG. 12, for example, a personal digital assistant, a personal entertainment device, a mobile phone, a laptop computer, a table personal computer, a wearable computing device, a networked computer, a computing system comprised of a cluster of processors, a computing system comprised of a cluster of servers, a workstation computer, or a desktop computer. Data storage circuitry 1334 including memory 1336 on personal computing device 2202 can be used to store data, instructions, parameters, as described elsewhere herein, including but not limited to stimulation patterns 2212a, 2212b, and 2212c representing vibratory mechanical stimuli to be delivered under the control of vibratory stimulus control signal 2208. In an aspect, vibratory stimulus control signal 2208 is configured to cause delivery of one of a plurality of pre-programmed stimulation patterns, e.g., selected from stimulation patterns 2212a, 2212b, and 2212c stored in memory 1336. In an aspect, vibratory stimulus control signal 2208 is determined by vibratory stimulus control signal determination circuitry 2206. In various aspects, vibratory stimulus control signal determination circuitry 2206 includes amplitude determination circuitry 2214, frequency determination circuitry 2216, waveform determination circuitry 2218, pattern determination circuitry 2220, or duration determination circuitry 2222 for determining various aspects of the vibratory stimulus control signal 2208, which determines the mechanical stimulus delivered by vibratory mechanical stimulator 1002. If position signal 2224 from position sensor 864 indicates that vibratory mechanical stimulator 1002 is not properly positioned on the ear of the subject, a notification is provided to the subject, e.g., via notification circuitry 1406, instructing the subject to reposition vibratory mechanical stimulator 1002.

Figure 23:
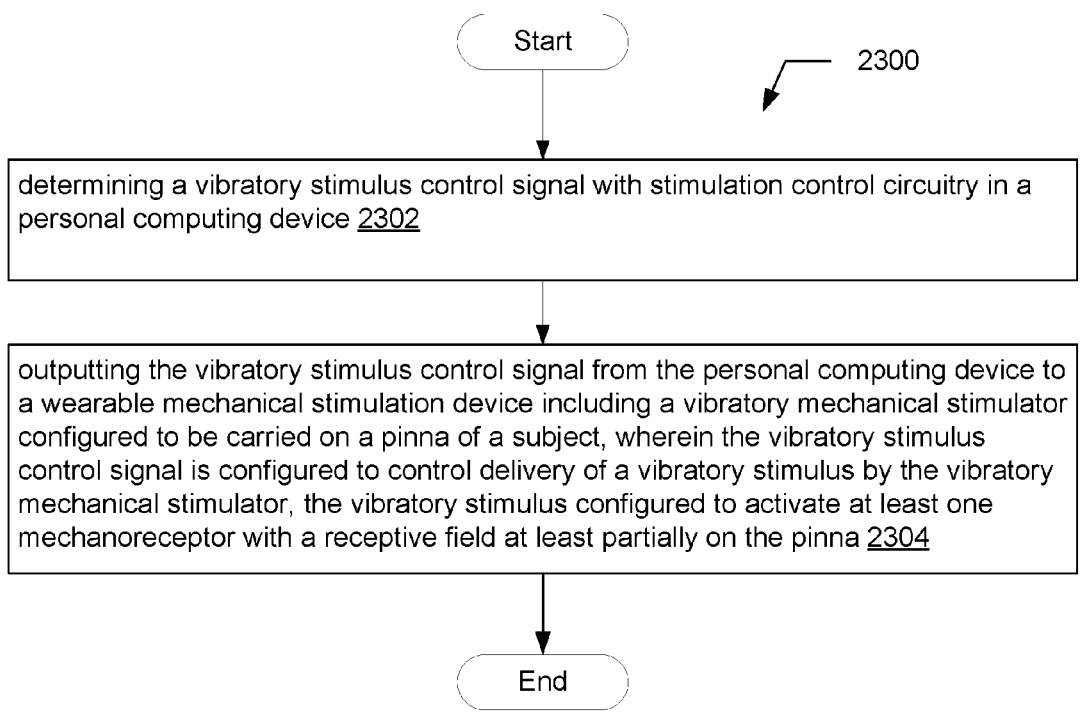
FIG. 23 is a flow diagram of a method.

FIG. 23 is a flow diagram of a method 2300 involving the use of a system as depicted in FIG. 22. In an aspect, method 2300 includes determining a vibratory stimulus control signal with stimulation control circuitry in a personal computing device, as indicated at 2302; and outputting the vibratory stimulus control signal from the personal computing device to a wearable mechanical stimulation device including a vibratory mechanical stimulator configured to be carried on a pinna of a subject, wherein the vibratory stimulus control signal is configured to control delivery of a vibratory stimulus by the vibratory mechanical stimulator, the vibratory stimulus configured to activate at least one mechanoreceptor with a receptive field on at least a portion of the pinna, as indicated at 2304.

Figure 24:
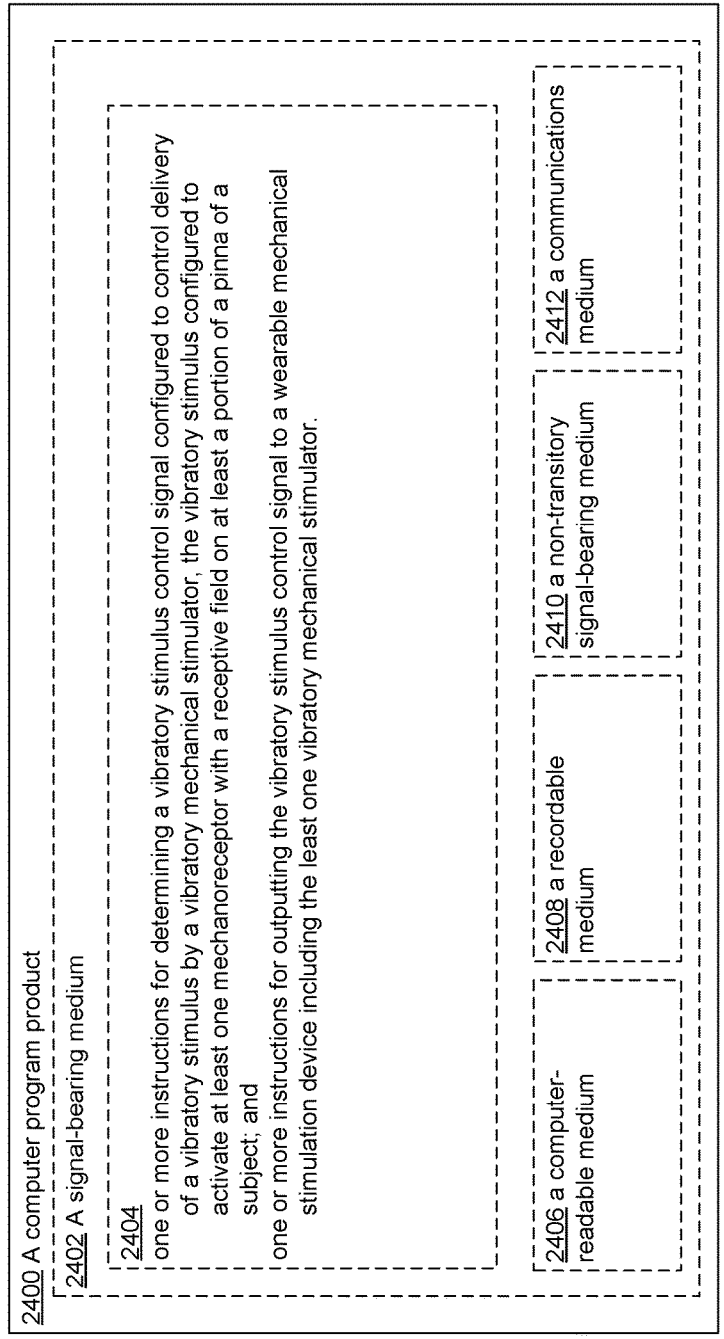
FIG. 24 is a block diagram of a computer program product relating to the method of FIG. 23.

FIG. 24 is a block diagram of a computer program product 2400 for implementing a method as described in connection with FIG. 23. Computer program product 2400 includes a signal-bearing medium 2402 bearing one or more instructions for determining a vibratory stimulus control signal configured to control delivery of a vibratory stimulus by a vibratory mechanical stimulator, the vibratory stimulus configured to activate at least one mechanoreceptor with a receptive field on at least a portion of a pinna of a subject, and one or more instructions for outputting the vibratory stimulus control signal to a wearable mechanical stimulation device including the least one vibratory mechanical stimulator, as indicated at 2404. Signal-bearing medium 2402 may be, for example, a computer-readable medium 2406, a recordable medium 2408, a non-transitory signal-bearing medium 2410, or a communications medium 2412, examples of which are described herein above.

Figure 25:
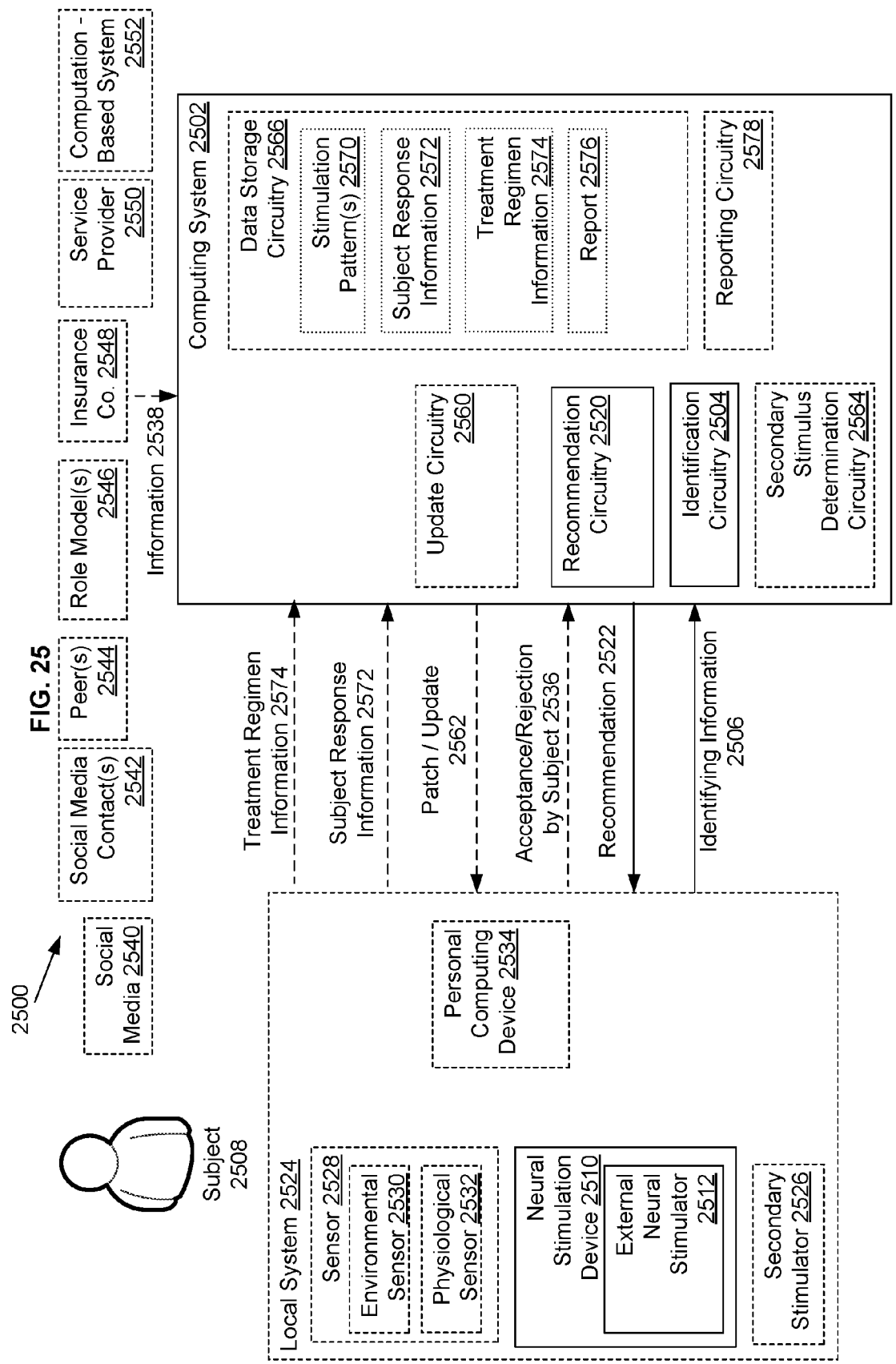
FIG. 25 is a block diagram of a system relating to operation of a neural stimulation device.

In some aspects, wearable neural stimulation devices and systems as described herein above are used in combination with remote systems. For example, FIGS. 2A and 2B illustrate a neural stimulation system used in combination with remote system 26, via communication network 218. FIG. 12 depicts communication between wearable neural stimulation device 1202 and/or personal computing device 1204, which form neural stimulation system 1200, and remote system 1224. In addition, as shown in FIG. 13, information may be transmitted to personal computing device 1302 from a remote system, including, for example, recommendation 1372, patch/update 1374, or instruction 1384. FIG. 25 provides greater detail regarding such a remote system 2500. Remote system 2500 includes computing system 2502. Computing system 2502 includes identification circuitry 2504 for receiving identifying information 2506 identifying at least one of a subject 2508 and a neural stimulation device 2510 associated with subject 2508. Neural stimulation device 2510 is a neural stimulation device configured to be carried on an ear of a subject and including an external neural stimulator 2512. System 2502 includes recommendation circuitry 2520 for providing a recommendation 2522 relating to a treatment regimen to subject 2508, where the treatment regimen includes delivery of a neural stimulus to the subject with external neural stimulator 2512, the neural stimulus configured to activate at least one sensory nerve fiber innervating skin on or in the vicinity of the ear of the subject. In an aspect, recommendation circuitry 2520 uses a database to generate recommendations for combinations of treatments in the treatment regimen, for example in a manner similar to that described in U.S. Pat. No. 7,801,686 granted Sep. 21, 2010 to Hyde et al.; U.S. Pat. No. 7,974,787 granted Jul. 5, 2011 to Hyde et al.; U.S. Pat. No. 8,876,688 granted Nov. 4, 2014 to Hyde et al.; U.S. Patent Publication 2009/0269329 to Hyde et al., dated Oct. 29, 2009; U.S. Patent Publication 2009/0271009 to Hyde et al. dated Oct. 29, 2009; and U.S. Patent Publication 2009/0271375 to Hyde et al. dated Oct. 29, 2009, each of which is incorporated herein by reference.

In various aspects, neural stimulation device 2510 is a neural stimulation device of any of the various types described herein, e.g., in connection with any of FIG. 7, 10, or 12. In an aspect recommendation 2522 is sent to, and identifying information 2506 is received from, a local system 2524. Local system 2524 includes neural stimulation device 2510 and other components at the location of subject 2508, including but not limited to a secondary stimulator 2526, at least one sensor 2528 (e.g., an environmental sensor 2530, a physiological sensor 2532, or other sensor as discussed herein above). In an aspect, local system 2524 includes personal computing device 2534. Personal computing device 2534 may include, for example, at least one of a personal digital assistant, a personal entertainment device, a mobile phone, a laptop computer, a tablet personal computer, a wearable computing device, a networked computer, a workstation computer, and a desktop computer, as discussed herein above. In an aspect, recommendation 2522 is presented to subject 2508 via a user interface of personal computing device 2534, for example, and acceptance or rejection of the recommendation entered via a user interface of personal computing device 2534 and transmitted as acceptance/rejection signal 2536 to remote computing system 2502.

Secondary stimulator 2526, sensor 2528, and personal computing device 2534 are as described herein above, e.g., in connection with at least FIGS. 7 and 12. Signals containing information, instructions, data, etc. may be sent between neural stimulation device 2510 and computing system 2502 directly, or information may be sent between computing system 2502 and personal computing device 2534, and then between personal computing device 2534 and neural stimulation device 2510. Transmission of signals (information, instructions, data, etc.) between computing system 2502 and local system 2524 may be via wired or wireless communication links, e.g., via computer or communication networks. In an aspect, computing system 2502 is part of a computing network from which it receives information 2536 from various parties and/or entities, including but not limited to social media 2540, social media contacts 2542, peers 2544, or role models 2546 of subject 2508, insurance companies, service providers (e.g., medical care providers or companies providing various health or wellness related services), and computation-based system associated with such service providers, for example.

Computing system 2502 includes one or more computing device, as described generally in connection with FIG. 8. In an aspect, computing system 2502 includes update generation circuitry 2560 for generating patch/update 2562 which is sent to local system 2524, for updating software on either personal computing device 2534 or neural stimulation device 2510. In an aspect, computing system 2504 includes secondary stimulus determination circuitry 2564 for determining a secondary stimulus to be delivered in combination with the neural stimulus, e.g., by secondary stimulator 2526. The secondary stimulus may be any of various types of stimuli, as described herein above. In an aspect, computing system 2502 includes data storage circuitry 2566, which in various aspects stores information regarding, e.g., one or more stimulation patterns 2570, subject response information 2572 received, e.g., from local system 2524, treatment regimen information 2574, or one or more report 2576. In an aspect, report 2576 is generated by reporting circuitry 2578 and stored in data storage circuitry 2566 in addition to, or as an alternative to, providing report 2576 to a recipient.

Figure 26:
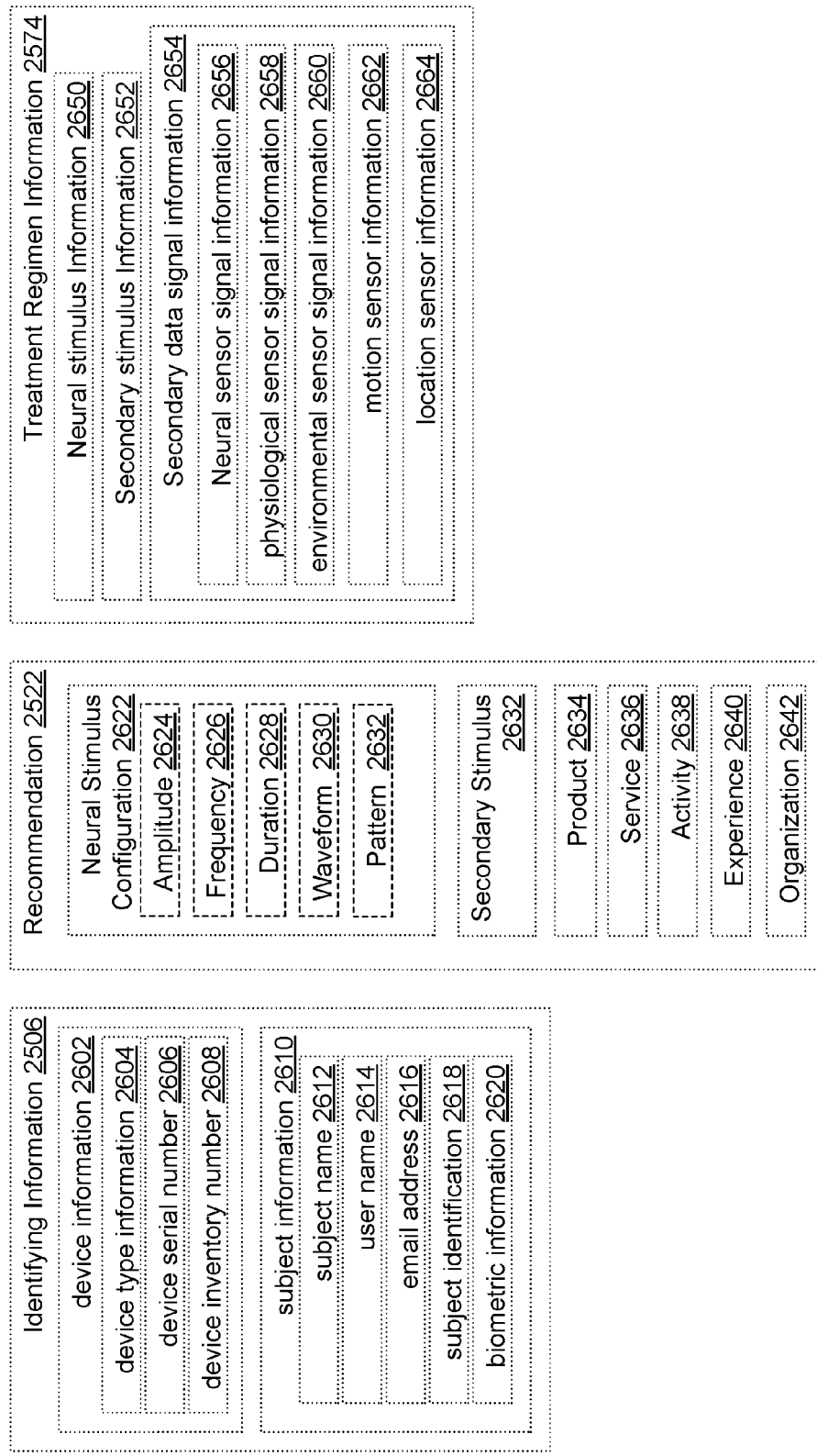
FIG. 26 depicts data aspects relating to FIG. 25.

FIG. 26 provides greater detail regarding several aspects of FIG. 25 of information handled by system 2500, specifically information included in identifying information 2506, recommendation 2522, and treatment regimen information 2574.

In various aspects, identifying information 2506 includes device information 2602 pertaining to the neural stimulation device 2510, or subject information 2610 pertaining to the subject. Device information 2602 includes, for example, device type information 2604, device serial number 2606, or device inventory number 2608). Subject information 2610 includes, for example, a name of the subject 2612, a user name 2614 associated with the subject, an email address 2616 associated with the subject, a subject identification 2618 (e.g., identification number, code or the like), or biometric information 2620 associated with the subject. In various aspects, subject identification 2618 can be input by the subject via a user input, read with a bar-code or RFID reader, received with an RF receiver, etc.

Recommendation 2522 may include one or more recommendations for various aspects of device and system configuration for delivery of neural stimulation, and for one or more additional stimuli or experiences to be presented to or experienced by the subject in association with the neural stimulus. In various aspects, recommendation 2522 is for a configuration of the neural stimulus 2622 (e.g., stimulus amplitude 2624, frequency 2626, duration 2628, waveform 2630, or delivery pattern 2632). In various aspects, recommendation 2522 is for a secondary stimulus 2632 to be delivered in association with the neural stimulus. In various aspects, secondary stimulus 2632 includes music, an auditory stimulus, a video stimulus, a tactile stimulus, a haptic stimulus, an olfactory stimulus, a pharmaceutical, a nutraceutical, a secondary neural stimulus, an experience (including, but not limited to a virtual reality experience, a game experience, a virtual therapist experience, an augmented reality experience, and/or an interactive experience). In various aspects, recommendation 2522 is for a product 2634, a service 2636, an activity 2638, an experience 2640, or an organization 2642. The recommendation may be for multiple experiences. In an aspect, the recommendation specifies a pattern of delivery of the experience(s). It will be appreciated that not all secondary stimuli recommended for use in conjunction with a neural stimulus are delivered by the neural stimulation system. Recommendations (e.g., for a product, service, experience, or organization) can be presented to the subject via the personal computing device in the form of a link to a relevant website, so that the subject may conveniently access the recommended product, service, experience, or organization, which the subject does, as desired.

Treatment regimen information 2574 includes, for example, neural stimulus information 2650 regarding the neural stimulus, secondary stimulus information 2652 regarding a secondary stimulus delivered in association with the neural stimulus, information 2654 regarding a secondary data signal, which may specifically include neural sensor signal information 2656, physiological sensor signal information 2658, environmental sensor signal information 2660, motion sensor information 2662 or location sensor information 2664.

Figure 27:
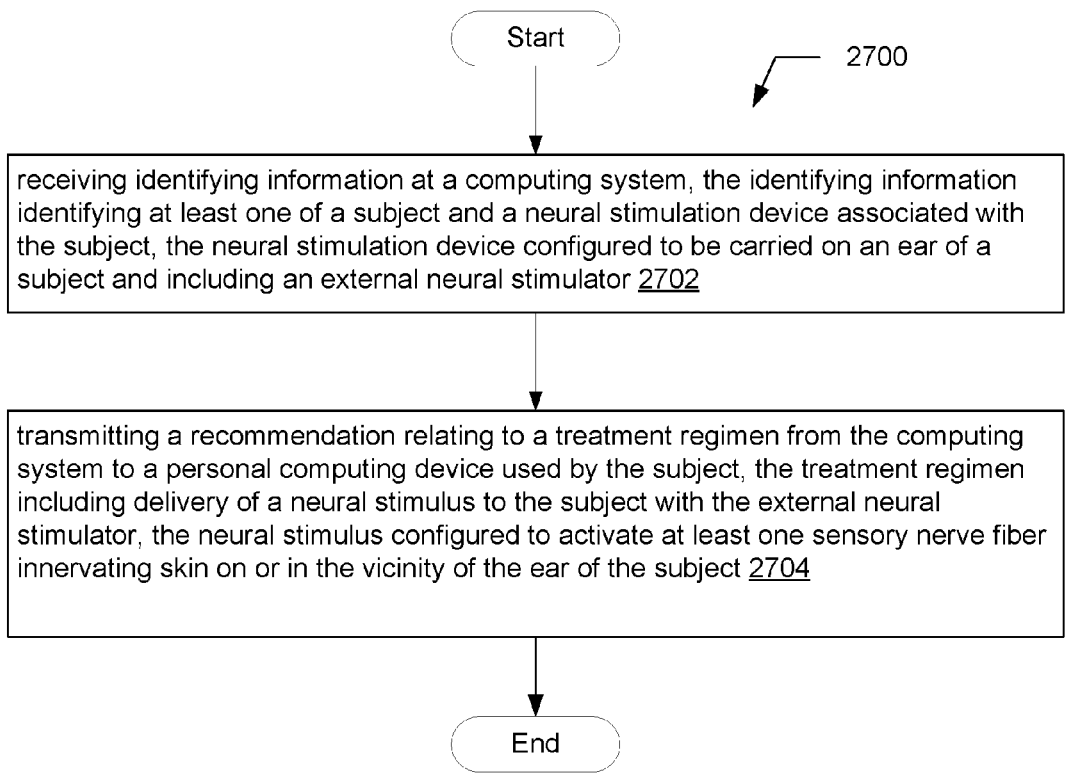
FIG. 27 is a flow diagram of a method.

FIG. 27 is a flow diagram of a method 2700 carried out in connection with a system as depicted in FIG. 25 for providing recommendations to a subject. In an aspect, a method 2700 includes receiving identifying information at a computing system (e.g., computing system 2502 in FIG. 25), the identifying information identifying at least one of a subject and a neural stimulation device associated with the subject, the neural stimulation device configured to be carried on an ear of a subject and including an external neural stimulator, as indicated at 2702; and transmitting a recommendation relating to a treatment regimen from the computing system to a personal computing device used by the subject (e.g., personal computing device, the treatment regimen including delivery of a neural stimulus to the subject with the external neural stimulator, the neural stimulus configured to activate at least one sensory nerve fiber innervating skin on or in the vicinity of the ear of the subject, as indicated at 2704.

In an aspect, receiving the identifying information at the computing system includes receiving information transmitted from the personal computing device. In an aspect, receiving the identifying information at the computing system includes receiving information transmitted via a computing network. In an aspect, receiving the identifying information at the computing system includes receiving information transmitted via a wireless network. In an aspect, providing the recommendation relating to the treatment regimen to the subject includes transmitting the recommendation to a personal computing device, e.g., via a computing network or a wireless network.

In an aspect, the recommendation is received at the computing system from a medical care provider. In another aspect, the recommendation is generated at the computing system, e.g., by recommendation circuitry 2520 as shown in FIG. 25. The recommendation can be generated based on various types of information: for example, information regarding a response of the subject to a past treatment regimen (subject response information 2572 in FIG. 25); information obtained via social media (e.g., information 2536 in FIG. 25) which may include, for example, information regarding one or more preferences of one or more social media contacts, peers, or role models of the subject); information from an insurance company; or information from a service provider. In an aspect, generating the recommendation includes generating the recommendation with a computation-based system 2552 (e.g., an artificial intelligence, machine learning system, or search engine based on a data-driven technique). In an aspect, generating the recommendation includes generating the recommendation based on a predicted response of the subject to a treatment regimen.

In an aspect, method 2700 includes receiving information regarding whether the subject has accepted or rejected the recommendation. In an aspect, method 2700 includes receiving a credential showing that the subject is an authorized user of the personal computing device. For example, the credential may include a password, a PIN, a biometric feature, or a card authentication, and/or a credential showing that the personal computing device is an authorized device.

In an aspect, method 2700 includes storing at least one parameter of the neural stimulus in a data storage location associated with the computing system (e.g., with data storage circuitry 2566 of computing system 2502).

In aspect, the recommendation relates to at least one parameter of the neural stimulus, for example, an amplitude, frequency, waveform, or duration of delivery of the neural stimulus, or stimulation pattern for delivery of the neural stimulus. The stimulation pattern may be, for example, a preprogrammed pattern, a continuous pattern, an intermittent pattern, a time-varying pattern, and/or a pulsed pattern. In an aspect, the recommendation specifies a selection of one of multiple stimulation patterns.

In an aspect, receiving the identifying information at the computing system includes receiving information transmitted from the personal computing device.

In an aspect, method 2700 includes transmitting a report relating to the treatment regimen to at least one recipient. In an aspect, the at least one recipient includes, for example, the subject, a caregiver of the subject, at least one social media contact of the subject, at least one peer of the subject, at least one medical care provider, or at least one insurance provider. In an aspect, the recipient is a computing system, e.g. a computing system used for storing and/or processing healthcare information. In some cases the report is anonymized, e.g., to preserve the privacy of the subject. The report may include demographic information pertaining to the subject, but not personal identifying information pertaining to the subject, for example. In an aspect, transmitting the report includes transmitting the report to the personal computing device. The report may include, for example, a neural stimulus control signal, a determined compliance of the subject with the treatment regimen, a determined efficacy of the treatment regimen, one or more system settings for controlling delivery of the neural stimulus, data retrieved from a data storage location associated with the computing system, and/or information regarding a secondary stimulus delivered in association with the neural stimulus. Compliance of the subject and/or efficacy of the treatment regimen may be determined by questioning the subject directly, by questioning another party, such as a caregiver, or by making a determination from measured physiological parameters of the subject.

In an aspect, method 2700 includes receiving a report relating to the treatment regimen from the personal computing device. In an aspect, method 2700 includes storing information relating to the treatment regimen in a data storage location associated with the computing system, e.g., treatment regimen information 2574 as described in connection with FIGS. 15 and 26.

In an aspect, method 2700 includes receiving information at the computing system regarding a previously delivered treatment regimen. In addition, the method may include receiving information at the computing system regarding a response of subject to the previously delivered treatment regimen.

In an aspect, method 2700 includes sending a patch or update to a personal computing device from the computing system. The patch or update may be for software installed on the personal computing device, or for software installed on the external neural stimulator.

In an aspect, method 2700 includes generating an update for the configuration of the neural stimulus. This may be done based on a response of the subject to a previous treatment regimen, based on an environmental factor, or based on motion or location of the subject. In an aspect, the update is generated automatically e.g., when it is determined that an update is needed (based on a subject response or sensed environmental factor). In another aspect, the update is generated based upon acceptance of a recommendation for the update by the subject.

Figure 28:
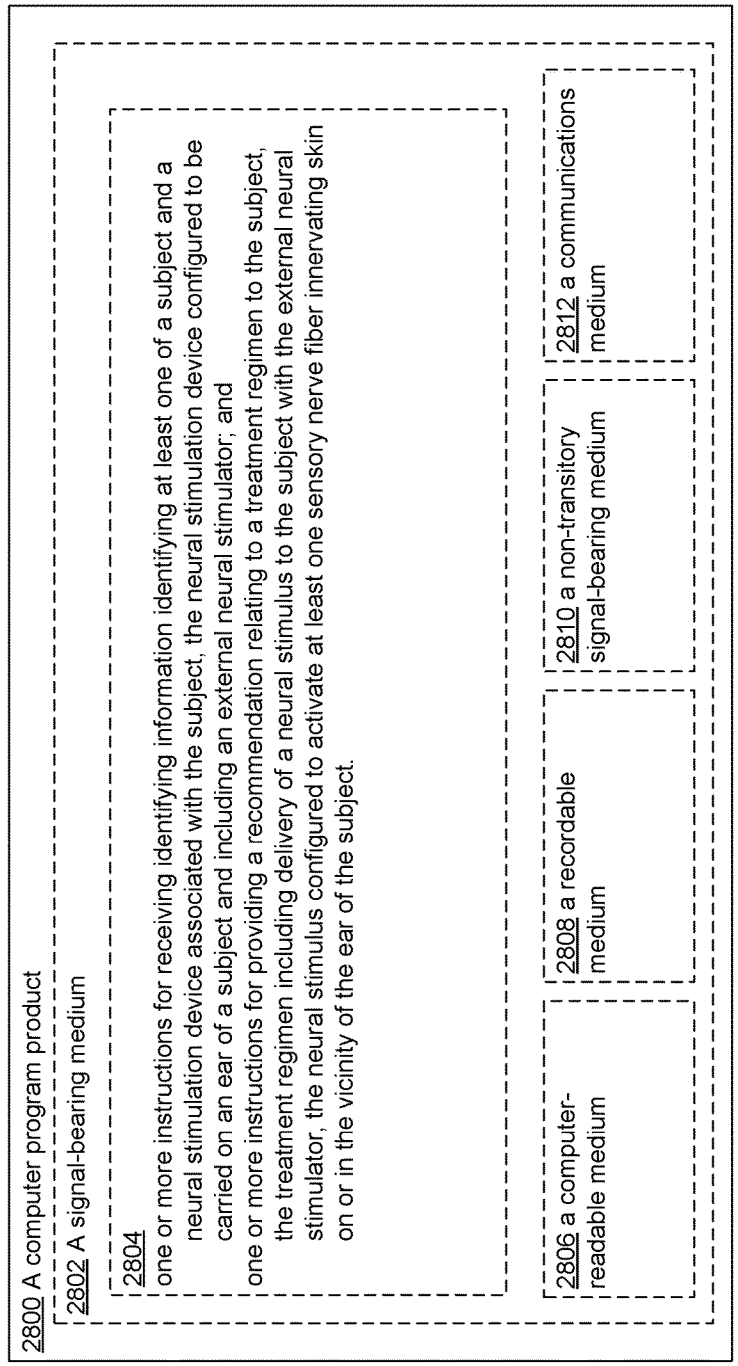
FIG. 28 is block diagram of a computer program product relating to the method of FIG. 27.

FIG. 28 is a block diagram of a computer program product 2800 for implementing a method as described in connection with FIG. 27. Computer program product 2800 includes a signal-bearing medium 2802 bearing one or more instructions for receiving identifying information identifying at least one of a subject and a neural stimulation device associated with the subject, the neural stimulation device configured to be carried on an ear of a subject and including an external neural stimulator, and one or more instructions for providing a recommendation relating to a treatment regimen to the subject, the treatment regimen including delivery of a neural stimulus to the subject with the external neural stimulator, the neural stimulus configured to activate at least one sensory nerve fiber innervating skin on or in the vicinity of the ear of the subject, as indicated at 2804. Signal-bearing medium 2802 may be, for example, a computer-readable medium 2806, a recordable medium 2808, a non-transitory signal-bearing medium 2810, or a communications medium 2812, examples of which are described herein above.

Figure 29:
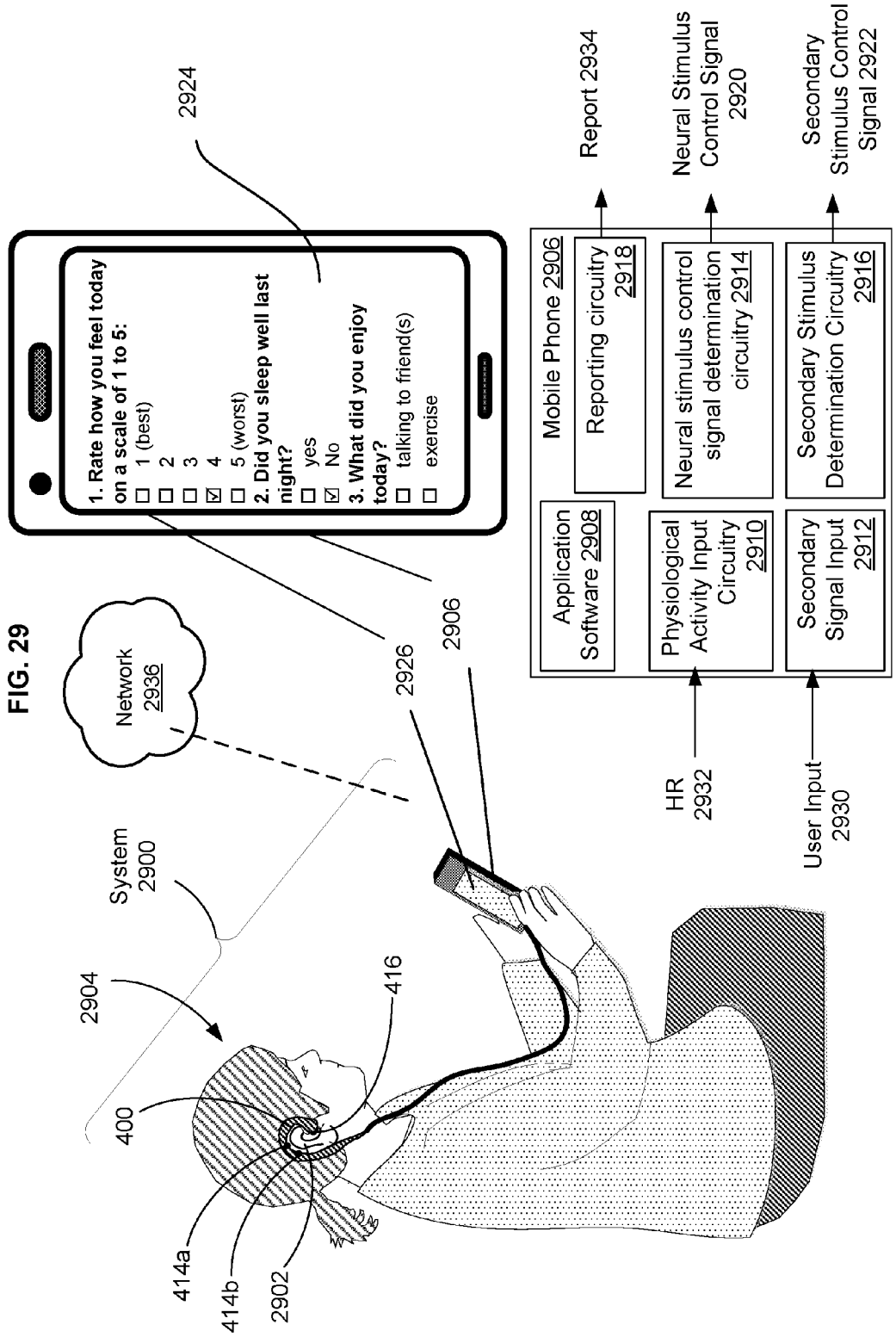
FIG. 29 is an illustration of an embodiment of a system for delivering neural stimulation in combination with a secondary stimulus.

FIG. 29 depicts an embodiment of a system 2900 for delivering neural stimulation in combination with providing a therapeutic secondary stimulus. System 2900 includes securing member 400, of the type depicted in FIGS. 4A and 4B, with an ear canal insert 416 including a heart rate sensor (not shown in FIG. 29), and stimulating electrodes 414a and 414b, positioned to stimulate pinna 2902 of subject 2904. System 2900 also includes mobile phone 2906, configured with application software 2908. Mobile phone 2906 and application software 2908 together form at least physiological activity input circuitry 2910, secondary signal input 2912, neural stimulus control signal determination circuitry 2914, secondary stimulus determination circuitry 2916, and reporting circuitry 2918. Mobile phone 2906 along with application software 2908 form a personal computing device, which includes a variety of circuitry (not all of which is depicted in FIG. 29), e.g. as depicted and described in connection with FIG. 16.

Neural stimulus control signal determination circuitry 2914 is used to generate neural stimulus control signal 2920, which drives delivery of a neural stimulus via electrodes 414a and 414b. Secondary stimulus determination circuitry 2916 is used to generate secondary stimulus control signal 2922, which controls delivery of the therapeutic secondary stimulus while subject 2904 is receiving stimulation delivered to pinna 2902. In the example of FIG. 29, the therapeutic secondary stimulus is provided via digital media, in the form of a therapy application that provides cognitive training and therapy. The therapy application also performs mental health monitoring. In an aspect, the therapy application includes an interactive survey 2924 displayed on touchscreen 2926 of mobile phone 2906. The survey asks subject 2904 questions designed, for example, to assess the subject's mental or emotional state ("Rate how you feel today"), identify factors contributing to or relating to the subject's mental or emotional state ("Did you sleep well last night?"), and guide the subject toward positive and/or constructive thought patterns ("What did you enjoy today?"). Subject 2904 provides responses (user input 2930) to the queries via touchscreen 2926, which are received by secondary signal input 2912. In addition, or as an alternative, the therapy application may provide a therapeutic secondary stimulus that includes music or guided meditation, delivered via touchscreen 2926 and/or a speaker in ear canal insert 416.

Heart rate 2932, sensed with a heart rate sensor (for example an ECG sensor or pulse oximeter sensor) in ear canal insert 416, is provided to physiological activity input circuitry 2910. The subject's heart rate is monitored during delivery of neural stimulation in combination with the therapeutic secondary stimulus, to track the effect of the stimulation and therapy over time. Amount of heart rate variability and duration of heart variability and/or changes in heart rate variability over time may be monitored. Heart rate variability is an indicator of the balance between sympathetic and parasympathetic tone. Increased heart rate variability is associated with reduced inflammation and anxiety. In addition, the physiologic data can be coupled with how the subject interacts with the program. In an aspect, one or both of neural stimulus control signal 2920 and secondary stimulus control signal 2922 are modified (by neural stimulus control signal determination circuitry 2914 and secondary stimulus determination circuitry 2916, respectively), in response to heart rate 2932 and user input 2930. Physiological data regarding the subject's heart rate as well as data regarding interaction of subject 2904 with application software 2908 can be included in report 2934 which can be sent to the subject's medical care provider or psychologist via network 2936. Detection of a heart rate indicative of an unsafe condition due to the neural stimulation results in discontinuation or modulation of stimulation, and transmittal of a notification to the subject's medical care provider.

Figure 30:
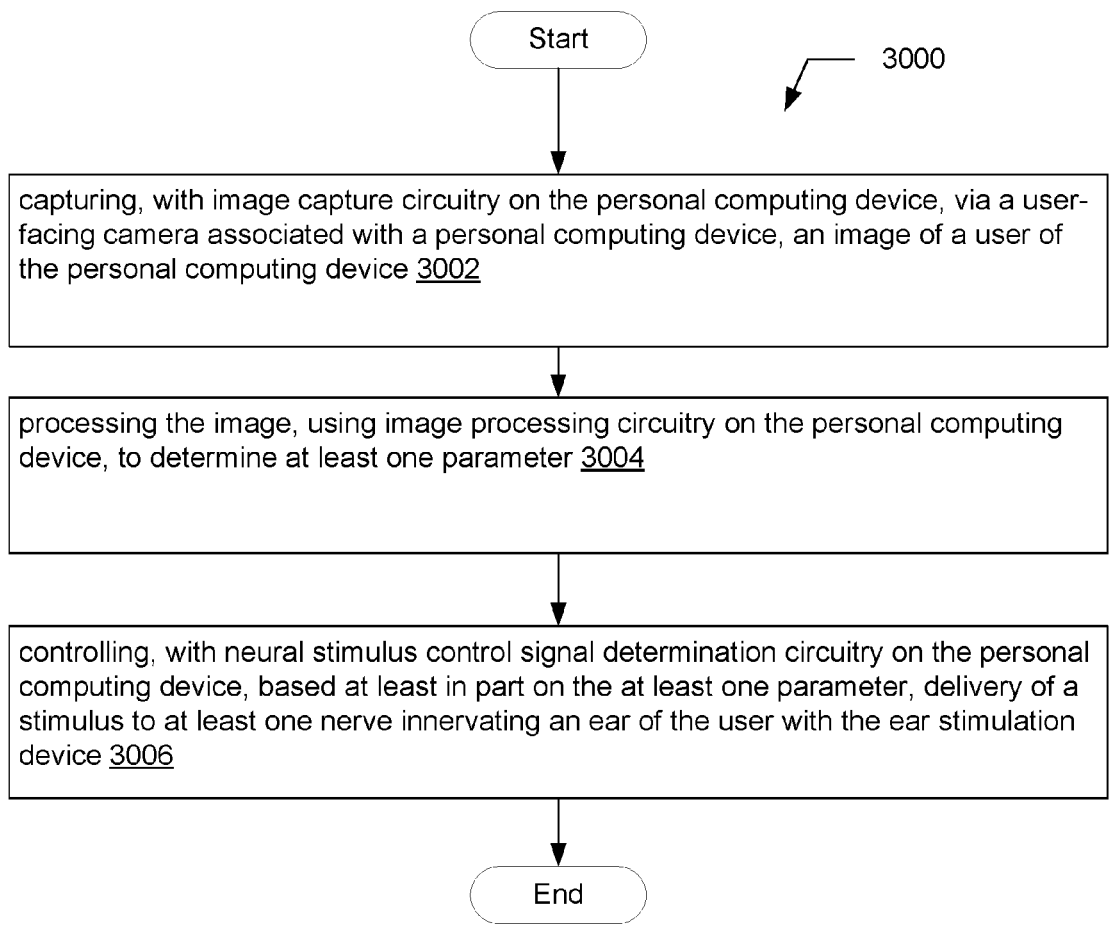
FIG. 30 is a flow diagram of a method.

FIG. 30 is a flow diagram of a method of controlling an ear stimulation device with a personal computing device. The ear stimulation device is a wearable neural stimulation device as described elsewhere herein (e.g. wearable ear stimulation device 202 controlled with personal computing device 208, as depicted in FIGS. 2A and 2B), for delivering a stimulus to an ear of a user of the personal computing device to stimulate at least one nerve innervating the ear. In an aspect, the ear stimulation device includes an earpiece that incorporates a positioning element and a neural stimulator, various examples of which are described and depicted herein. In an aspect, the ear stimulation device is part of a system that is used for delivering sound (e.g., music), and the earpiece includes a speaker or other sound source. In an aspect, the system includes a pair of earpieces. In an aspect, only one of the earpieces includes a neural stimulator, but both earpieces include a speaker or other sound source. In another aspect, both earpieces include both neural stimulator and sound source. In another aspect, one earpiece includes a sound source and the other includes a neural stimulator. In an aspect, method 3000 in FIG. 30 includes capturing, with image capture circuitry on the personal computing device, via a user-facing camera associated with a personal computing device, an image of a user of the personal computing device, as indicated at 3002; processing the image, using image processing circuitry on the personal computing device, to determine at least one parameter as indicated at 3004; and controlling, with neural stimulus control signal determination circuitry on the personal computing device, based at least in part on the at least one parameter, delivery of a stimulus to at least one nerve innervating an ear of the user with the ear stimulation device, as indicated at 3006.

Figure 31:
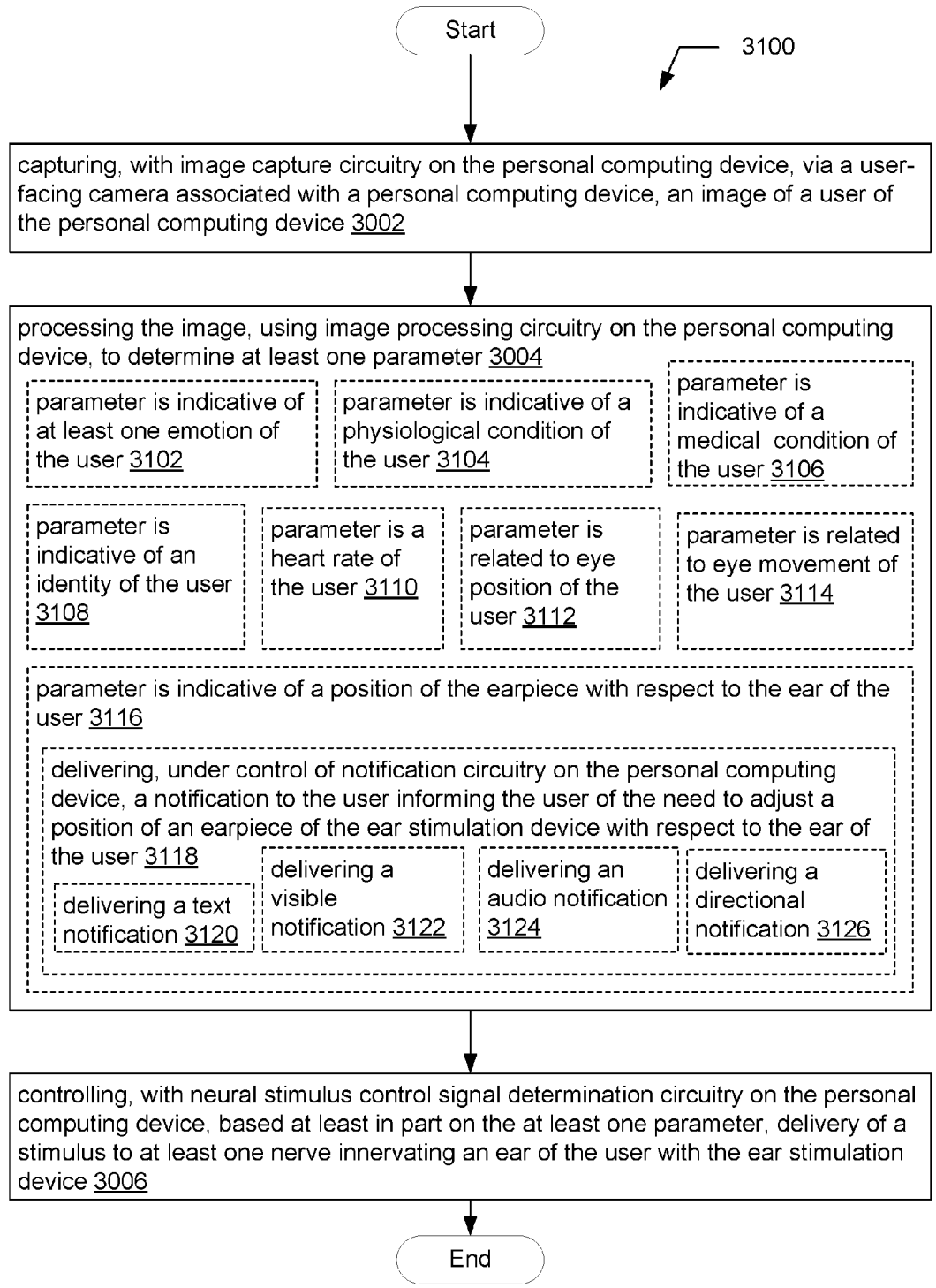
FIG. 31 is a flow diagram of a method.
Figure 32:
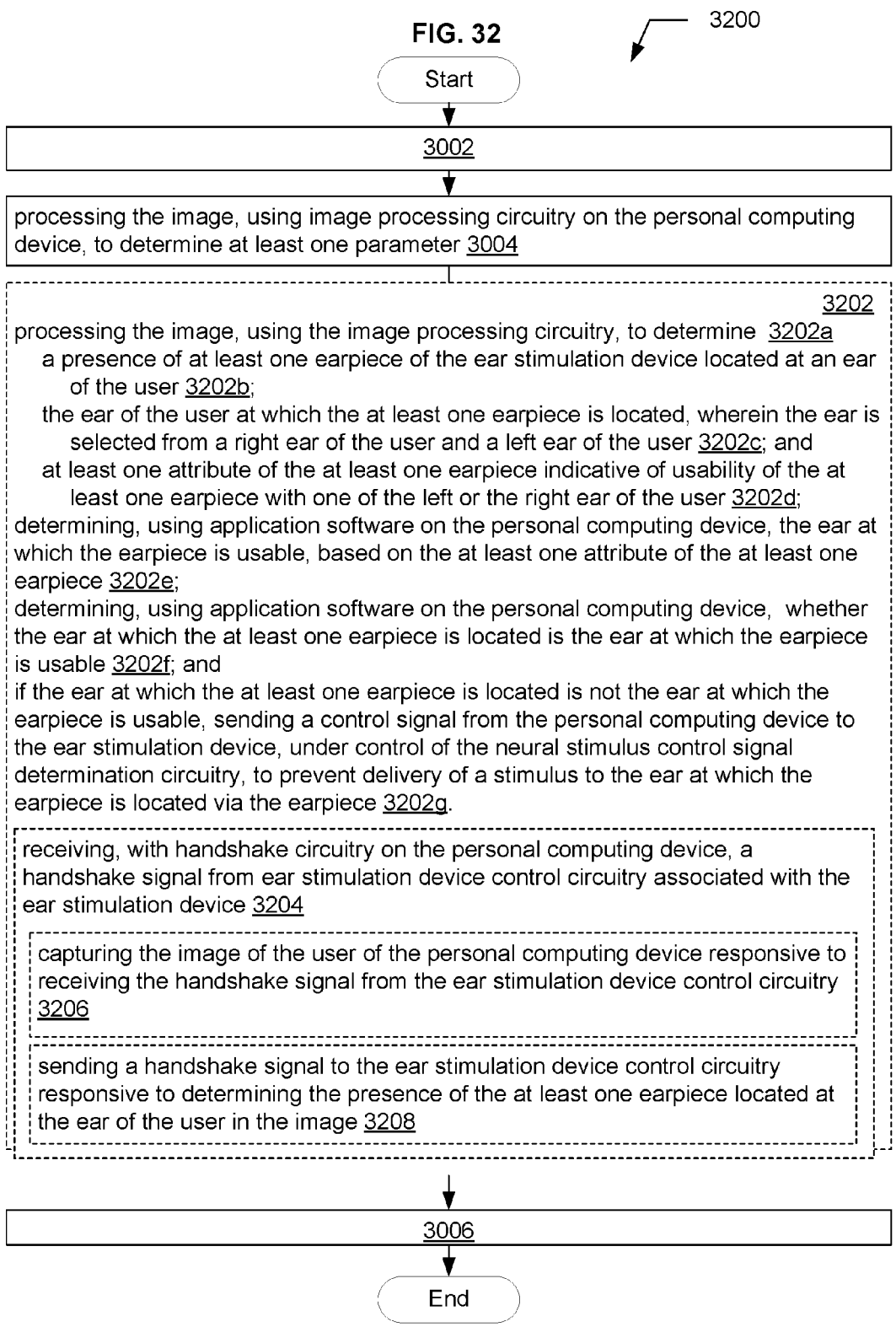
FIG. 32 is a flow diagram of a method.
Figure 33:
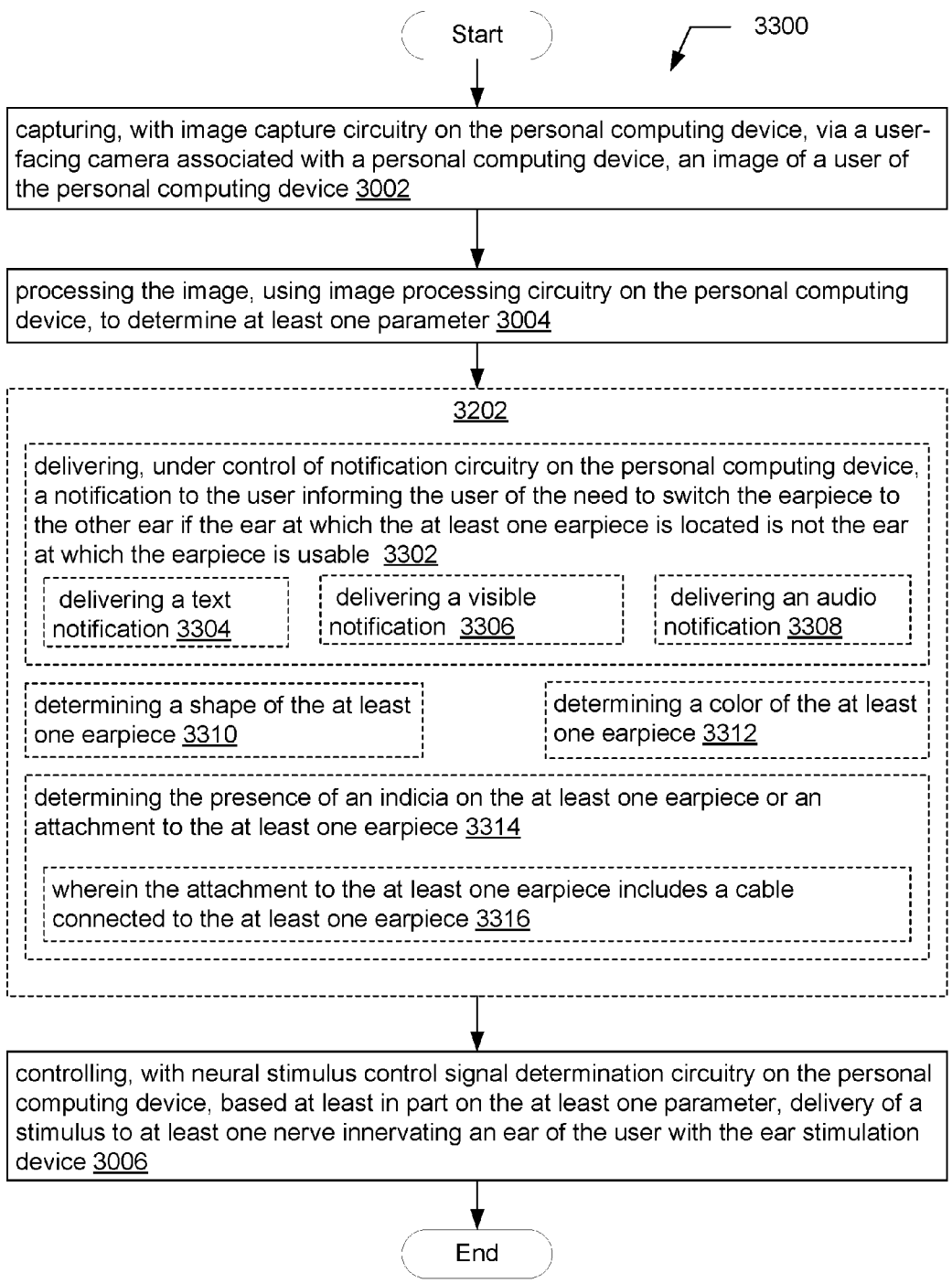
FIG. 33 is a flow diagram of a method.

FIGS. 31-33 depict further aspects of the method of FIG. 30, wherein steps 3002, 3004, and 3006 are as depicted and described in connection with FIG. 30. As depicted in FIG. 31, in further aspects of method 3100, the at least one parameter is indicative of at least one emotion of the user 3102, is indicative of a physiological condition of the user 3104, is indicative of a medical condition of the user 3106, is indicative of an identity of the user 3108, is a heart rate of the user 3110, is related to eye position of the user 3112, is related to eye movement of the user 3114 of the user, or is indicative of a position of the earpiece with respect to the ear of the user 3116. Various schemes for identifying or classifying emotions have been devised, and the meaning of the term, as used herein, is not tied to any specific scheme. Examples of emotions include, but are not limited to, e.g. depression, anxiety, agitation, happiness, sadness, excitement, fear, and anger. In various aspects, a physiological condition of the subject is indicative of a medical condition of the subject. Medical conditions of the subject, include, for example, muscle spasm, seizure, epilepsy (e.g., seizure, spasm, staring), drowsiness, lethargy, fatigue, pain, fever, hypertension (e.g., sweating, flushing), hypotension, or mental state.

Determining a parameter indicative of a position of the earpiece with respect to the ear of the user can include, for example, determining a distance of one or more portion of the earpiece with respect to various anatomical features of the ear, e.g., the ear canal, the tragus, the helix, the lobe, etc., to determine whether the earpiece is positioned on the appropriate portion of the pinna or inserted far enough into the ear canal, for example. In an aspect, method 3100 further includes delivering, under control of notification circuitry on the personal computing device, a notification to the user informing the user of the need to adjust a position of an earpiece of the ear stimulation device with respect to the ear of the user, as indicated at 3118. In various aspects, delivering a notification includes delivering a text notification 3120, delivering a visible notification 3122, or delivering an audio notification 3124. The notification can be specific (e.g., a text or audio notification instructing the user to "push the earpiece further into the ear canal" or "move the earpiece higher up on the pinna") or non-specific (e.g., a flashing light or beeping sound that indicates the need to reposition the earpiece without providing detail on how specifically it should be repositioned). In an aspect, delivering a notification includes delivering a directional notification 3126. As used herein, the term "directional notification" refers a notification that provides information to the user regarding the direction of movement needed to move the earpiece to the proper position. For example, in an aspect, the notification includes a text or audio notification as described above, which instructs the user to "push the earpiece further into the ear canal" or "move the earpiece higher up on the pinna." In another aspect, the notification includes a tone that changes in pitch as the earpiece moves toward or away from the proper location, or a click or other pulsed sound that is repeated at a frequency that changes as the earpiece moves toward or away from the proper location. In an aspect, the tone can change (i.e. changing to another tone, or stopping entirely) when the earpiece is in the proper location.

The vagus innervation of the ears is not strictly symmetrical; for example, the right ear, unlike the left ear, is innervated by a branch of the vagus nerve that, when stimulated, influences heart rate. Accordingly, in some circumstances it may be preferred to stimulate the left, but not the right ear, to avoid affecting the heart rate of the user. Therefore, if the system includes two earpieces (e.g., for the purpose of delivering music or other audio to both the left and right ear), in an aspect, only one of the earpieces includes a neural stimulator. For example, the earpiece with the neural stimulator is then considered to be usable on the left ear, but not the right ear. In some aspects, the two earpieces are shaped differently such that one fits the left, but not the right ear and the other fits the right, but not the left ear. In other aspects, the two earpieces are shaped such that they fit on either ear. In such a situation, the two earpieces may be distinguished from each other based on shape or color, or by inclusion of indicia on the earpiece or associated cable, and the ear stimulation device control system. A method 3200 as outlined in FIG. 32, which is a further variant of the method of FIG. 30, can be used in connection with the ear stimulation device to ensure that the earpiece with the neural stimulator is used only with the ear with which it is considered to be usable. Method 3200, includes at 3202 the following steps: processing the image, using the image processing circuitry, to determine (at 3202a) the presence of at least one earpiece of the ear stimulation device located at an ear of the user, as indicated at 3202b; the ear of the user at which the at least one earpiece is located, wherein the ear is selected from a right ear of the user and a left ear of the user, as indicated at 3202c, and at least one attribute of the at least one earpiece indicative of usability of the at least one earpiece with one of the left or the right ear of the user, as indicated at 3202d; determining, using application software on the personal computing device, the ear at which the earpiece is usable, based on the at least one attribute of the at least one earpiece 3202e; determining, using application software on the personal computing device, whether the ear at which the at least one earpiece is located is the ear at which the earpiece is usable 3202f; and, if the ear at which the at least one earpiece is located is not the ear at which the earpiece is usable, sending a control signal from the personal computing device to the ear stimulation device, under control of the neural stimulus control signal determination circuitry, to prevent delivery of a stimulus to the ear at which the earpiece is located via the earpiece, as indicated at 3202g. In a further aspect, method 3200 includes receiving, with handshake circuitry on the personal computing device, a handshake signal from ear stimulation device control circuitry associated with the ear stimulation device, as indicated at 3204. This may include capturing the image of the user of the personal computing device responsive to receiving the handshake signal from the ear stimulation device control circuitry, as indicated at 3206. In an aspect, method 3200 includes sending a handshake signal to the ear stimulation device control circuitry responsive to determining the presence of the at least one earpiece located at the ear of the user in the image, as indicated at 3208.

FIG. 33 depicts method 3300, providing further detail regarding the method of FIG. 32, with step 3202 in FIG. 33 the same as in FIG. 32. In an aspect, method 3300 includes delivering, under control of notification circuitry on the personal computing device, a notification to the user informing the user of the need to switch the earpiece to the other ear if the ear at which the at least one earpiece is located is not the ear at which the earpiece is usable, as indicated at 3302. Delivering the notification to the user may include, for example, one or more of delivering a text notification, at 3304, delivering a visible notification, at 3306, or delivering an audio notification, at 3308. In various aspects, determining the at least one attribute 3433 of the at least one earpiece includes determining a shape of the at least one earpiece, at 3310, or determining a color of the at least one earpiece, at 3312, for example. In an aspect, determining the at least one attribute 3433 of the at least one earpiece includes determining the presence of an indicia on the at least one earpiece or an attachment to the at least one earpiece, as indicated at 3314. In an aspect, the attachment to the at least one earpiece includes a cable connected to the at least one earpiece, as indicated at 3316.

An alternative approach to addressing the usability of neural stimulation with the right ear versus the left ear is to include stimulation electrodes in both earpieces, but send a neural stimulus control signal to cause delivery of a neural stimulus only via one of the earpieces (e.g., the left ear). In an aspect, a neural stimulus control signal is sent to only one of the earpieces. In an aspect, this is done if separate neural stimulus control signal outputs are provided for the two earpieces. In another aspect, a neural stimulus control signal is sent to both earpieces, but causes delivery of stimulus via only one of the earpieces. This can be done, e.g., by including ear stimulation electrical circuitry in the two earpieces that produces a neural stimulus in response to different neural stimulus control signals. For example, the neural stimulus control signal can have one or more characteristics (e.g., frequency, polarity, activation code) that cause activation of ear stimulation device control circuitry in one but not the other of the two earpieces. It is assumed that it is known a priori that a particular earpiece (as identified by the attribute determined in the user image) will receive and be activated by the neural stimulus control signal.

Figure 34:
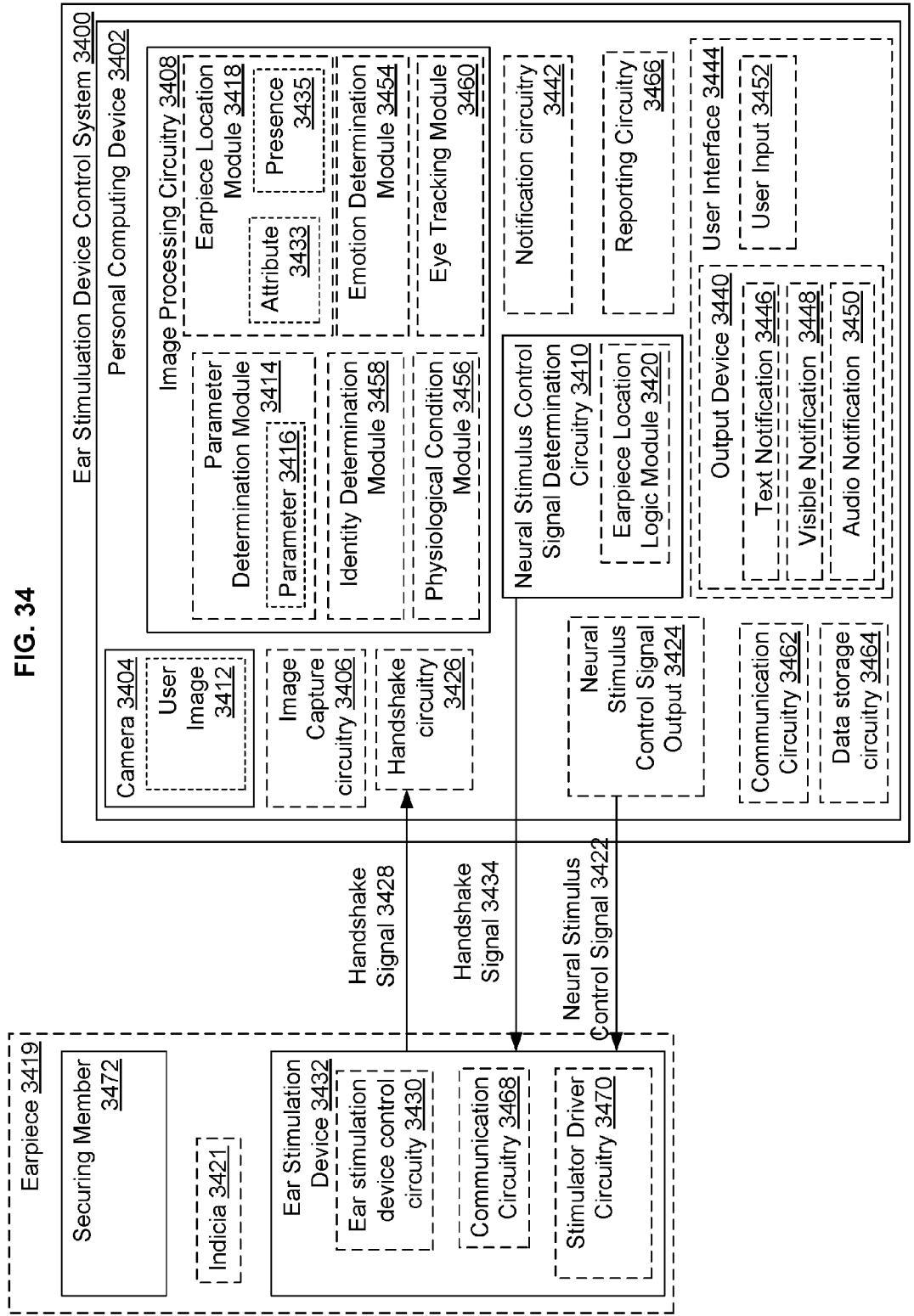
FIG. 34 is a block diagram of a neural stimulation system.

FIG. 34 is a block diagram of an ear stimulation device control system 3400. System 3400 includes a personal computing device 3402; a user-facing camera 3404 associated with the personal computing device, image capture circuitry 3406, image processing circuitry 3408, and neural stimulus control signal determination circuitry 3410. In various aspects, personal computing device 3402 is a phone, watch, wearable device, tablet computer, laptop computer, or desktop computer, for example.

Image capture circuitry 3406 is adapted to capture an image 3412 of a user of personal computing device 3402 from user-facing camera 3404. In an aspect, user-facing camera is built into the personal computing device. In another aspect, user-facing camera 3404 is connected to personal computing device via either a wired or wireless connection. Image processing circuitry 3408 is configured to process image 3412, using parameter determination module 3414, to determine at least one parameter 3416. Neural stimulus control signal determination circuitry 3410 is configured to control delivery of a stimulus to at least one nerve innervating an ear of the user with an ear stimulation device 3432, based at least in part on the at least one parameter 3416. In various aspects, parameter 3416 is indicative of one or more of at least one emotion of the user, a physiological condition of the user, an identity of the user, or a heart rate of the user. In an aspect, parameter 3416 is related to an eye position or eye movement of the user. In an aspect, parameter 3416 is indicative of a position of the earpiece with respect to the ear of the user In an aspect, image processing circuitry 3408 includes earpiece location module 3418, which is configured to process image 3412 to determine the presence 3435 of at least one earpiece 3419 of the ear stimulation device 3432 located at an ear of the user; the ear of the user at which the at least one earpiece is located, the ear selected from a right ear of the user and a left ear of the user; and at least one attribute 3433 of the at least one earpiece indicative of usability of the at least one earpiece 3419 with one of the left or the right ear of the user, as discussed herein above. Attribute 3433 may be, for example, an indicia 3421 used to indicate that the earpiece in question includes a neural stimulator, for example. In an aspect, neural stimulus control signal determination circuitry 3410 is configured (with earpiece location logic module 3420) to determine the ear at which the earpiece is usable, based on the at least one attribute 3433 of the at least one earpiece; determine whether the ear at which the at least one earpiece is located is the ear at which the earpiece is usable; and if the ear at which the at least one earpiece is located is not the ear at which the earpiece is usable, send a control signal from the personal computing device to the ear stimulation device (neural stimulus control signal 3422 from neural stimulus control signal output 3424) to prevent delivery of the stimulus to the a least one nerve innervating the ear of the user. As discussed herein above, in some circumstances it may be preferred to stimulate the left, but not the right ear, for example. Hence, in a system that includes two earpieces, the two earpieces may be distinguished from each other based on shape or color, or by inclusion of indicia on the earpiece or associated cable. In various aspects, indicia include any sort of markings detectable in the image via image processing. Indicia may include solid colored or patterned markings on an earpiece, or may include a characteristic of the earpiece itself (e.g., the color of the material of which the earpiece is made). Indicia may be detectable in the visible spectrum, or at other wavelengths. In some aspects, indicia may include text, alphanumeric markings, or symbols. The right and left ears of the user may be identified in user image 3412, using image processing methods, e.g. as described in M. M. Fakhir et al., "Face Recognition Based on Features Measurement Technique," 2014 UKSim-AMSS 8th European Modelling Symposium, pp. 158-162; U.S. Patent Application Publication No. 2016/0026781 to Boczek et al.; and U.S. Patent Application Publication No. 2008/0285813 to Holm; each of which is incorporated herein by reference. In some aspects, the position of one or both ears with respect to the face is determined; in some aspects, the shape and/or features of one or both ears is determined.

In an aspect, ear stimulation device control system 3400 includes handshake circuitry 3426 adapted to receive a handshake signal 3428 from ear stimulation device control circuitry 3430 associated with the ear stimulation device 3432. In an aspect, image capture circuitry 3406 is adapted to capture the image 3412 of the user of the personal computing device 3402 responsive to receiving the handshake signal 3428 from the ear stimulation device control circuitry 3430. For example, in an aspect exchange of information between the ear stimulation device control system 3400 and ear stimulation device 3432 is initiated after user image 3412 has been captured and evaluated by image processing circuitry 3408, and it has been determined, by earpiece location logic module 3420, that the earpiece containing the ear stimulation device has been placed on the appropriate ear of the user. Alternatively, if two earpieces including ear stimulation devices are utilized, the handshake signal from each earpiece can include an earpiece identification code for identifying the earpiece. The earpiece identification code and indicia associated with a particular earpiece can be linked in a lookup table stored in data storage circuitry 3464, for example.

In an aspect, the neural stimulus control signal determination circuitry 3410 is configured to send a handshake signal 3434 to ear stimulation device control circuitry 3430 responsive to determining the presence 3435 of the at least one earpiece located at the ear of the user in the image.

In an aspect, ear stimulation device control system includes output device 3440, and notification circuitry 3442, which is adapted to provide a notification via output device 3440 instructing the user of to switch the earpiece to the other ear if the ear at which the at least one earpiece is located is not the ear at which the earpiece is usable. For example, output device 3440 may be part of user interface 3444. In an aspect, output device is adapted to deliver a text notification 3446 to the user (e.g., output device includes an LED or LCD display, 7-segment display, or other alphanumeric display). In another aspect, output device 3440 is adapted to deliver a visible notification 3448 to the user, which may include a text display, as described previously, a graphic or symbol presented on a display, or a light that can be illuminated, flashed, etc. to attract the attention of the user. In an aspect, output device 3440 is adapted to deliver an audio notification 3450 to the user (e.g., output device 3440 includes a speaker, bell, buzzer, or other audio source for delivering one or both of a verbal notification or an alarm tone). User interface 3444 may also include one or more user input 3452, of various types, e.g. as discussed elsewhere herein.

As noted above, image processing circuitry 3408 includes earpiece location module 3418, which is configured to process image 3412 to determine at least one attribute 3433 of the at least one earpiece, where in an aspect the at least one attribute 3433 is indicative of usability of the at least one earpiece with one of the left or the right ear of the user. In addition, neural stimulus control signal determination circuitry 3410 is configured (with earpiece location logic module 3420) to determine the ear at which the earpiece is usable, based on the at least one attribute of the at least one earpiece. In an aspect, the at least one attribute of the at least one earpiece includes a shape of the at least one earpiece, a color of the at least one earpiece, a presence of an indicia 3421 on the at least one earpiece or a presence of indicia 3421 on an attachment to the at least one earpiece, where, as noted above, the attachment to the at least one earpiece may be, for example, a cable connected to the at least one earpiece. For example, in a system in which only one of two earpieces includes a stimulating electrode, the cable connected to the earpiece with the electrode may include a pattern of light and dark stripes, while the cable connected to the other earpiece may be a solid color. In embodiments in which two earpieces including ear stimulation devices are used, neural stimulus control signal determination logic can send a neural stimulus control signal 3422 sufficient to activate only an earpiece that is usable with the ear upon which it is located, based on the output of earpiece location logic module 3420.

In an aspect, image processing circuitry 3408 includes emotion determination module 3454, which determines an emotion of the user from user image 3412, based upon one or more parameter 3416, e.g. from facial expression, for example using methods as described in Su, "A simple approach to facial expression recognition," Proceedings of the 2007 Int'l Conf on Computer Engineering and Applications, Queensland, Australia, 2007, pp. 456-461; U.S. Pat. No. 9,036,018 to Wang et al.; U.S. Pat. No. 8,488,023 to Bacivarov et al., and U.S. Patent Application Publication 2004/0207720 to Miyahara et al., each of which is incorporated herein by reference.

In an aspect, image processing circuitry 3408 includes physiological condition module 3456, which determines a physiological condition of the user from user image 3412, based upon one or more parameter 3416. Physiological condition of the user can be inferred from eye movement, pupil dilation, heart rate, respiration rate, facial coloration, facial temperature, etc. A visible or IR image of the patient, obtained with a camera built into a personal computing device or operatively connected to the personal computing device can be used. Still or moving (video) image may be used. For example, video images of the subject may be analyzed to determine blood flow using Eulerian video magnification. Further data analysis may be used to determine blood pressure in the subject. See, e.g., Wu et al., ACM Trans. Graph. 31, 4, Article 65, July 2012; (available online at http://doi.acm.org/10.1145/2185520.2185561), which is incorporated herein by reference. An infrared camera may be used to measure corneal temperature (see e.g., Kessel et al., Investigative Opthalmology and Visual Science 51: 6593-6597, 2010 which is incorporated herein by reference). An infrared camera with a focal plane array detector, thermal sensitivity ≤0.09 degrees C. and an accuracy of 0.1 degrees C. is available from Fluke Corp., Everett, Wash. (see e.g., Fluke Ti25 Datasheet which is incorporated herein by reference).

Peripheral sympathetic responses can be detected through image analysis, as described in IEEE TRANSACTIONS ON BIOMEDICAL ENGINEERING, VOL. 56, NO. 2, FEBRUARY 2009 477, Imaging Facial Signs of Neurophysiological Responses, Dvijesh Shastri, Associate Member, IEEE, Arcangelo Merla, Member, IEEE, Panagiotis Tsiamyrtzis, and Ioannis Pavlidis, Senior Member, IEEE, which is incorporated herein by reference. For example, thermal imaging measurements from several different regions of the face provide indication of blood flow, sweat gland activation, and breathing, providing information similar to galvanic skin response. In various aspects, physiological condition module 3456 is used to determine one or more medical condition, including, for example, muscle spasm, seizure, epilepsy (e.g., seizure, spasm, staring), drowsiness, lethargy, fatigue, pain, fever, hypertension (e.g., sweating, flushing), hypotension, mental state In an aspect, image processing circuitry 3408 includes identity determination module 3458, which determines an identity of the user from user image 3412, based upon one or more parameter 3416. For example, systems and algorithms to obtain iris images, identify unique signatures and rapidly compare key features of iris images to a large database of iris images are described (see e.g., U.S. Pat. No. 5,572,596 issued to Wildes et al. on Nov. 5, 1996 and U.S. Pat. No. 4,641,349 issued to Flom et al. on Feb. 3, 1987 which are incorporated herein by reference). An iris scanning system which includes a near-infrared (approximately 700-900 nm) illumination source, a 1.3 megapixel camera and algorithms to analyze and compare iris images is available from Bayometric Inc., San Jose, Calif. (see e.g., the Specification Sheet: "Crossmatch Retinal Scan 2 Iris Scanner" which is incorporated herein by reference). In another aspect, facial recognition circuitry is used to determine the presence of the user through facial recognition, e.g., using approaches as described in Wheeler, Frederick W.; Weiss, R. L.; and Tu, Peter H., "Face Recognition at a Distance System for Surveillance Applications," Fourth IEEE International Conference on Biometrics: Theory Applications and Systems (BTAS), 2010 Page(s): 1-8 (DOI: 10.1109/BTAS.2010.5634523), and Moi Hoon Yap; Ugail, H.; Zwiggelaar, R.; Rajoub, B.; Doherty, V.; Appleyard, S.; and Hurdy, G., "A Short Review of Methods for Face Detection and Multifractal Analysis," International Conference on CyberWorlds, 2009. CW '09, Page(s): 231-236 (DOI: 10.1109/CW.2009.47), both of which are incorporated herein by reference. Biometric identification can also include recognition based on a variety of physiological or behavioral characteristics, such as fingerprints, voice, iris, retina, hand geometry, handwriting, keystroke pattern, etc., e.g., as described in Kataria, A. N.; Adhyaru, D. M.; Sharma, A. K.; and Zaveri, T. H., "A Survey of Automated Biometric Authentication Techniques" Nirma University International Conference on Engineering (NUiCONE), 2013, Page(s): 1-6 (DOI: 10.1109/NUiCONE.2013.6780190), which is incorporated herein by reference. U.S. Pat. No. 8,229,178 issued Jul. 24, 2012 to Zhang et al., which is incorporated herein by reference, describes a method for acquiring a palm vein image with visible and infrared light and extracting features from the image for authentication of individual identity. Biometric identification can be based on imaging of the retina or iris, as described in U.S. Pat. No. 5,572,596 issued to Wildes et al. on Nov. 5, 1996 and U.S. Pat. No. 4,641,349 issued to Flom et al. on Feb. 3, 1987, each of which is incorporated herein by reference. Combinations of several types of identity signals can also be used (e.g., speech and video, as described in Aleksic, P. S. and Katsaggelos, A. K. "Audio-Visual Biometrics," Proceedings of the IEEE Volume: 94, Issue: 11, Page(s): 2025-2044, 2006 (DOI: 10.1109/JPROC.2006.886017), which is incorporated herein by reference).

In an aspect, image processing circuitry 3408 includes eye tracking module 3460, which determines an eye position or eye movement from user image 3412, based upon one or more parameter 3416. For example, a gaze tracking system for monitoring eye position is available from Seeing Machines Inc., Tucson, Ariz. (see e.g., the Specification Sheet: "faceLAB™ 5 Specifications" which is incorporated herein by reference). Eye position, eye rotation, eye gaze position against screen, pupil diameter and eye vergence distance may be monitored. Eye rotation measurements of up to +/−45 degrees around the y-axis and +/−22 degrees around the x-axis are possible. Typical static accuracy of gaze direction measurement is 0.5-1 degree rotational error. Eye position can be sensed using a method and system as described in U.S. Pat. No. 8,808,195 to Tseng et al., which is incorporated herein by reference, or by other methods described herein or known to those skilled in the relevant art. Eye position may include static or fixed eye position/gaze direction or dynamic eye position/eye movement. In an aspect, eye tracking module 3460 detects pupil diameter. Pupil diameter can be measured, for example, by methods as described in U.S. Pat. No. 6,162,186 to Scinto et al., which is incorporated herein by reference.

Ear stimulation device control system 3400 may include various other components as described generally elsewhere herein, including, but not limited to, e.g., communication circuitry 3462, data storage circuitry 3464, and reporting circuitry 3466. Similarly, ear stimulation device 3432 may include additional components, including but not limited to communication circuitry 3468 and stimulator driver circuitry 3470. In addition, ear stimulation device 3432 may include or be used in combination with a securing member 3472. In an aspect, the securing member includes or is a portion of an earpiece.

Figure 35:
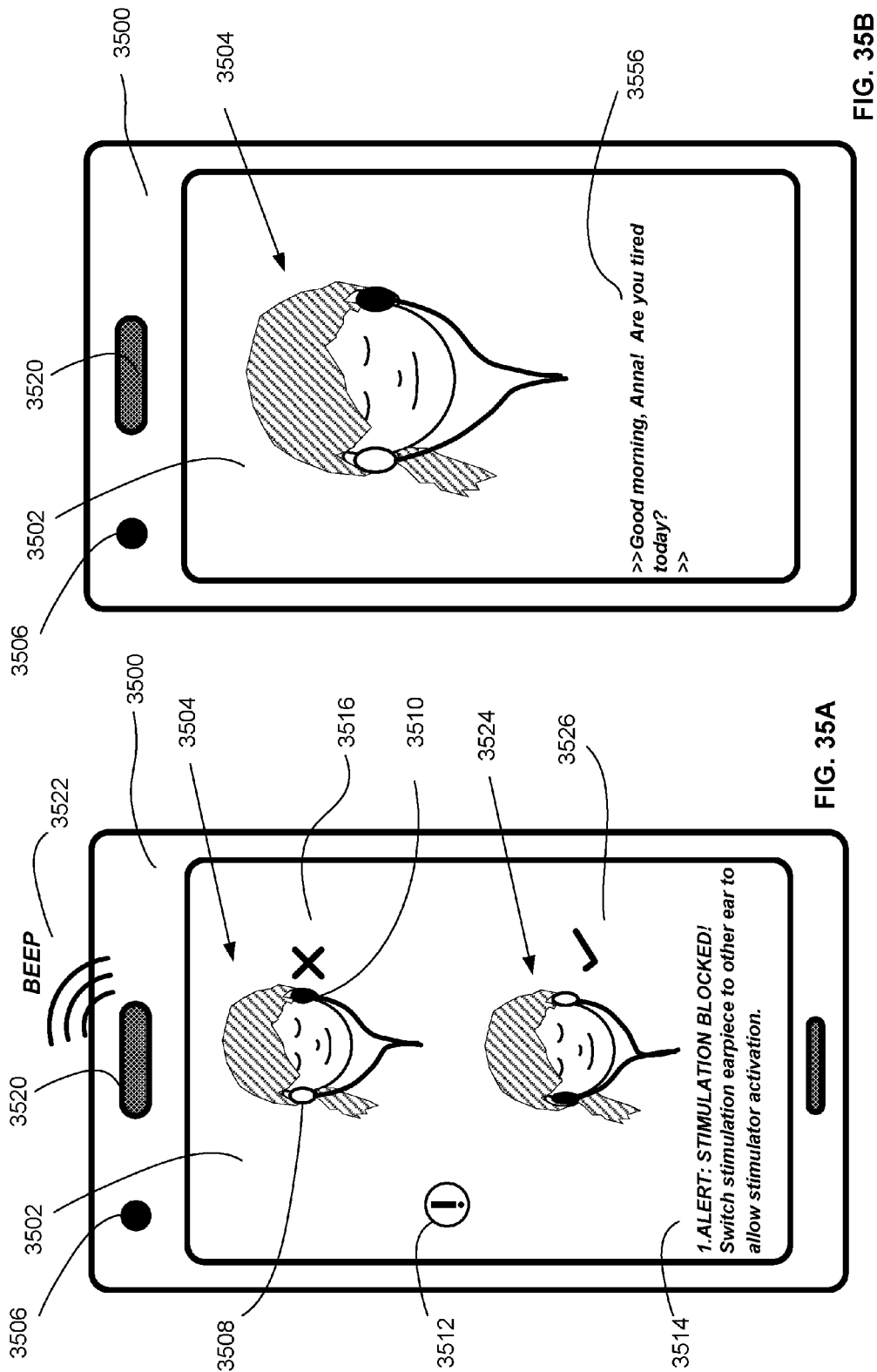
FIG. 35A depicts a user interface for a neural stimulation system.
FIG. 35B depicts a user interface for a neural stimulation system.

FIGS. 35A and 35B show examples of user interfaces used in connection with an ear stimulation device control system implemented on a personal computing device, and in particular illustrate ways in which processing of a user image captured with a user-facing camera is used in control of the ear stimulation device. In the example of FIG. 35A, the personal computing device is a smart phone 3500 configured with application software that notifies the user of improper placement of the earpieces. Detection and notification is performed, e.g. as described in connection with FIGS. 30-34. Delivery of text, visible, and audio notifications to the user (e.g., as in the method of FIG. 33) are illustrated in FIG. 35A. In the systems shown in FIGS. 35A and 35B, the ear stimulation device itself is not depicted, but it would be connected to smart phone 3500, e.g. via an audio jack. Touchscreen 3502 of smart phone 3500 functions as a user interface (e.g., user interface 3444 in FIG. 34). User image 3504, captured with user-facing camera 3506 is displayed on touchscreen 3502. Image analysis of user image 3504 is performed by image processing circuitry (e.g., image processing circuitry 3408 in FIG. 34), to determine whether the earpiece including the ear stimulation device is positioned properly. In an aspect, proper positioning of the ear stimulation device means that the earpiece is located on the correct ear, and in some cases also means that the earpiece is located in the proper position on the ear. In the example of FIG. 35A, earpieces 3508 and 3510 in user image 3504 are different colors, allowing the two earpieces to be distinguished. Alert symbol 3512 (an exclamation point in a circle) notifies the user of an alert message, which is delivered via alert text 3514 displayed on touchscreen 3502. In this case, alert text 3514 provides the alert message "1. ALERT: STIMULATION BLOCKED! Switch stimulation earpiece to other ear to allow stimulator activation." An 'X' 3516 (or other marker) displayed next to user image 3504 indicates to the user that earpieces 3508 and 3510 are positioned incorrectly. An audible notification 3522 (e.g., a 'beep') delivered by speaker 3520 is also provided to attract the user's attention to the incorrectly positioned earpieces. A second user image 3524, serving as an exemplar depicting correctly placed earpieces, is also presented on touchscreen 3502. The colors of earpieces in image 3524 may be enhanced or highlighted in the image to emphasize the importance of placing an earpiece of a particular color at a particular ear. A check mark 3526 (or other marker) is used to indicate that second user image 3524 depicts correct earpiece position. Check mark 3526 may be animated, e.g. to switch from flashing to solid or change color from red to green when the user has switched the earpieces to the proper positions. Once the earpieces are properly positioned, the ear stimulation device control system, implemented with smart phone 3500, controls the ear stimulation device to deliver a stimulus to the ear of the subject, as described elsewhere herein.

As described in connection with FIG. 34, in an aspect ear stimulation device control system 3400 includes emotion determination module 3454, physiological condition module 3456, identity determination module 3458 and eye tracking module 3460. These modules can be used to determine additional information about the user on which to base control of the ear stimulation device. In FIG. 35B, touchscreen 3502 of smart phone 3500 functions as a user interface. User image 3504, captured with user-facing camera 3506 is displayed on touchscreen 3502. Image analysis of user image 3504 is performed by image processing circuitry 3408 as shown in FIG. 34, to determine the identity of the user, and potentially also the emotion and physiological status of the user, as discussed herein above. After the identity of the user has been determined, user-specific information can be used to determine neural stimulation. For example, stimulus level settings that have been optimized for the user can be retrieved from memory and used to configure the ear stimulation device. In addition, the stimulus delivered with the stimulation device may be adjusted depending upon the mood or physiological status of the user.

In addition, in an aspect, application software on smart phone 3500 prompts the user to enter additional information regarding mood or other parameters, similar to application software 2908 described in connection with FIG. 29. In the example of FIG. 35B, the mood of the subject may not be readily determined from the relatively neutral expression of the user in image 3504. However, the application software may prompt the user to enter to enter information regarding mood or other feelings. For example, text prompt 3556 "Good morning, Anna! Are you tired today?" might be followed by additional questions, depending on the user's response, in order to determine how the user is feeling. The use of application software to assess the mood of the user is discussed in greater detail elsewhere herein.

Figure 36:
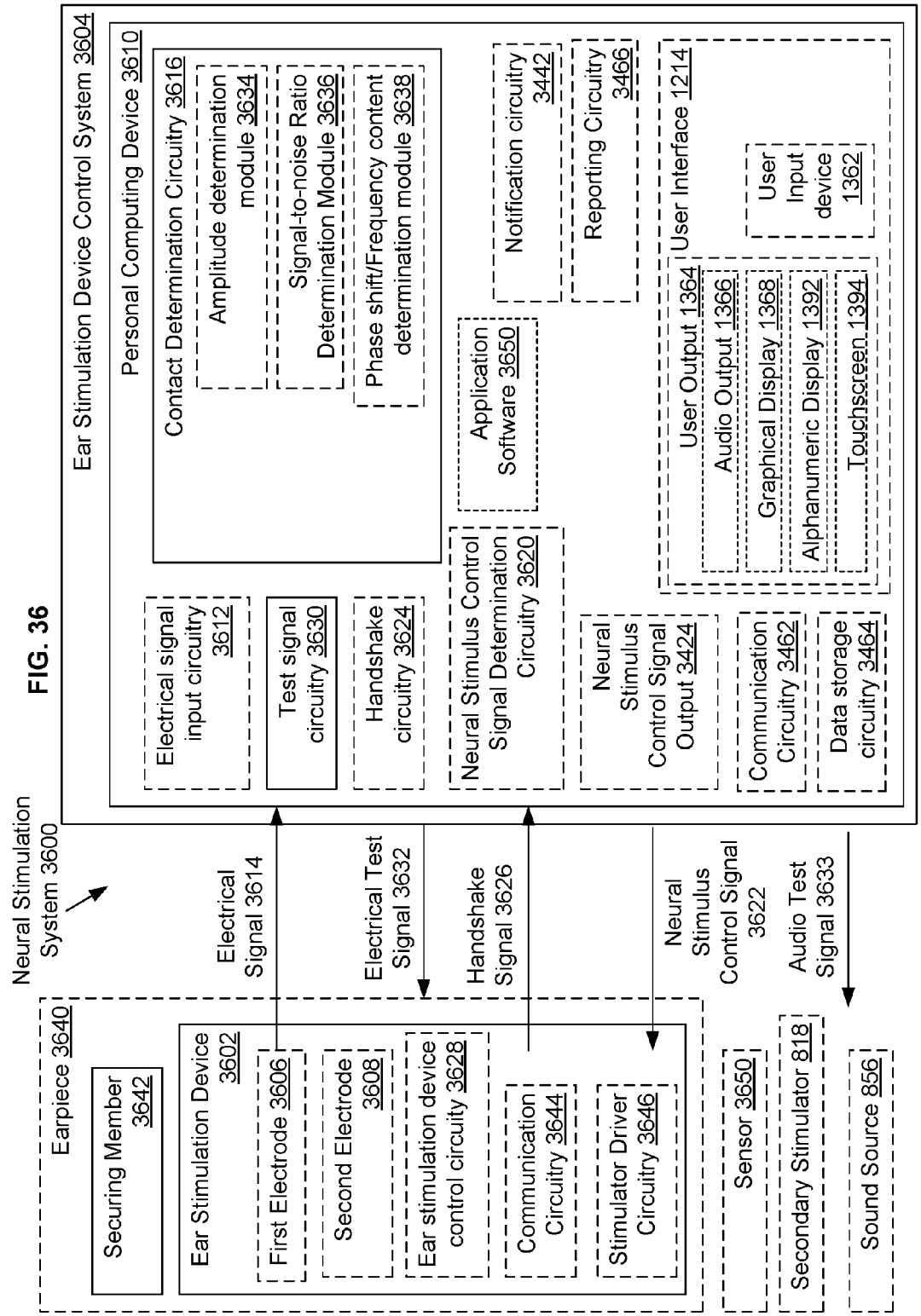
FIG. 36 is a block diagram of an embodiment of a neural stimulation system.

As discussed herein above, in an aspect, image detection and analysis is used to detect improper placement of one or more earpieces on the ear(s) of a user of a personal computing device. In some aspects, it is desirable to detect quality of electrical contact between the ear and an electrode used for delivering electrical stimuli to or sensing electrical signals from the ear. FIG. 36 is a block diagram depicting neural stimulation system 3600, which includes ear stimulation device 3602 and ear stimulation device control system 3604. FIG. 36 depicts further aspects of a neural stimulation system 3600 including an ear stimulation device control system 3604, used for controlling an ear stimulation device 3602 that delivers electrical stimuli via one or more electrodes 3606 and 3608. Ear stimulation device control system 3604 determines whether the one or more electrodes 3606 and 3608 are in good electrical contact with the ear of the user and notifies the user of the status of electrodes 3606 and 3608 so that adjustments can be made, as needed. In addition, delivery of a stimulus via the electrode can be prevented if it is determined that there is not a good electrical contact between the electrode and the ear. Ear stimulation device control system 3604 includes a personal computing device 3610 configured to control delivery, via ear stimulation device 3602, of a stimulus to at least one nerve innervating an ear of a user of personal computing device 3610. Ear stimulation device 3602 includes at least one first electrode 3606. Personal computing device 3610 includes electrical signal input circuitry 3612 adapted to receive an electrical signal 3614 indicative of electrical contact of the at least one first electrode 3606 with the ear of a user of the personal computing device 3610. Personal computing device 3610 includes contact determination circuitry 3616 configured to determine whether the at least one first electrode 3606 is in good electrical contact with the ear of the user, and neural stimulus control signal determination circuitry 3620 configured to send a neural stimulus control signal 3622 from personal computing device 3610 to ear stimulation device 3602 to prevent delivery of the stimulus if the at least one first electrode 3606 is not in good electrical contact with the ear of the user. In addition, personal computing device 3610 includes notification circuitry 3622 configured to deliver a notification to the user relating to the status of the at least one first electrode 3606. Personal computing device 3610 may be, for example, a phone, watch, wearable device, tablet computer, laptop computer, or desktop computer.

In an aspect, ear stimulation device control system 3604 includes handshake circuitry 3624 adapted to receive a handshake signal 3626 from ear stimulation device control circuitry 3628 associated with ear stimulation device 3602. In an aspect, ear stimulation device control system 3604 includes test signal circuitry 3630 configured to deliver an electrical test signal 3632 via at least one second electrode 3608 of the at least one ear stimulation device 3602, and detecting the electrical signal 3614 via the at least one first electrode 3606 responsive to electrical test signal 3632. In an aspect, contact determination circuitry 3616 is configured to determine an electrical impedance between the at least one first electrode 3606 and the at least one second electrode 3608. In an aspect, contact determination circuitry 3616 is configured to determine an amplitude of electrical signal 3614. In an aspect, contact determination circuitry 3616 is configured to determine a signal-to-noise ratio of electrical signal 3614. In an aspect, contact determination circuitry 3616 is configured to determine a phase shift or frequency content of the electrical signal 3614. In various aspects, contact determination circuitry 3616 includes amplitude determination module 3634 for determining the amplitude of electrical signal 3614, signal-to-noise ratio determination module 3636 for determining the signal-to-noise ratio of electrical signal 3614, or phase shift/frequency content determination module 3638 for determining the phase shift or frequency content of electrical signal 3614.

In an aspect, ear stimulation device 3602 includes earpiece 3640 which includes the at least one first electrode 3606. In an aspect, notification circuitry 3622 is configured to instruct the user to reposition earpiece 3640, replace at least a portion of the at least one first electrode 3606, clean at least a portion of the at least one first electrode 3606, moisten at least a portion of the at least one first electrode 3606, or apply gel to at least a portion of the at least one first electrode 3606. As discussed herein above, in various aspects, ear stimulation device 3602 includes or is used in connection with a securing member 3642, and may include additional circuitry components as described elsewhere herein, e.g. communication circuitry 3644 and stimulator driver circuitry 3646. In an aspect, notification circuitry 3622 is configured to deliver one or more of a text notification, a visible notification, or an audio notification. Neural stimulation system 3600 in various aspects includes other components as described elsewhere herein. For example, in various aspects personal computing device 3610 includes user interface 1214 including user input device 1362 and user output 1364, including audio output 1366, graphical display 1368, alphanumeric display 1392, or touchscreen 1394, as depicted in and described in connection with FIG. 13, for example. In various aspects, ear stimulation device control system includes neural stimulus control signal output 3424, communication circuitry 3462, data storage circuitry 3464, as in connection with FIG. 34. In various aspects, neural stimulation system 3600 includes one or more sensor 3650, which may include, for example, a neural signal sensor, other physiological sensor, an environmental sensor, a motion sensor, a location sensor, of various types as described in connection with neural signal sensor 702 or secondary sensor 750 in FIG. 7. In some aspects, neural stimulation system 3600 includes a secondary stimulator 818, for example as described in connection with FIG. 7. In some aspects, neural stimulation system 3600 includes a sound source 856, e.g. as described in connection with FIG. 7. Notification circuitry 3442 and reporting circuitry 3466 are as described in connection with FIG. 34. Personal computing device 3610 is configured with application software 3650, including but not limited to the various modules described specifically herein.

Figure 37:
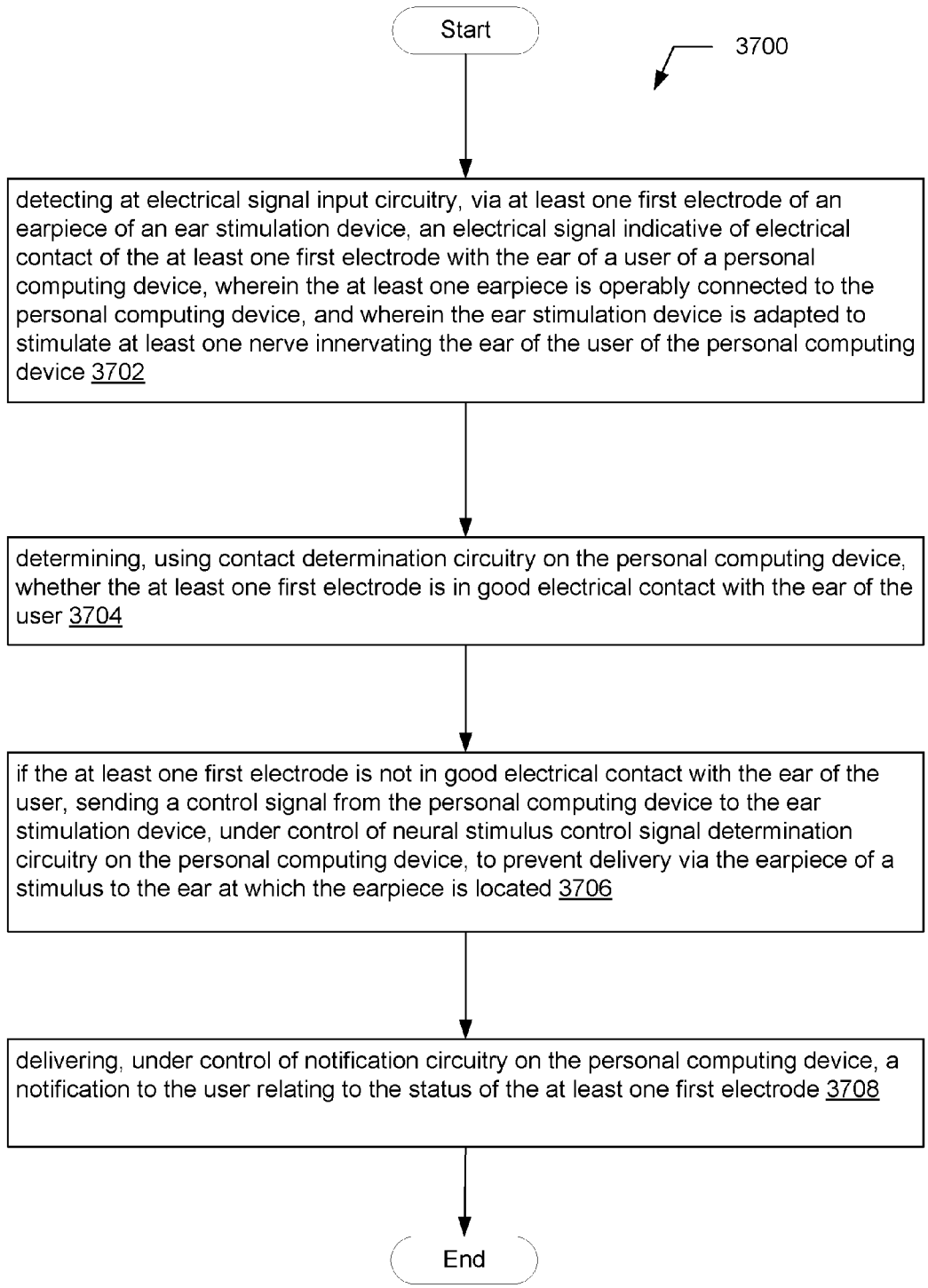
FIG. 37 is a flow diagram of a method.

FIG. 37 depicted a method of controlling an ear stimulation device with a personal computing device, responsive to detection of contact between an electrode and the ear of the user, as described in connection with FIG. 36. As noted above, the personal computing device may be, for example, a phone, watch, wearable device, tablet computer, laptop computer, or desktop computer. Method 3700 includes detecting at electrical signal input circuitry, via at least one first electrode of an earpiece of an ear stimulation device, an electrical signal indicative of electrical contact of the at least one first electrode with the ear of a user of a personal computing device, wherein the at least one earpiece is operably connected to the personal computing device, and wherein the ear stimulation device is adapted to stimulate at least one nerve innervating the ear of the user of the personal computing device, as indicated at 3702; determining, using contact determination circuitry on the personal computing device, whether the at least one first electrode is in good electrical contact with the ear of the user, as indicated at 3704; if the at least one first electrode is not in good electrical contact with the ear of the user, sending a control signal from the personal computing device to the ear stimulation device, under control of neural stimulus control signal determination circuitry on the personal computing device, to prevent delivery via the earpiece of a stimulus to the ear at which the earpiece is located, as indicated at 3706; and delivering, under control of notification circuitry on the personal computing device, a notification to the user relating to the status of the at least one first electrode, as indicated at 3708.

Determining whether the at least one first electrode is in good electrical contact with the ear of the user can be performed by various methods, as discussed herein below. Good electrical contact can be defined by setting a threshold value for one or more measured parameter, such that contact is defined to be "good" if the measured parameter(s) are at or above the threshold value and "bad" if they are below the threshold parameter. In an aspect, determining whether the at least one first electrode is in good electrical contact includes providing a rating of the contact quality, e.g., "strong," "moderate," "usable but weak," "unusable," wherein any usable contact qualities are considered "good," but contacts that are not usable are considered "bad."

Figure 38:
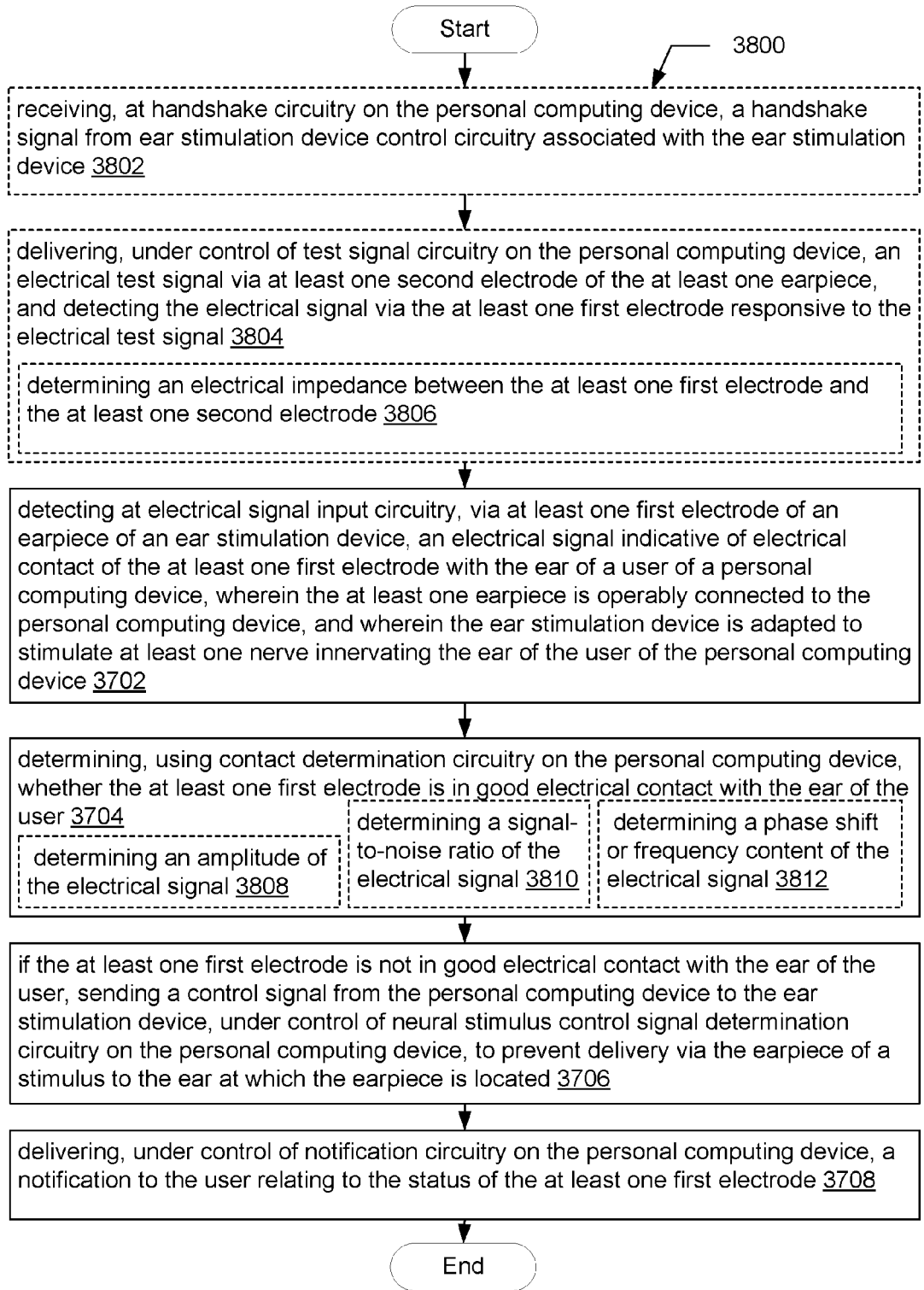
FIG. 38 is a flow diagram of a method.
Figure 39:
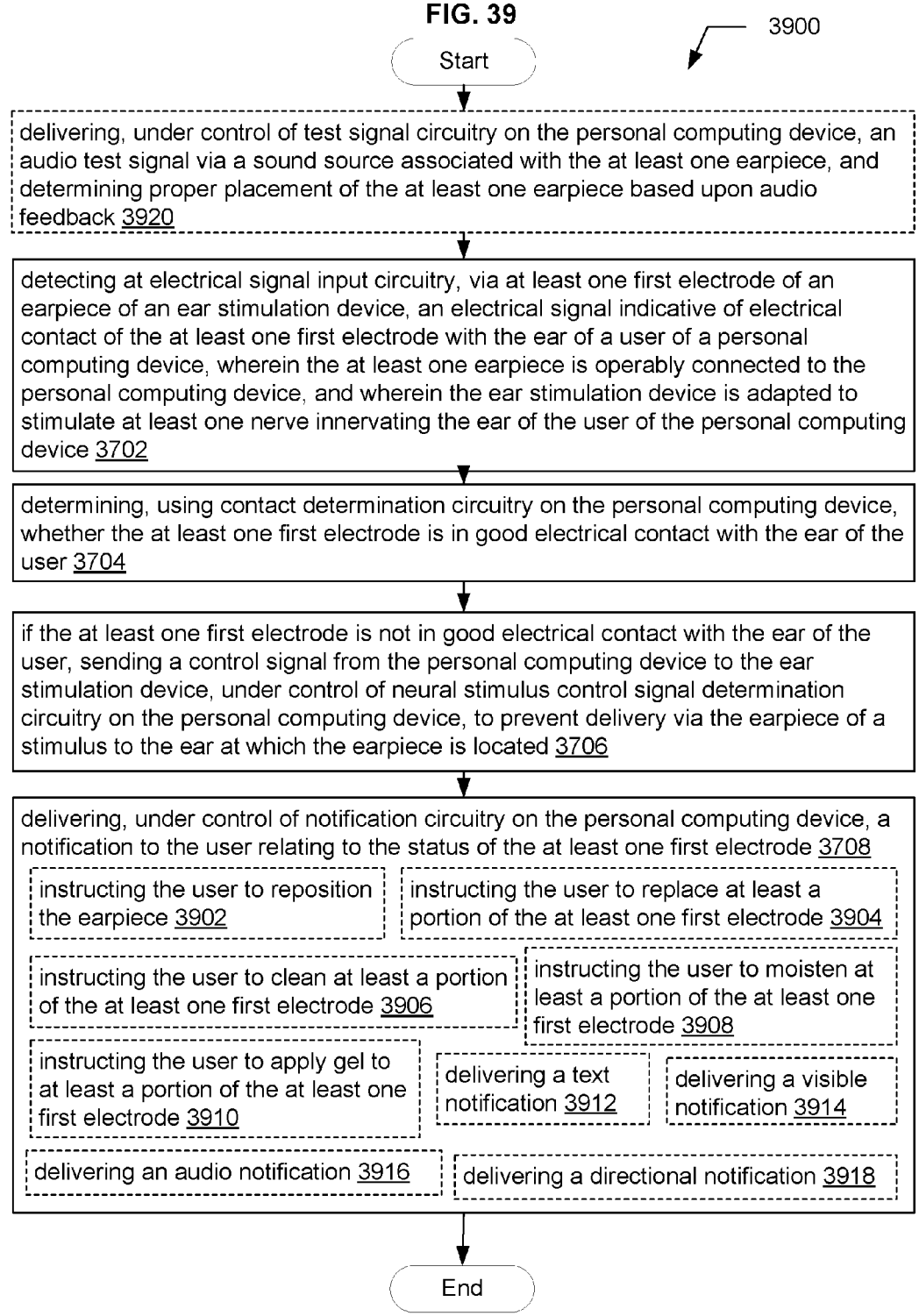
FIG. 39 is a flow diagram of a method.

Further aspects and variants of method 3700 are depicted in FIGS. 38-39. In these figures, steps 3702, 3704, 3706, and 3708 are the same as in FIG. 37.

FIG. 38 depicts a method 3800, which includes further elaborations of the method of FIG. 37. Steps 3702, 3704, 3706 and 3708 are as described in connection with FIG. 37. In an aspect, method 3800 includes receiving, at handshake circuitry on the personal computing device, a handshake signal from ear stimulation device control circuitry associated with the ear stimulation device, as indicated at 3802. In another aspect, method 3800 includes delivering, under control of test signal circuitry on the personal computing device, an electrical test signal via at least one second electrode of the at least one earpiece, and detecting the electrical signal via the at least one first electrode responsive to the electrical test signal, as indicated at 3804. This may include, for example, determining an electrical impedance between the at least one first electrode and the at least one second electrode, as indicated at 3806. In various aspects, determining whether the at least one first electrode is in good electrical contact with the ear of the user (at 3704) includes determining an amplitude of the electrical signal, as indicated at 3808, determining a signal-to-noise ratio of the electrical signal, as indicated at 3810, or determining a phase shift or frequency content of the electrical signal, as indicated at 3812.

FIG. 39 depicts a method 3900, including further variants of the method shown in FIG. 37, relating to delivering a notification to the user regarding the status of the at least one first electrode. In various aspects, delivering the notification to the user includes instructing the user to reposition the earpiece, as indicated at 3902, instructing the user to replace at least a portion of the at least one first electrode, as indicated at 3904, instructing the user to clean at least a portion of the at least one first electrode, as indicated at 3906, instructing the user to moisten at least a portion of the at least one first electrode, as indicated at 3908, or instructing the user to apply gel to at least a portion of the at least one first electrode, as indicated at 3910. In other aspects, delivering the notification to the user includes delivering a text notification, as indicated at 3912, delivering a visible notification, as indicated at 3914, delivering an audio notification, as indicated at 3916, or delivering a directional notification, at 3918. Notifications can be delivered, for example, as described in connection with FIG. 31, or as illustrated in FIG. 35A. In another aspect, method 3900 includes delivering, under control of test signal circuitry on the personal computing device, an audio test signal via a sound source associated with the at least one earpiece, and determining proper placement of the at least one earpiece based upon audio feedback, as indicated at 3920. In an aspect, audio feedback is determined from an audio signal detected from the earpiece, which will vary depending upon the placement of the earpiece, e.g. whether or not it is firmly seated within the ear canal. In an aspect, audio feedback is determined from the user, e.g. the user self-reporting of audio quality.

Figure 40:
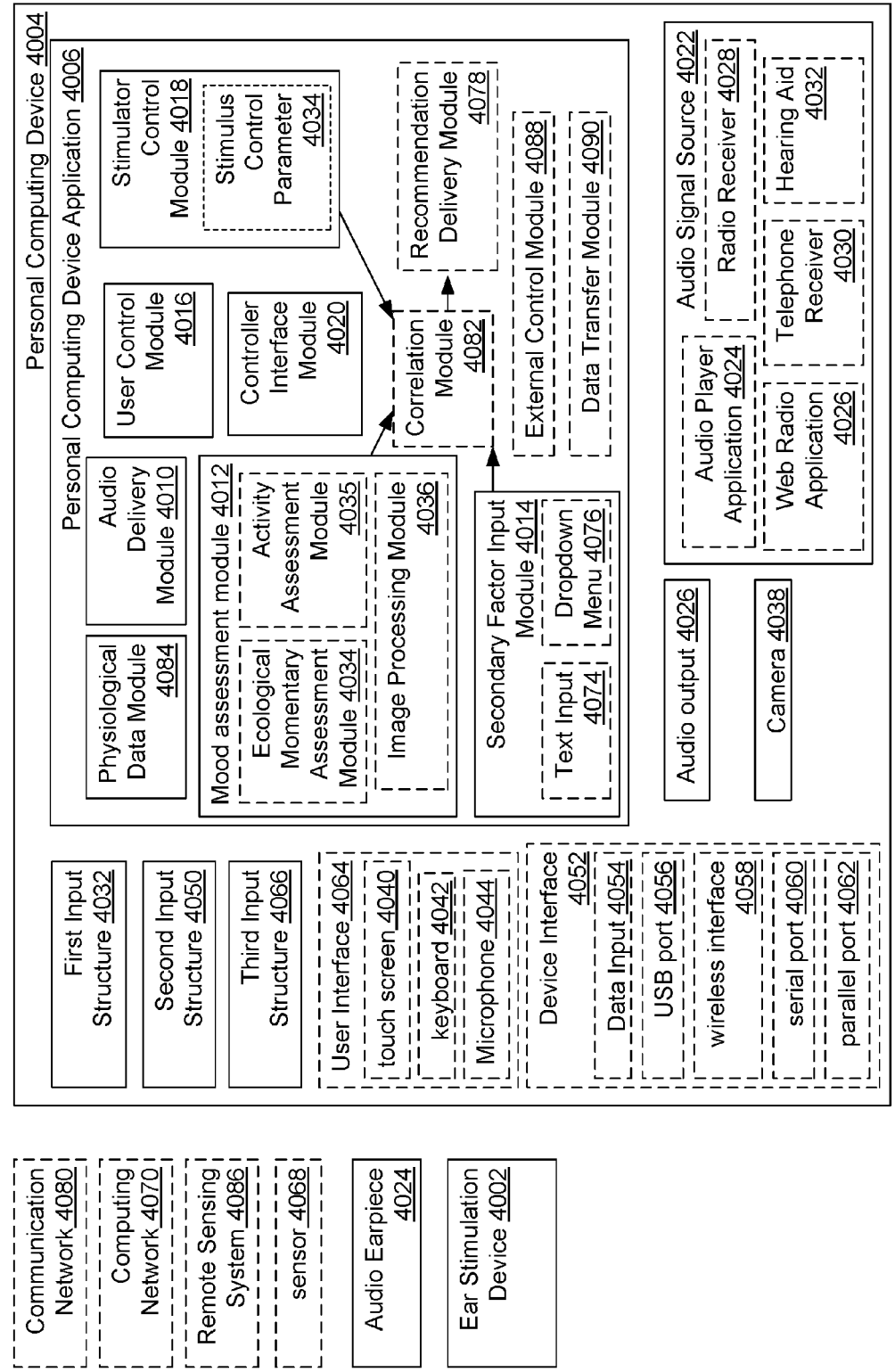
FIG. 40 is a block diagram of a system including a personal computing device.

FIG. 40 illustrates a nerve stimulation system 4000 including ear stimulation device 4002 and personal computing device 4004, which is configured personal computing device application 4006 for monitoring use of nerve stimulation system 4000 by a user. As in other examples presented herein, personal computing device 4004 may be, for example a phone, watch, wearable device, tablet computer, laptop computer, or desktop computer. Aspects of nerve stimulation system 4000 not described in detail in connection with FIG. 40 are generally as described in connection with other embodiment depicted and described herein.

Personal computing device application 4006 includes audio delivery module 4010, mood assessment module 4012, secondary factor input module 4014, user control module 4016, stimulator control module 4018, and controller interface module 4020. The various modules include application software operating in connection with personal computing device hardware and software (i.e. the personal computing device hardware is configured by the application software) to provide the module functionality. Personal computing device 4006 includes other hardware and software components as described elsewhere herein as well as conventional hardware and software components not specifically described herein. The term "module," as used herein, refers to application software operating on and used to configure personal computing device hardware to provide specialized circuitry functions of the device. In general, a module utilizes and in an aspect can be considered to incorporate both data storage circuitry and processing circuitry of the personal computing device.

Audio delivery module 4010 is adapted to control delivery of an audio signal from an audio signal source 4022 to an audio earpiece 4024 via an audio output 4026 of the personal computing device 4004, the audio earpiece 4024 having associated therewith ear stimulation device 4002 configured to stimulate a nerve innervating the ear of the user. Audio signal source 4022 may be, for example an audio player application 4024, a web radio application 4026, a radio receiver 4028, a telephone receiver 4030, or a hearing aid 4031.

Mood assessment module 4012 is adapted to receive mood-related input from the user via a first input structure 4032 associated with the personal computing device, and assess a mood of the user based at least in part upon the mood-related input. In an aspect, mood assessment module 4012 includes an ecological momentary assessment module 4034. Ecological momentary assessment module 4034 includes application software on the person computing device that collects information about the user's behaviors and experiences from the user, by querying the user at intervals during the day as they go about their usual activities in their "natural environment" (as contrasted to self-reports of mood based on the user's recollections during a clinic visit, for example), e.g. as described generally in Shiffman et al., "Ecological Momentary Assessment," Annual Review of Clinical Psychology, Vol. 4:1-32, April 2008 (First Published Online Nov. 28, 2007), DOI: 10.1146/annurev.clinpsy.3.022806.091415, which is incorporated herein by reference. In some aspects, mood assessment module 4012 includes activity assessment module 4035, which tracks and analyzes user activities involving use of the personal computing device (e.g. use of social media, web searches, speech patterns, typing patterns, including amount and/or type of use) to determine mood of the user. For example, in an aspect, activity assessment module 4035 analyzes typing patterns using, for example, techniques as described in U.S. Pat. No. 6,231,344 to Merzenich et al., U.S. Published Patent Application 2005/0084832 to Janssen et al., each of which is incorporated herein by reference. In an aspect, activity assessment module 4035 determines the timing of entry of instructions by the patient. In an aspect, it is not necessary to determine the specific instructions entered by the patient, but only to determine how often the patient is using the personal computing device, and/or how quickly the patient is entering instructions into the personal computing device. In other aspects, the specific instructions can be detected, e.g., to determine whether the patient is choosing to listen to music, play a game, send or read email, receive a phone call, or place a phone call. Sensing and processing of game controller signals, e.g., to determine reaction times, may be substantially as described in U.S. Pat. No. 5,913,310 to Brown, or U.S. Pat. No. 6,186,145 to Brown, both of which are incorporated herein by reference. It will be appreciated that while Brown describes a video game designed primarily for health care-related teaching purposes, the video game may be for entertainment purposes, and need not include an educational or medical component. In an aspect, activity assessment module 4035 is configured to process an audio signal (detected from a cell phone, for example) to determine a speech pattern of the patient. In an aspect, mood assessment module 4012 includes image processing module 4036 adapted to determine a mood of the user based on image analysis of an image of the user detected with a user-facing camera 4038 of the personal computing device 4004, e.g., as discussed herein above. In various aspects, mood assessment module 4012 is adapted to receive mood-related input relating to depression, stress, or emotion, for example. First input structure 4032 of the personal computing device in various aspects includes a touch screen 4040, a keyboard, or a microphone.

Secondary factor input module 4014 is adapted to receive at least one input relating to at least one secondary factor relating to the user via a second input structure 4050 associated with personal computing device 4004. Secondary input structure 4050 of personal computing device 4004 includes at least one of a touch screen 4040, a keyboard 4042, a microphone 4044, a device interface 4052, a data input 4054, USB port 4056, a wireless interface 4058, a serial port 4060, and a parallel port 4062. Touch screen 4040, a keyboard 4042, a microphone 4044, are examples of components of a user interface 4064, although it will be appreciated that input may be received by other types of user interface devices, as are known to those of skill in the art. Data input 4054, USB port 4056, wireless interface 4058, serial port 4060, and parallel port 4062 are examples of device interface 4052; other device interfaces may be used as well. First input structure 4032, second input structure 4050, and third input structure 4066 may in some aspects be the same type of input structure, and indeed may be the same input structure. In other aspects, one or more of first input structure 4032, second input structure 4050, and third input structure 4066 are the same type of input structure, but are distinct input structures. In some aspects, first input structure 4032, second input structure 4050, and third input structure 4066, are different types of input structures, and, in addition, are distinct input structures.

In an aspect, secondary factor input module 4014 is adapted to receive at least one input from the user, i.e., via user interface 4064. In another aspect, secondary factor input module is adapted to receive at least one input from a sensor 4068, e.g., via data input 4054 or another device interface. In another aspect, secondary factor input module 4014 is adapted to receive at least one input via a computing network 4070.

User control module 4016 is adapted to receive at least one user control input via a third input structure 4066 of the personal computing device, the user control input for controlling user-controllable stimulation parameters of the ear stimulation device.

Stimulator control module 4018 is adapted to determine at least one stimulus control parameter based on at least one of the mood of the user, the at least one secondary factor, and the at least one user control input.

Controller interface module 4020 is used for communicating the at least one stimulus control parameter to a stimulator controller adapted to control the ear stimulation device responsive to the at least one stimulus control parameter.

In an aspect, stimulator control module 4018 is configured to coordinate delivery of the audio signal with delivery of at least one stimulus with ear stimulation device 4002.

In an aspect, secondary factor input module 4014 is adapted to receive at least one input relating to an environmental condition of the user, for example, including at least one of a light level, a temperature, a humidity, a pollen count, a noise level, a day length, a precipitation, an air quality measure. In another aspect, secondary factor input module 4014 is adapted to receive at least one input relating to sleep pattern of the user. In another aspect, secondary factor input module 4014 is adapted to receive at least one input relating to medical history of the user. In another aspect, secondary factor input module 4014 is adapted to receive at least one input relating to an activity of the user, including, but not limited to a physical activity, a health-related activity, a recreational activity, a social activity, an employment activity, a purchasing activity, a mental activity, a spiritual activity, a media-related activity, an activity of daily life, an amount of activity, a duration of activity, a frequency of activity, a timing of activity, a calendar, a schedule, or a cost. In another aspect, secondary factor input module 4014 is adapted to receive at least one input relating to a diet of the user or an appetite of the user. An input relating to a secondary factor may include user input relating to the secondary factor, received for example, via user interface 4064. In an aspect, secondary factor input module 4014 is adapted to receive at least one open ended comment from the user, e.g. via text input 4074. In another aspect, secondary factor input module 4014 is adapted to provide a drop down menu 4076 of selectable items and receive from the user a selection from the drop down menu. For example, in an aspect, the menu of selectable items includes topic areas for discussion with a medical care provider. In addition to text inputs or menus, various types of input elements may be utilized to receive input from the user, voice to text conversion, screen elements with clickable buttons or checkboxes that allow the user to select from multiple options, sliders that allow the user to increase or decrease a parameter value between minimum and maximum values, and various other types of input elements.

In an aspect, personal computing device application 4006 includes a recommendation delivery module 4078, which is configured to present a recommendation to the user. For example, the recommendation can be presented to the user via user interface 4064, or audio output 4026, or sent to a remote device via device interface 4052, computing network 4070, or communication network 4080. In an aspect, recommendation delivery module 4078 is adapted to receive the recommendation from a medical care provider, from an insurance company, a service provider, an advisor, a computation-based system, or a social media source. For example, in an aspect recommendation delivery module 4078 is adapted to receive a recommendation via computing network 4070. For example, in an aspect the recommendation based on patients similar to the user. In an aspect, recommendation delivery module 4078 is adapted to generate the recommendation.

In an aspect, personal computing device application 4006 includes a correlation module 4082 configured to determine at least one correlation between the mood of the user and at least one of the at least one secondary factor and the at least one stimulus control parameter, and recommendation delivery module is configured to generate the recommendation based at least in part on the at least one correlation. For example, if it is determined that a particular secondary factor (e.g., rainy weather) is normally followed by a depressed mood in the user, if occurrence of the secondary factor is detected, a recommendation is generated for increasing stimulation. As another example, if a particular activity of the user is correlated with depression (for example, if the user reports being depressed after staying up late and not getting enough sleep, the recommendation might be to go to bed earlier).

In an aspect, recommendation delivery module 4078 is adapted to provide the recommendation to a medical care provider of the user. This can be done, for example, by sending the recommendation to a remote device used by the medical care provider, via computing network 4070, communication network 4080, device interface 4052, or via user interface 4064. Providing the recommendation to the medical care provider makes it possible for the medical care provider to discuss the recommendation with the user, or not, as deemed appropriate by the medical care provider, as well as to incorporate the recommendation into an overall treatment plan for the user.

In an aspect, recommendation delivery module 4078 is configured to generate the recommendation based on at least one of information regarding a response of the subject to a past treatment regimen, information obtained via social media, information regarding at least one preference of at least one social media contact of the subject, information regarding at least one preference of at least one peer of the subject, information regarding at least one preference of at least one role model of the subject, information from an insurance company, information from a service provider.

In an aspect, recommendation delivery module 4078 is configured to generate the recommendation with a computation-based system; for example, an artificial intelligence, a neural network, or a machine learning system. In an aspect, recommendation delivery module 4078 is configured to generate the recommendation based on a predicted response of the subject to a treatment regimen.

In another aspect, recommendation delivery module 4078 is configured to receive information regarding whether the subject has accepted or rejected the recommendation. In various aspects, recommendation delivery module 4078 is configured to present to the user a recommendation for a configuration of the neural stimulus, or a recommendation for a secondary stimulus to be delivered in association with the neural stimulus.

In an aspect, personal computing device application 4006 includes physiological data module 4084 adapted to receive at least one physiological data signal representing at least one physiological parameter of the user. In an aspect, physiological data module 4084 is adapted to receive the at least one physiological data signal from at least one sensor 4068. In another aspect, physiological data module 4084 is adapted to receive the at least one physiological data signal from at least one computing network 4070, or alternatively, via at least one communication network 4080. In another aspect, physiological data module 4084 is adapted to receive the at least one physiological data signal from at least one remote sensing system 4086. A remote sensing system may include one or more sensors in the environment of the user, including but not limited to cameras, motion sensors, pressure sensors, force sensors, infrared sensors, etc. In various aspects, physiological data module 4084 is adapted to receive the at least one physiological data signal from at least one of a blood pressure sensor, a heart rate sensor, a chemical sensor, a biosensor, a pH sensor, a blood oxygen sensor, a galvanic skin response sensor, an EEG sensor, an EMG sensor, an ECG sensor, a wearable item, an eye tracking system, an acoustic sensor, a motion sensor, a force transducer, or an activity sensor.

In an aspect, user control module 4016 is adapted to receive user input (e.g., via user interface 4064) for controlling at least one of stimulus pulse amplitude, stimulus pulse duration, stimulus frequency, stimulus pulse pattern, and stimulus pulse envelope.

In an aspect, personal computing device application 4006 includes external control module 4088, which is configured to receive an external control input for controlling at least one externally controllable stimulation parameter of the ear stimulation device. For example, in various aspects, external control module 4088 is configured to receive the external control input via computing network 4070 or communication network 4080. In an aspect, external control module 4088 is configured to receive the external control input from an external party or entity. In an aspect, the external party or entity is a medical care provider. In other aspects, the external control input may be received from other external parties or entities, e.g., a family member, an insurance company, the device manufacturer, etc. The at least one externally controllable stimulation parameter includes, for example, at least one of stimulus pulse amplitude, stimulus pulse duration, stimulus frequency, stimulus pulse pattern, and stimulus pulse envelope. Externally controllable stimulation parameters may include preferred values for efficacy of treatment, including preferred values to be used in connection with different patent conditions, or upper and lower limits for stimulus values, for purposes of patient safety or efficacy of treatment.

In another aspect, personal computing device application 4006 includes data transfer module 4090 for providing data relating to the user to an external party or entity. In an aspect, data transfer module 4090 is configured to provide the data to the external party or entity via computing network 4070. In another aspect, data transfer module is configured to provide the data to the external party or entity via communication network 4080. For example, the external party or entity may be a medical care provider, a family member, an insurance company, a service provider, a social media contact (or 'friend') of the subject, a peer of the subject, an advisor, a computation based system, a social media source, a device manufacturer, a merchant, an electronic medical record, a sensor network, or an additional program or application, for example. In an aspect, a sensor network includes or is part of a health diary platform, a smart home, or an internet of things.

In an aspect, stimulator control module 4018 is configured to determine the at least one stimulus control parameter 4034 by overriding the at least one user control input for controlling the at least one user-controllable stimulation parameter based on a medical-care provider control input. Alternatively, in another aspect, stimulator control module 4018 is configured to override a medical-care provider control input based on the at least one user control input for controlling the at least one user-controllable stimulation parameter. In yet another aspect, stimulator control module 4018 is configured to override the at least one user control input for controlling the at least one user-controllable stimulation parameter based on a computing system-generated stimulus control parameter. In another aspect, stimulator control module 4018 is configured to override a computing system-generated stimulus control parameter based on the at least one user control input for controlling the at least one user-controllable stimulation parameter. For example, stimulator control module 4018 is configured to determine the at least one stimulus control parameter to provide an initial setting of the ear stimulation device based on the at least one user-controllable stimulation parameter. In another aspect, stimulator control module 4018 is configured to determine the at least one stimulus control parameter to update a setting of the ear stimulation device based on the at least one user-controllable stimulation parameter.

Figure 41:
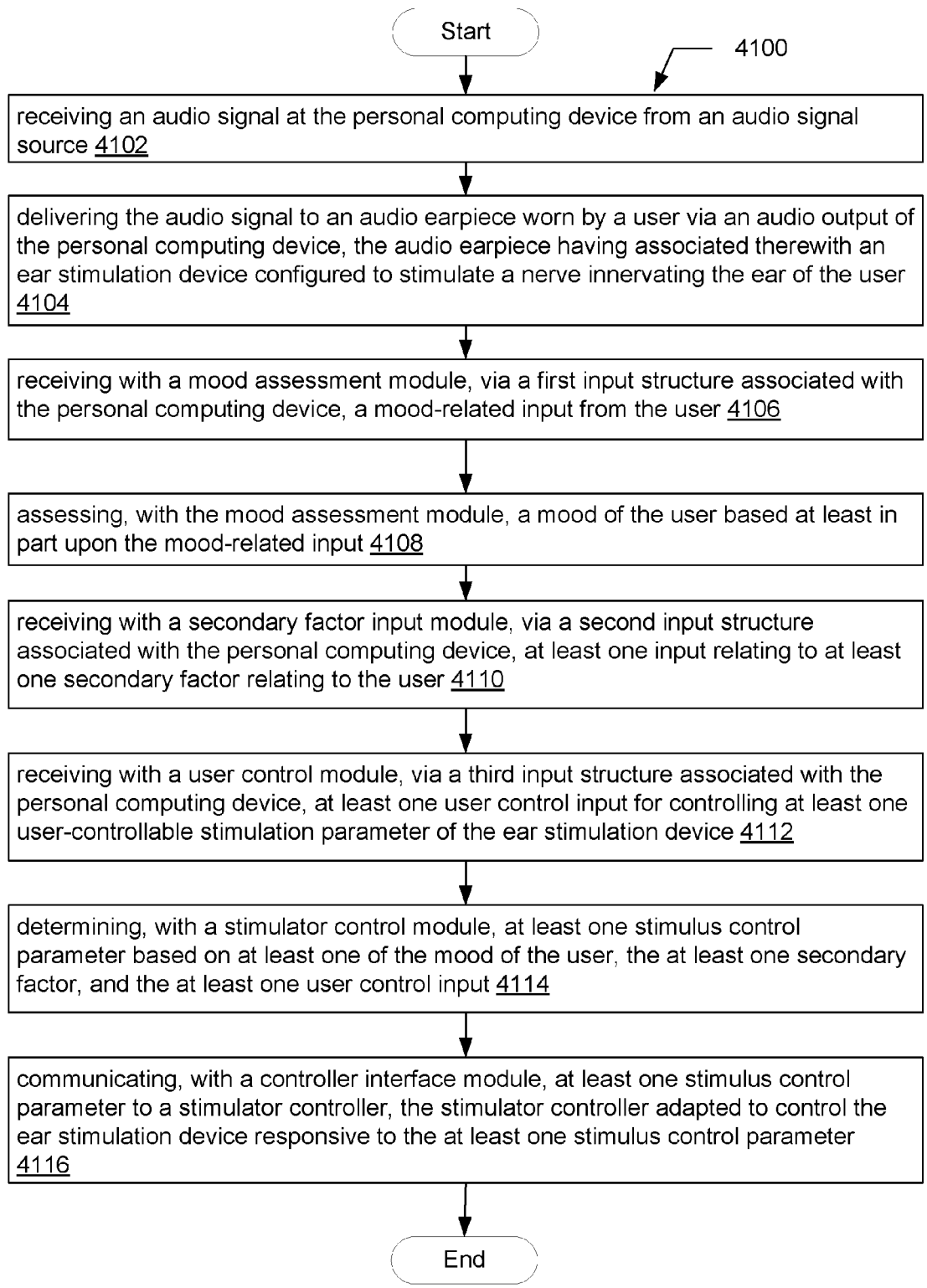
FIG. 41 is a flow diagram of a method.

FIG. 41 is a flow diagram of a method of controlling an ear stimulation device with a personal computing device. Method 4100 may be performed, for example, using a personal computing device configured with application software, as depicted and discussed in connection with FIG. 40. Method 4100 includes receiving an audio signal at the personal computing device from an audio signal source, as indicated at 4102; delivering the audio signal to an audio earpiece worn by a user via an audio output of the personal computing device, the audio earpiece having associated therewith an ear stimulation device configured to stimulate a nerve innervating the ear of the user, as indicated at 4104; receiving with a mood assessment module, via a first input structure associated with the personal computing device, a mood-related input from the user, as indicated at 4106; assessing, with the mood assessment module, a mood of the user based at least in part upon the mood-related input, as indicated at 4108; receiving with a secondary factor input module, via a second input structure associated with the personal computing device, at least one input relating to at least one secondary factor relating to the user, as indicated at 4110; receiving with a user control module, via a third input structure associated with the personal computing device, at least one user control input for controlling at least one user-controllable stimulation parameter of the ear stimulation device, as indicated at 4112; determining, with a stimulator control module, at least one stimulus control parameter based on at least one of the mood of the user, the at least one secondary factor, and the at least one user control input, as indicated at 4114; and communicating, with a controller interface module, at least one stimulus control parameter to a stimulator controller, the stimulator controller adapted to control the ear stimulation device responsive to the at least one stimulus control parameter, as indicated at 4116.

Further aspects of the method shown in FIG. 41 are shown in FIGS. 42-47.

Figure 42:
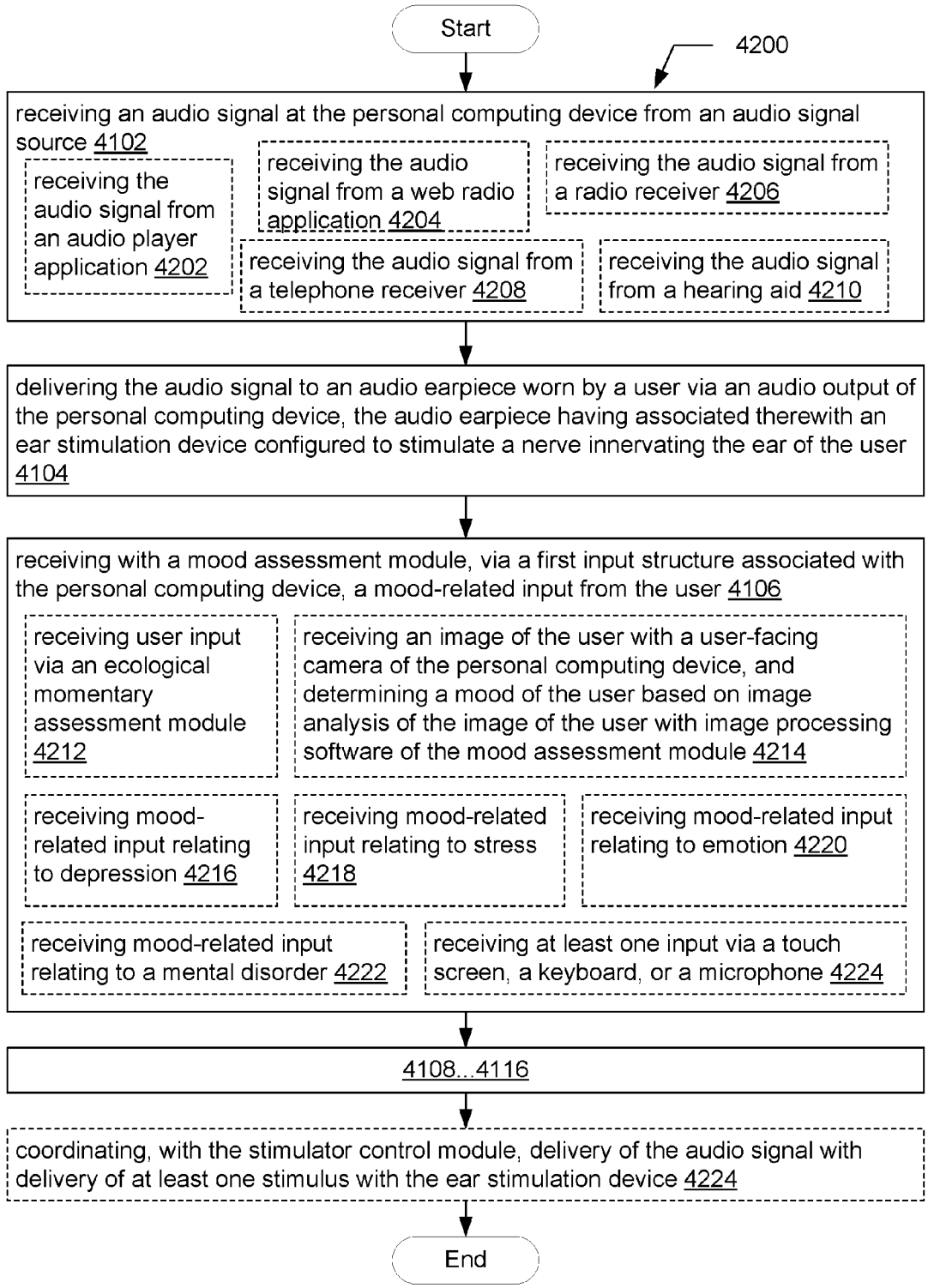
FIG. 42 is a flow diagram of a method.

For example, as shown in FIG. 42, in various aspects of a method 4200, receiving the audio signal at the personal computing device from the audio signal source includes receiving the audio signal from an audio player application, as indicated at 4202; receiving the audio signal from a web radio application, as indicated at 4204; receiving the audio signal from a radio receiver, as indicated at 4206, receiving the audio signal from a telephone receiver, as indicated at 4208, or receiving the audio signal from a hearing aid, as indicated at 4210.

Receiving the mood-related input in various aspects includes receiving user input via an ecological momentary assessment module, as indicated at 4212; receiving an image of the user with a user-facing camera of the personal computing device, and determining a mood of the user based on image analysis of the image of the user with image processing software of the mood assessment module, as indicated at 4214. Mood assessment based on image analysis is discussed in greater detail herein above. Receiving the mood-related input may include receiving mood-related input relating to one or more of depression, as indicated at 4216; stress, as indicated at 4218; emotion, as indicated at 4220; or a mental disorder, as indicated at 4222. In an aspect, receiving the mood-related input via the first input structure includes receiving at least one input via a touch screen, a keyboard, or a microphone, as indicated at 4224. In an aspect, method 4200 includes coordinating, with the stimulator control module, delivery of the audio signal with delivery of at least one stimulus with the ear stimulation device, as indicated at 4224.

Figure 43:
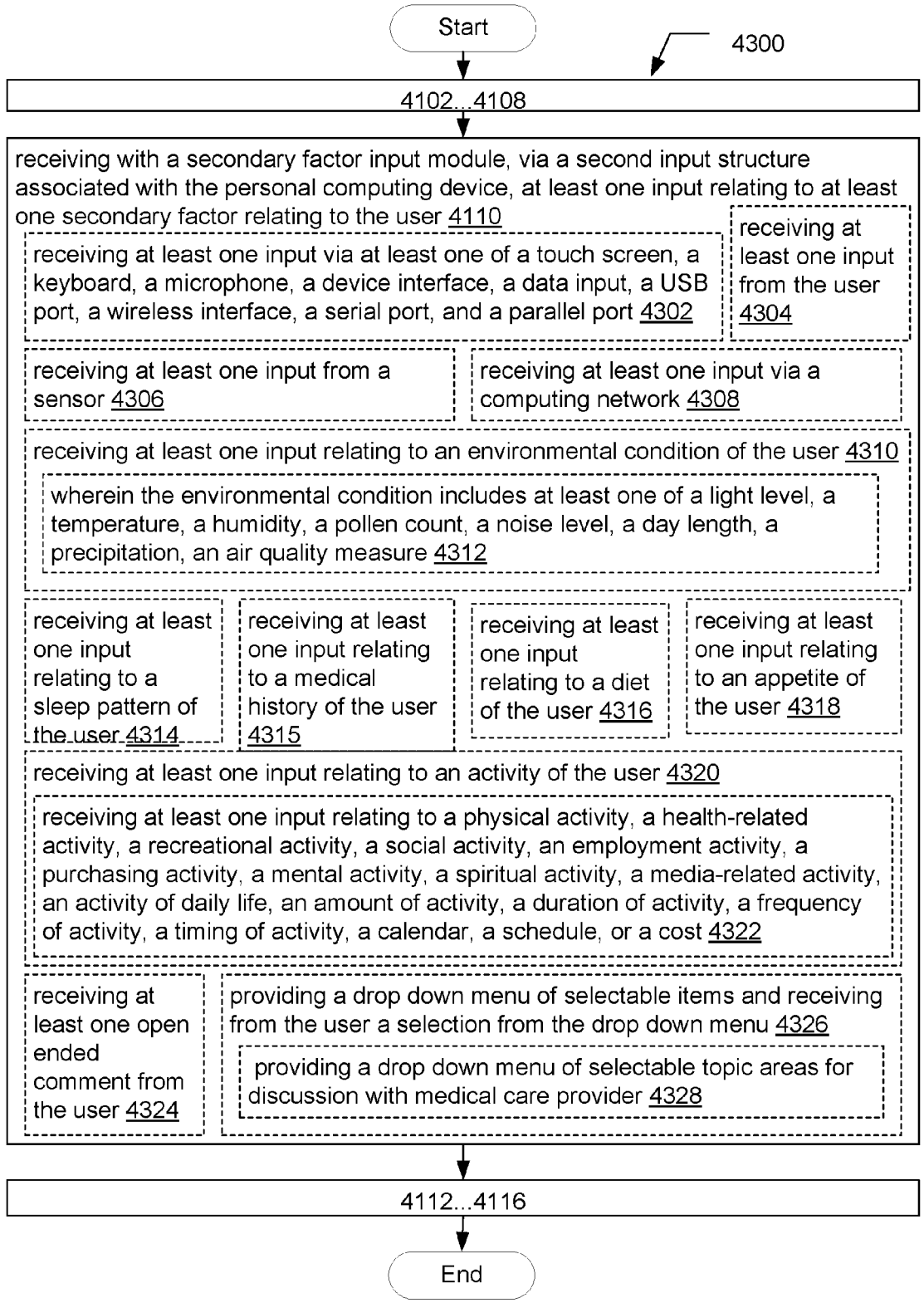
FIG. 43 is a flow diagram of a method.

FIG. 43 provides further variants of the method of FIG. 41, relating to receiving at least one input relating to at least one secondary factor relating to the user, at 4110. In an aspect of method 4300, receiving the at least one input relating to the at least one secondary factor includes receiving at least one input via at least one of a touch screen, a keyboard, a microphone, a device interface, a data input, a USB port, a wireless interface, a serial port, and a parallel port, as indicated at 4302. In further aspects, receiving at least one input relating to at least one secondary factor relating to the user with the secondary factor input module includes receiving at least one input from the user, as indicated at 4304; receiving at least one input from a sensor, as indicated at 4306; or receiving at least one input via a computing network, as indicated at 4308.

In another aspect, receiving at least one input relating to at least one secondary factor relating to the user with the secondary factor input module includes receiving at least one input relating to an environmental condition of the user, as indicated at 4310. An environmental condition may include, for example, at least one of a light level, a temperature, a humidity, a pollen count, a noise level, a day length, a precipitation, an air quality measure, as indicated at 4312.

In other aspects, receiving at least one input relating to at least one secondary factor relating to the user with the secondary factor input module includes receiving at least one input relating to a sleep pattern of the user, as indicated at 4314; a medical history of the user, as indicated at 4315; a diet of the user, as indicated at 4316; an appetite of the user, as indicated at 4318; or an activity of the user, as indicated at 4320. For example, receiving at least one input relating to an activity includes receiving at least one input relating to, e.g., a physical activity, a recreational activity, a social activity, an employment activity, a purchasing activity, a mental activity, a spiritual activity, a media-related activity, an activity of daily life, an amount of activity, a duration of activity, a frequency of activity, a timing of activity, a calendar, a schedule, or a cost, as indicated at 4322.

In further aspect, receiving at least one input relating to at least one secondary factor relating to the user with the secondary factor input module includes receiving at least one open ended comment from the user, as indicated at 4324. In other aspects, receiving at least one input relating to at least one secondary factor relating to the user with the secondary factor input module includes providing a drop down menu of selectable items and receiving from the user a selection from the drop down menu, as indicated at 4326. For example, in an aspect, providing a drop down menu of selectable items includes providing a drop down menu of selectable topic areas for discussion with medical care provider, as indicated at 4328.

Figure 44:
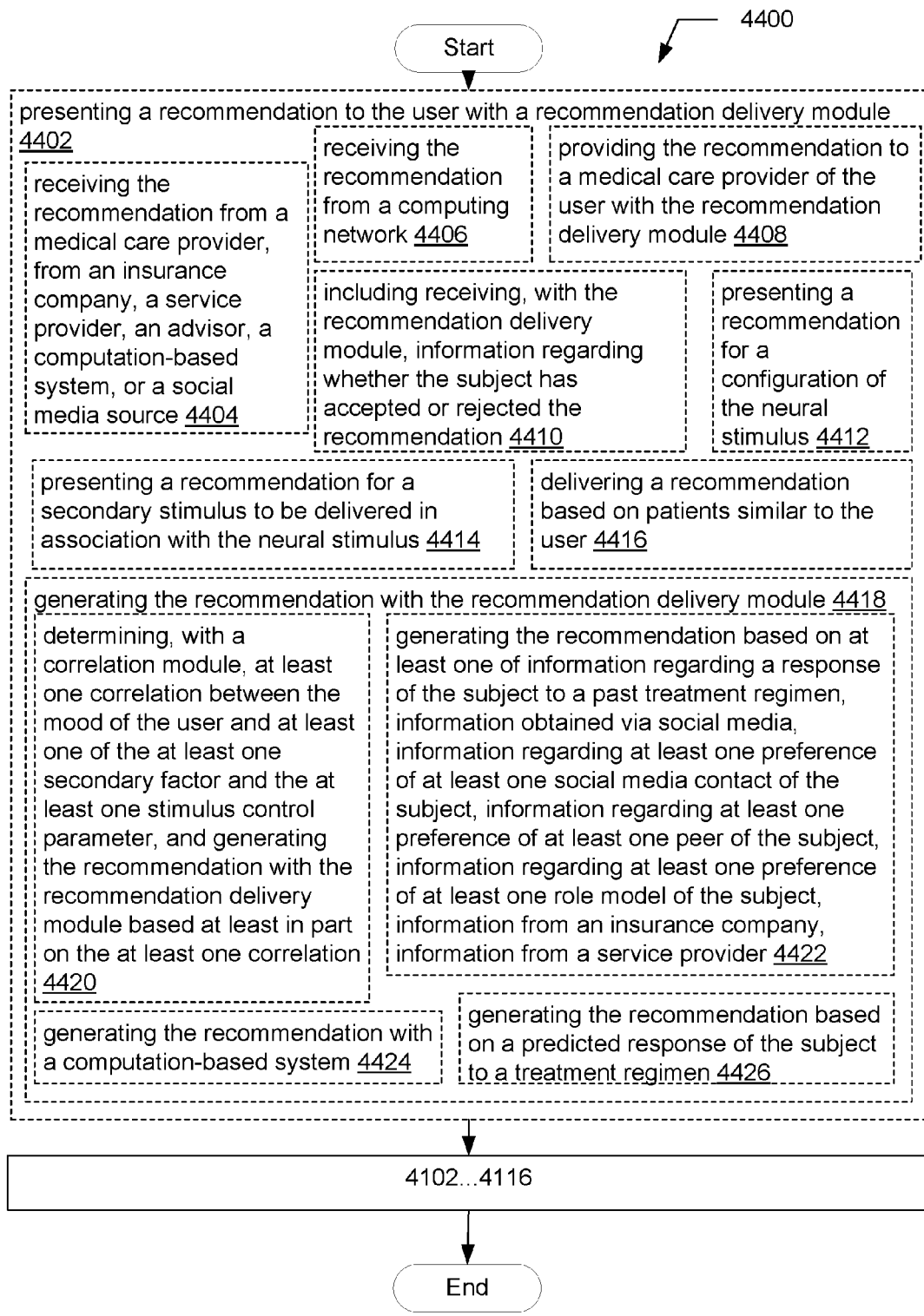
FIG. 44 is a flow diagram of a method.

As shown in FIG. 44, in an aspect a method 4400 includes presenting a recommendation to the user with a recommendation delivery module, as indicated at 4402. The recommendation may be received from a medical care provider, from an insurance company, a service provider, an advisor, a computation-based system, or a social media source, as indicated at 4404, or from a computing network, as indicated at 4406. In another aspect, method 4400 includes providing the recommendation to a medical care provider of the user with the recommendation delivery module, as indicated at 4408. In a further aspect, method 4400 includes receiving, with the recommendation delivery module, information regarding whether the subject has accepted or rejected the recommendation, as indicated at 4410.

In various aspects, presenting the recommendation includes presenting a recommendation for a configuration of the neural stimulus, as indicated at 4412, or presenting a recommendation for a secondary stimulus to be delivered in association with the neural stimulus, as indicated at 4414.

In an aspect, method 4400 includes delivering a recommendation based on patients similar to the user, as indicated at 4416.

In an aspect, method 4400 includes generating the recommendation with the recommendation delivery module, as indicated at 4418. For example, the method may include determining, with a correlation module, at least one correlation between the mood of the user and at least one of the at least one secondary factor and the at least one stimulus control parameter, and generating the recommendation with the recommendation delivery module based at least in part on the at least one correlation, as indicated at 4420. In an aspect, the method includes generating the recommendation based on at least one of information regarding a response of the subject to a past treatment regimen, information obtained via social media, information regarding at least one preference of at least one social media contact of the subject, information regarding at least one preference of at least one peer of the subject, information regarding at least one preference of at least one role model of the subject, information from an insurance company, information from a service provider, as indicated at 4422. In some aspects, the method includes generating the recommendation with a computation-based system, as indicated at 4424, or generating the recommendation based on a predicted response of the subject to a treatment regimen, as indicated at 4426.

Figure 45:
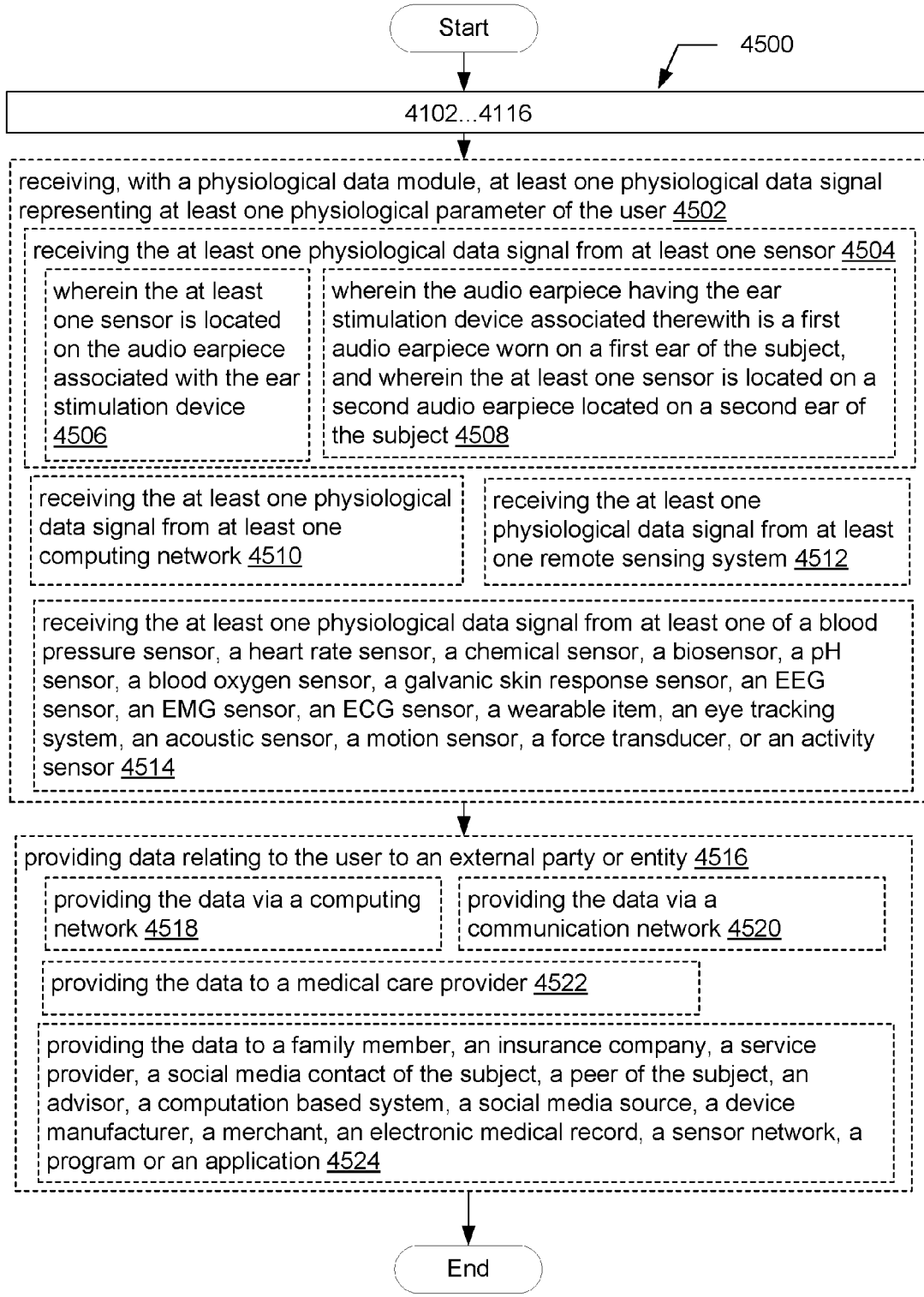
FIG. 45 is a flow diagram of a method.

FIG. 45 depicts aspects of a related method 4500. In an aspect, method 4500 includes receiving, with a physiological data module, at least one physiological data signal representing at least one physiological parameter of the user, as indicated at 4502. Receiving the at least one physiological data signal includes, for example, receiving the at least one physiological data signal from at least one sensor, as indicated at 4504. In an aspect, the at least one sensor is located on the audio earpiece associated with the ear stimulation device, as indicated at 4506. In an aspect, the audio earpiece having the ear stimulation device associated therewith is a first audio earpiece worn on a first ear of the subject, and wherein the at least one sensor is located on a second audio earpiece located on a second ear of the subject, as indicated at 4508.

In an aspect, receiving the at least one physiological data signal includes receiving the at least one physiological data signal from at least one computing network, as indicated at 4510, or from at least one remote sensing system, as indicated at 4512. In various aspects, receiving the at least one physiological data signal includes receiving the at least one physiological data signal from at least one of a blood pressure sensor, a heart rate sensor, a chemical sensor, a biosensor, a pH sensor, a blood oxygen sensor, a galvanic skin response sensor, an EEG sensor, an EMG sensor, an ECG sensor, a wearable item, an eye tracking system, an acoustic sensor, a motion sensor, a force transducer, or an activity sensor, as indicated at 4514.

In a further aspect, method 4500 includes providing data relating to the user to an external party or entity, as indicated at 4516. In various aspects, providing the data to the external party or entity includes providing the data via a computing network, as indicated at 4518, or providing the data via a communication network, as indicated at 4520. In an aspect, providing the data to the external party or entity includes providing the data to a medical care provider, as indicated at 5422. In various aspects, providing the data to the external party or entity includes providing the data to a family member, an insurance company, a service provider, a social media contact of the subject, a peer of the subject, an advisor, a computation based system, a social media source, a device manufacturer, a merchant, an electronic medical record, a sensor network, a program or an application, as indicated at 4524.

Figure 46:
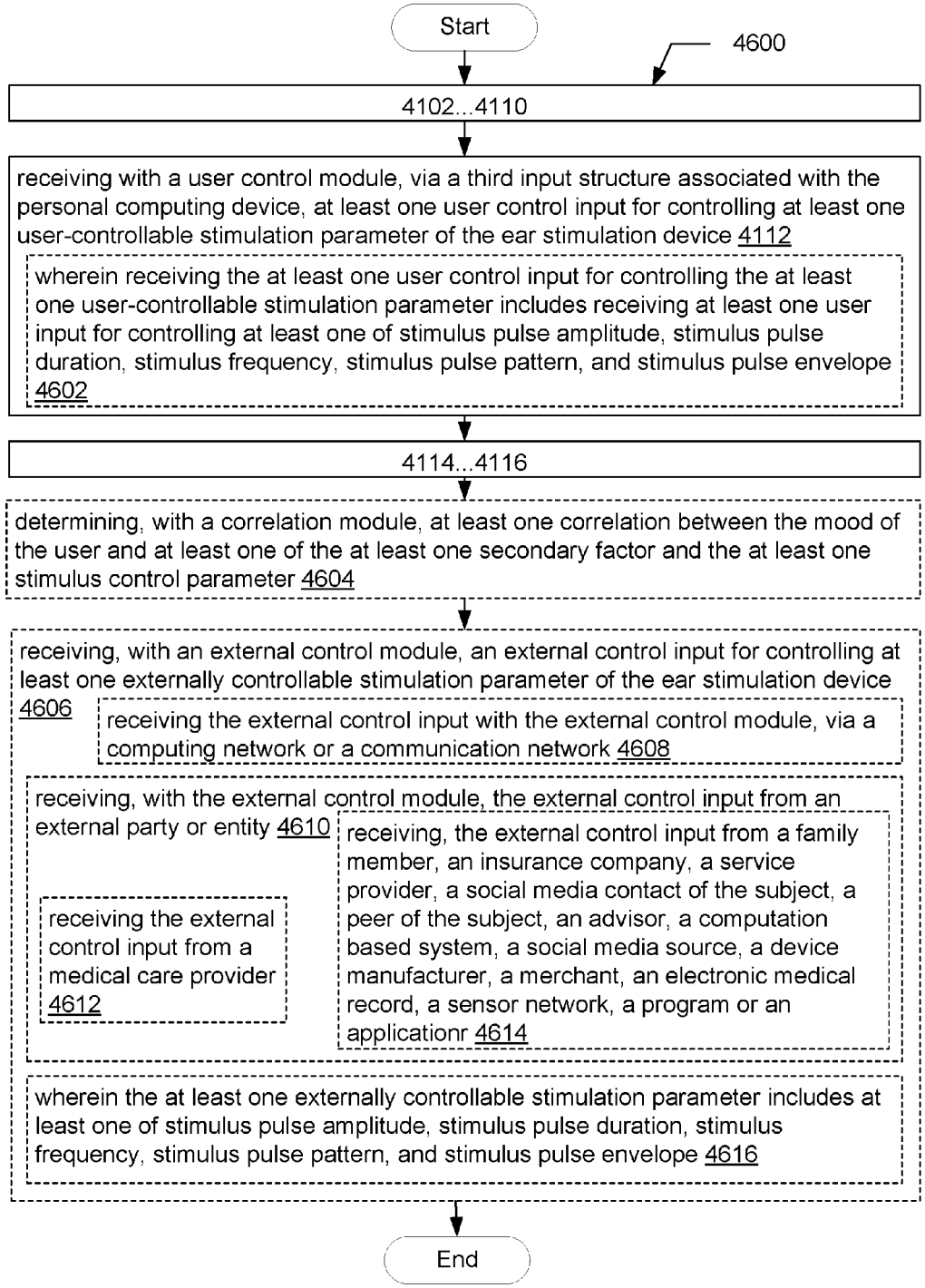
FIG. 46 is a flow diagram of a method.

FIG. 46 depicts further aspects of a method 4600. In one aspect of method 4600, receiving the at least one user control input for controlling the at least one user-controllable stimulation parameter includes receiving at least one user input for controlling at least one of stimulus pulse amplitude, stimulus pulse duration, stimulus frequency, stimulus pulse pattern, and stimulus pulse envelope, as indicated at 4602.

In another aspect, method 4600 includes determining, with a correlation module, at least one correlation between the mood of the user and at least one of the at least one secondary factor and the at least one stimulus control parameter, as indicated at 4604.

In another aspect, method 4600 includes receiving, with an external control module, an external control input for controlling at least one externally controllable stimulation parameter of the ear stimulation device, as indicated at 4606. In various aspects, this includes receiving the external control input via a computing network or a communication network, as indicated at 4608. In an aspect, receiving the external control input includes receiving the external control input from an external party or entity, as indicated at 4610, for example, a medical care provider, as indicated at 4612, or a family member, an insurance company, a service provider, a social media contact of the subject, a peer of the subject, an advisor, a computation based system, a social media source, a device manufacturer, a merchant, an electronic medical record, a sensor network, a program or an application, as indicated at 4614. In various aspect, the at least one externally controllable stimulation parameter includes at least one of stimulus pulse amplitude, stimulus pulse duration, stimulus frequency, stimulus pulse pattern, and stimulus pulse envelope, as indicated at 4616.

FIG. 47 depicts further aspects of a method 4700, relating to determining the at least one stimulus control parameter. In an aspect, determining the at least one stimulus control parameter includes overriding the at least one user control input for controlling the at least one user-controllable stimulation parameter based on a medical-care provider control input, as indicated at 4702. In another aspect, determining the at least one stimulus control parameter includes overriding a medical-care provider control input based on the at least one user control input for controlling the at least one user-controllable stimulation parameter, as indicated at 4704. In yet another aspect, determining the at least one stimulus control parameter includes overriding the at least one user control input for controlling the at least one user-controllable stimulation parameter based on a computing system-generated stimulus control parameter, as indicated at 4706. In still another aspect, determining the at least one stimulus control parameter includes overriding a computing system-generated stimulus control parameter based on the at least one user control input for controlling the at least one user-controllable stimulation parameter, as indicated at 4708.

In an aspect, determining the at least one stimulus control parameter includes determining an initial setting of the ear stimulation device based on the at least one user-controllable stimulation parameter, as indicated at 4710. In another aspect, determining the at least one stimulus control parameter includes updating a setting of the ear stimulation device based on the at least one user-controllable stimulation parameter, as indicated at 4712.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g., "configured to") generally encompass active-state components and/or inactive-state components and/or standby-state components, unless context requires otherwise.

A personal computing device, as described herein, may include circuitry and other hardware components, provided, for example in the form of a custom board installed in the case of the personal computing device during or after manufacture, or in a separate package that may be operably connected to the personal computing device via one or more wired and/or wireless connection. Unless context dictates otherwise, as used herein, the term personal computing device is intended to encompass systems including circuitry and other hardware components packaged with the personal computing device and circuitry and other hardware components packaged separately but used in combination with the personal computing device.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method of controlling an ear stimulation device with a personal computing device, comprising:
   capturing, with image capture circuitry on the personal computing device, via a user-facing camera associated with the personal computing device, an image of a user of the personal computing device;
   processing the image, using image processing circuitry on the personal computing device, to determine at least one parameter; and
   controlling, with neural stimulus control signal determination circuitry on the personal computing device, based at least in part on the at least one parameter, delivery of a stimulus to at least one nerve innervating a pinna of an ear of the user with the ear stimulation device,
   wherein the stimulus includes as least one of a mechanical stimulus, electrical stimulus, magnetic stimulus, ultrasonic stimulus, optical stimulus, or chemical stimulus.

2. The method of claim 1, wherein the image processing circuitry includes application software on the personal computing device.

3. The method of claim 1, wherein the at least one parameter is an emotional parameter of the user.

4. The method of claim 1, wherein the at least one parameter is a physiological parameter of the user.

5. The method of claim 1, wherein the at least one parameter is a medical parameter of the user.

6. The method of claim 1, wherein the at least one parameter is a biometric parameter indicative of an identity of the user.

7. The method of claim 1, wherein the at least one parameter is a heart rate of the user.

8. The method of claim 1, wherein the at least one parameter is an eye position or eye movement parameter of the user.

9. The method of claim 1, wherein the at least one parameter is a distance of one or more portions of an earpiece of the ear stimulation device with respect to at least one anatomical feature of the ear of the user.

10. The method of claim 9, including delivering, under control of notification circuitry on the personal computing device, a notification to the user informing the user of a need to adjust a position of the earpiece with respect to the ear of the user.

11. The method of claim 1, wherein the personal computing device includes a phone, watch, wearable device, tablet computer, laptop computer, or desktop computer.

12. The method of method of claim 1, including
   processing the image, using the image processing circuitry, to determine
      a presence of at least one earpiece of the ear stimulation device at the ear of the user, the ear selected from a right ear of the user and a left ear of the user; and
      at least one attribute of the at least one earpiece indicative of usability of the at least one earpiece with the ear of the user at which the earpiece is located;
   determining, using application software on the personal computing device, a target ear at which the at least one ear earpiece is usable, based on the at least one attribute of the at least one earpiece;
   determining, using application software on the personal computing device, that the ear at which the at least one earpiece is located is not the target ear at which the at least one earpiece is usable; and
   sending a control signal from the personal computing device to the ear stimulation device, under control of the neural stimulus control signal determination circuitry, to prevent delivery of a stimulus to the pinna of the ear at which the at least one earpiece is located via the at least one earpiece.

13. The method of claim 12, including receiving, with handshake circuitry on the personal computing device, a handshake signal from ear stimulation device control circuitry associated with the ear stimulation device.

14. The method of claim 13, including capturing the image of the user of the personal computing device responsive to receiving the handshake signal from the ear stimulation device control circuitry.

15. The method of claim 13, including sending a handshake signal to the ear stimulation device control circuitry responsive to determining the presence of the at least one earpiece located at the ear of the user in the image.

16. The method of claim 12, including delivering, under control of notification circuitry on the personal computing device, a notification to the user informing the user of a need to switch the at least one earpiece to the target ear if the ear at which the at least one earpiece is located is not the target ear at which the at least one earpiece is usable.

17. The method of claim 16, wherein delivering the notification to the user includes delivering a text notification.

18. The method of claim 16, wherein delivering the notification to the user includes delivering a visible notification.

19. The method of claim 16, wherein delivering the notification to the user includes delivering an audio notification.

20. The method of claim 12, wherein determining the at least one attribute of the at least one earpiece includes determining a shape of the at least one earpiece.

21. The method of claim 12, wherein determining the at least one attribute of the at least one earpiece includes determining a color of the at least one earpiece.

22. The method of claim 12, wherein determining the at least one attribute of the at least one earpiece includes determining a presence of an indicia on the at least one earpiece or an attachment to the at least one earpiece.

23. The method of claim 22, wherein the attachment to the at least one earpiece includes a cable connected to the at least one earpiece.

24. An ear stimulation device control system, comprising:
a personal computing device;
a user-facing camera associated with the personal computing device;
image capture circuitry adapted to capture an image of a user of the personal computing device from the user-facing camera;
image processing circuitry configured to process the image to determine at least one parameter; and
neural stimulus control signal determination circuitry configured to control delivery of a stimulus to at least one nerve innervating a pinna of an ear of the user with an ear stimulation device, based at least in part on the at least one parameter,
wherein the stimulus includes as least one of a mechanical stimulus, electrical stimulus, magnetic stimulus, ultrasonic stimulus, optical stimulus, or chemical stimulus.

25. The system of claim 24, wherein the at least one parameter is an emotional parameter of the user.

26. The system of claim 24, wherein the at least one parameter is a physiological parameter of the user.

27. The system of claim 24, wherein the at least one parameter is a biometric parameter indicative of an identity of the user.

28. The system of claim 24, wherein the at least one parameter is a heart rate of the user.

29. The system of claim 24, wherein the at least one parameter is an eye position or eye movement parameter of the user.

30. The system of claim 24, wherein the at least one parameter is a distance of one or more portions of an earpiece of the ear stimulation device with respect to at least one anatomical feature of the ear of the user.

31. The system of claim 24, wherein the personal computing device includes a phone, watch, wearable device, tablet computer, laptop computer, or desktop computer.

32. The system of claim 24, wherein the image processing circuitry includes an earpiece location module configured to process the image to determine
a presence of at least one earpiece of the ear stimulation device at the ear of the user, the ear selected from a right ear of the user and a left ear of the user; and
at least one attribute of the at least one earpiece indicative of usability of the at least one earpiece with the ear of the user at which the at least one earpiece is located; and
wherein the neural stimulus control signal determination circuitry is configured to
determine a target ear at which the earpiece is usable, based on the at least one attribute of the at least one earpiece;
determine that the ear at which the at least one earpiece is located is not the target ear at which the earpiece is usable; and if the ear at which the at least one earpiece is located is not the ear at which the earpiece is usable; and
send a control signal from the personal computing device to the ear stimulation device to prevent delivery of the stimulus to the at least one nerve innervating the pinna of the ear of the user.

33. The system of claim 32, including handshake circuitry adapted to receive a handshake signal from ear stimulation device control circuitry associated with the ear stimulation device.

34. The system of claim 33, wherein the image capture circuitry is adapted to capture the image of the user of the personal computing device responsive to receiving the handshake signal from the ear stimulation device control circuitry.

35. The system of claim 33, wherein the neural stimulus control signal determination circuitry is configured to send a handshake signal to the ear stimulation device control circuitry responsive to determining the presence of the at least one earpiece located at the ear of the user in the image.

36. The system of claim 32, including
an output device; and
notification circuitry adapted to provide a notification via the output device instructing the user to switch the at least one earpiece to the other ear if the ear at which the at least one earpiece is located is not the target ear at which the earpiece is usable.

37. The system of claim 36, wherein the output device is adapted to deliver a text notification to the user.

38. The system of claim 36, wherein the output device is adapted to deliver a visible notification to the user.

39. The system of claim 36, wherein the output device is adapted to deliver an audio notification to the user.

40. The system of claim 32, wherein the at least one attribute of the at least one earpiece includes a shape of the at least one earpiece.

41. The system of claim 32, wherein the at least one attribute of the at least one earpiece includes a color of the at least one earpiece.

42. The system of claim 32, wherein the at least one attribute of the at least one earpiece includes a presence of an indicia on the at least one earpiece or an attachment to the at least one earpiece.

43. The system of claim 42, wherein the attachment to the at least one earpiece includes a cable connected to the at least one earpiece.

44. An ear stimulation device control system, comprising:
a personal computing device;
a user-facing camera associated with the personal computing device;
image capture circuitry adapted to capture an image of a user of the personal computing device from the user-facing camera;
image processing circuitry configured to process the image to determine at least one parameter, wherein the image processing circuitry includes
an earpiece location module configured to process the image to determine a presence of at least one earpiece of the ear stimulation device at the ear of the user, the ear selected from a right ear of the user and a left ear of the user; and at least one attribute of the at least one earpiece indicative of usability of the at least one earpiece with the ear of the user at which the earpiece is located; and neural stimulus control signal determination circuitry configured to control delivery of a stimulus to at least one nerve innervating an ear of the user with an ear stimulation device, based at least in part on the at least one parameter, wherein the neural stimulus control signal determination circuitry is configured to determine a target ear at which the at least one earpiece is usable, based on the at least one attribute of the at least one earpiece;

determine that the ear at which the at least one earpiece is located is not the target ear at which the at least one earpiece is usable; and send a control signal from the personal computing device to the ear stimulation device to prevent delivery of the stimulus to the a least one nerve innervating the ear of the user.

* * * * *